(12) United States Patent
Kondo et al.

(10) Patent No.: US 12,733,993 B1
(45) Date of Patent: Sep. 15, 2026

(54) IMAGE PROCESSING DEVICE, ENDOSCOPE SYSTEM, IMAGE PROCESSING METHOD, AND INFORMATION STORAGE MEDIUM

(71) Applicant: OLYMPUS CORPORATION, Tokyo (JP)

(72) Inventors: Ryosuke Kondo, Tachikawa (JP); Ryuichi Yorimoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 2 days.

(21) Appl. No.: 19/076,020

(22) Filed: Mar. 11, 2025

(51) Int. Cl.

| | |
|---|---|
| ***A61B 34/20*** | (2016.01) |
| ***A61B 1/00*** | (2006.01) |
| ***A61B 1/04*** | (2006.01) |
| ***A61B 1/313*** | (2006.01) |
| ***G06T 7/70*** | (2017.01) |

(52) U.S. Cl.
CPC .......... *A61B 34/20* (2016.02); *A61B 1/00004* (2013.01); *A61B 1/00006* (2013.01); *A61B 1/00009* (2013.01); *A61B 1/0005* (2013.01); *A61B 1/00194* (2022.02); *A61B 1/04* (2013.01); *A61B 1/3132* (2013.01); *G06T 7/70* (2017.01); *A61B 2034/2055* (2016.02); *A61B 2034/2065* (2016.02); *G06T 2207/10068* (2013.01)

(58) Field of Classification Search
CPC .......... A61B 1/3132; A61B 2034/2065; A61B 2034/2055; A61B 2034/2057
See application file for complete search history.

(56) References Cited

U.S. PATENT DOCUMENTS

| | | | | |
|---|---|---|---|---|
| 6,690,963 B2 * | 2/2004 | Ben-Haim | A61N 1/32 | 606/41 |
| 6,788,967 B2 * | 9/2004 | Ben-Haim | A61B 34/20 | 600/424 |
| 7,202,941 B2 * | 4/2007 | Munro | G01S 17/10 | 356/5.1 |
| 2007/0167702 A1 * | 7/2007 | Hasser | A61B 90/36 | 600/407 |

(Continued)

FOREIGN PATENT DOCUMENTS

| | | |
|---|---|---|
| JP | 7332713 B2 | 8/2023 |

OTHER PUBLICATIONS

Japanese Office Action dated Oct. 14, 2025 received in 2024-141079.

*Primary Examiner* — Colin T. Sakamoto
(74) *Attorney, Agent, or Firm* — Scully, Scott, Murphy & Presser, P.C.

(57) ABSTRACT

An image processing device includes a processor comprising hardware. The processor calculate based on an endoscope image of a subject, the endoscope image being acquired by an endoscope, three-dimensional position information regarding a first treatment tool and a first portion in the endoscope image. Additionally, the processor measures a distance between the first measurement point on a distal end side of the first treatment tool and a second measurement point associated with the first portion based on the three-dimensional position information regarding the first treatment tool and the first portion, and perform a determination of whether a measurement of the distance is in a stable state and control a display to display a result of the determination.

20 Claims, 37 Drawing Sheets

(56) References Cited

U.S. PATENT DOCUMENTS

2010/0317965 A1 12/2010 Itkowitz et al.
2021/0256719 A1* 8/2021 Hufford .................. G06T 11/00
2022/0296079 A1 9/2022 Takahashi

* cited by examiner

FIG.4

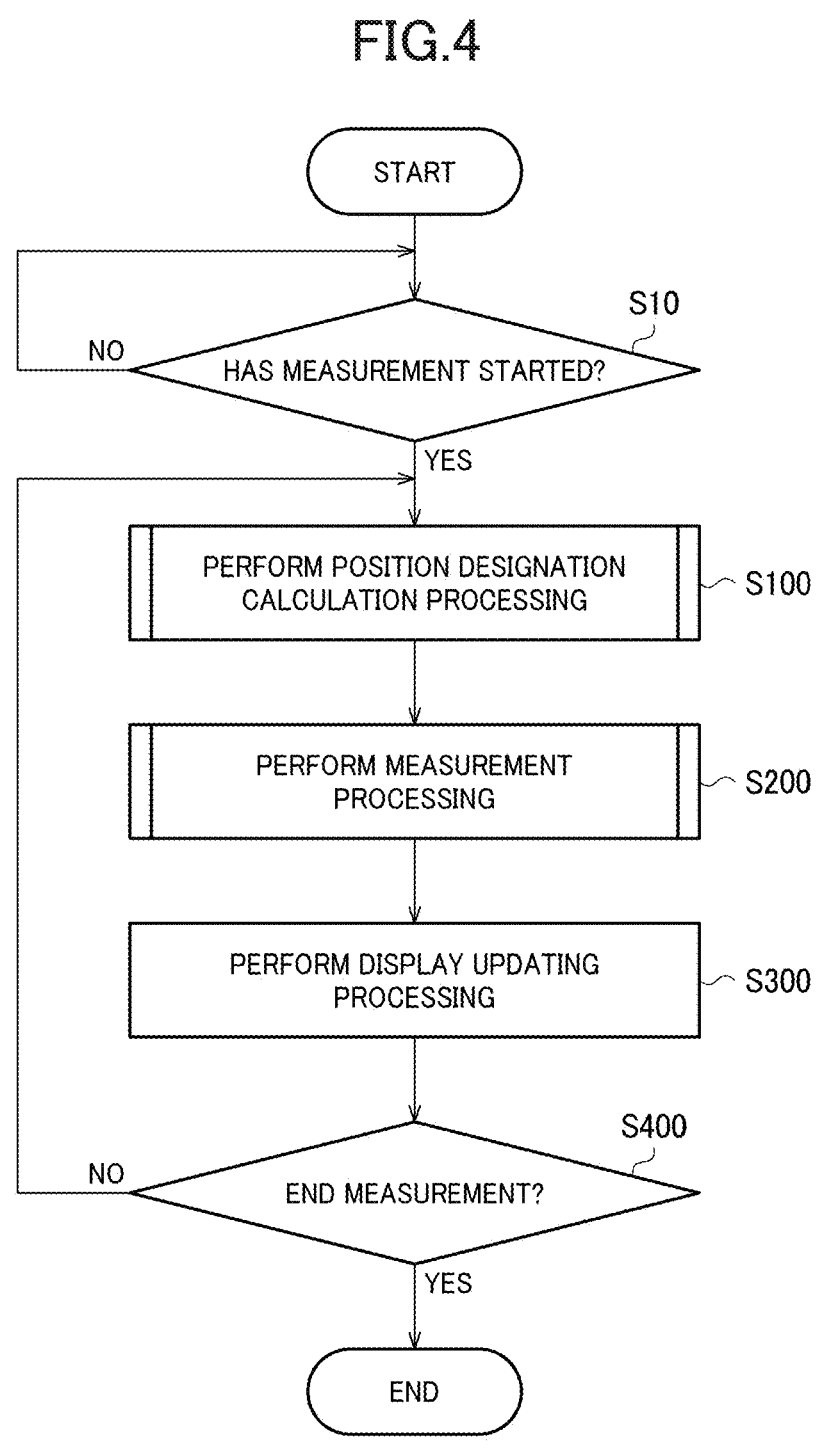

START
S10
HAS MEASUREMENT STARTED?
NO
YES
PERFORM POSITION DESIGNATION CALCULATION PROCESSING
S100
PERFORM MEASUREMENT PROCESSING
S200
PERFORM DISPLAY UPDATING PROCESSING
S300
S400
END MEASUREMENT?
NO
YES
END

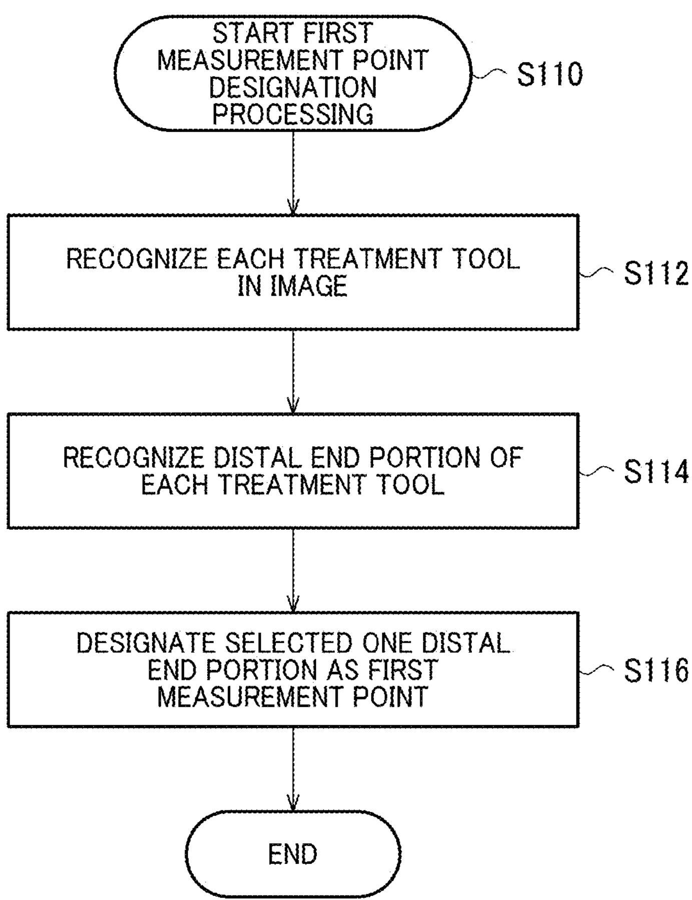
FIG.6
START FIRST MEASUREMENT POINT DESIGNATION PROCESSING
S110
RECOGNIZE EACH TREATMENT TOOL IN IMAGE
S112
RECOGNIZE DISTAL END PORTION OF EACH TREATMENT TOOL
S114
DESIGNATE SELECTED ONE DISTAL END PORTION AS FIRST MEASUREMENT POINT
S116
END

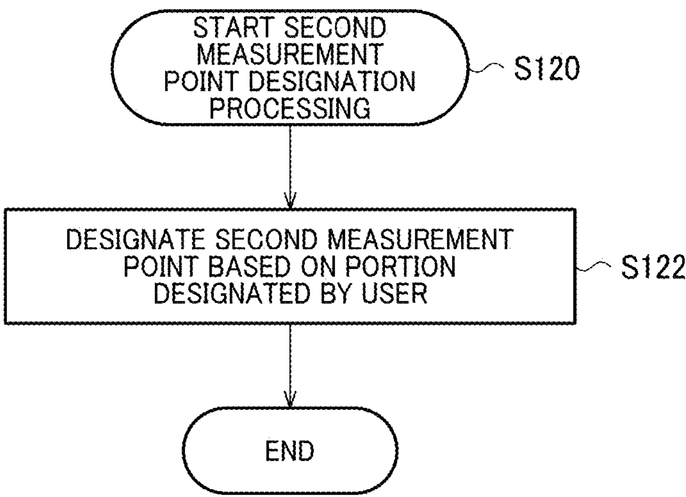
FIG.7
START SECOND MEASUREMENT POINT DESIGNATION PROCESSING
S120
DESIGNATE SECOND MEASUREMENT POINT BASED ON PORTION DESIGNATED BY USER
S122
END

DP2
A10
A11
※100
A12
41
42
A16
31
A13
A14
TREATMENT TOOL
STABILITY ×
A15

FIG.12

| DEGREE OF STABILITY OF TREATMENT TOOL | MODE PATTERNS | | | |
|---|---|---|---|---|
| | P−A1 | P−A2 | P−A3 | P−A4 |
| 100% | ◎ | ○ | ○ | OK |
| 80% to 100% | ○ | ○ | × | NG |
| 60% to 80% | △ | △ | × | NG |
| 0% to 60% | × | × | × | NG |

FIG.15
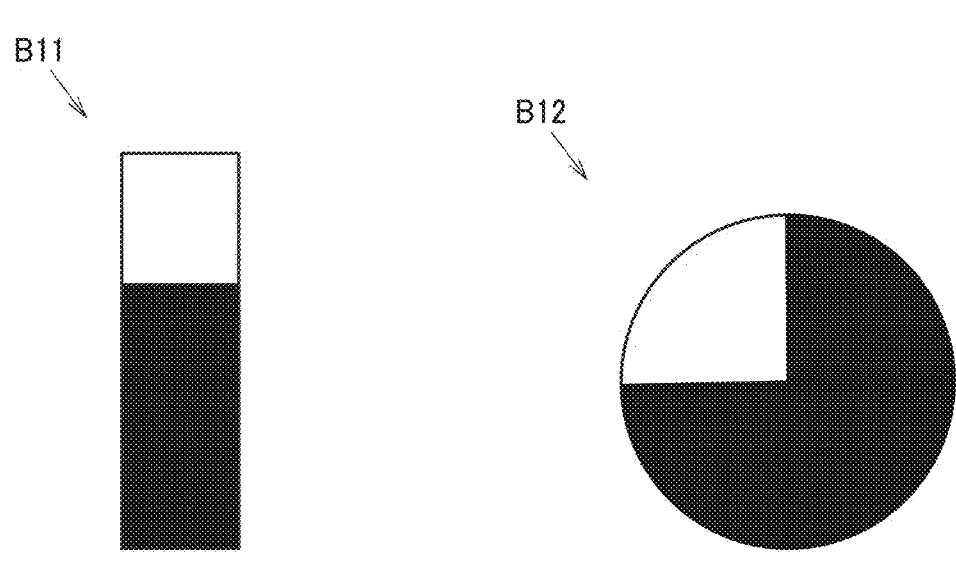
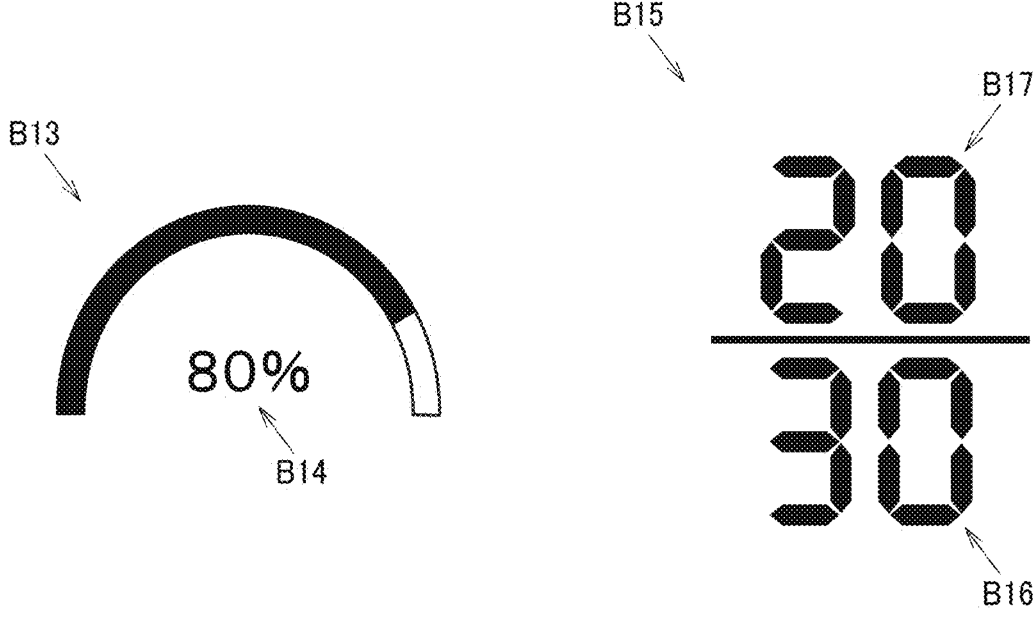

FIG.16

| DISPLAY MODES OF MEASURED DISTANCE | IN CASE WHERE TREATMENT TOOL IS NOT STABLE | IN CASE WHERE TREATMENT TOOL IS STABLE |
|---|---|---|
| P−B1 | B22 ※100 B21 | B23 100 |
| P−B2 | 100 | 100 |
| P−B3 | B24 ※100 | B25 100 |
| P−B4 | HIDDEN | 100 |

DP2
A50
A51
100
A52
42
41
A56
31
A53
A54
TREATMENT TOOL STABILITY
A55

DP2
A60
42
31
A63
A64
A65
A66
A67
A68
TREATMENT TOOL
STABILITY ×

DP2
A90
A98
A98
31
A97
TREATMENT TOOL IS HORIZONTAL
TO SCREEN.
PLEASE ROTATE SCOPE.

FIG.30
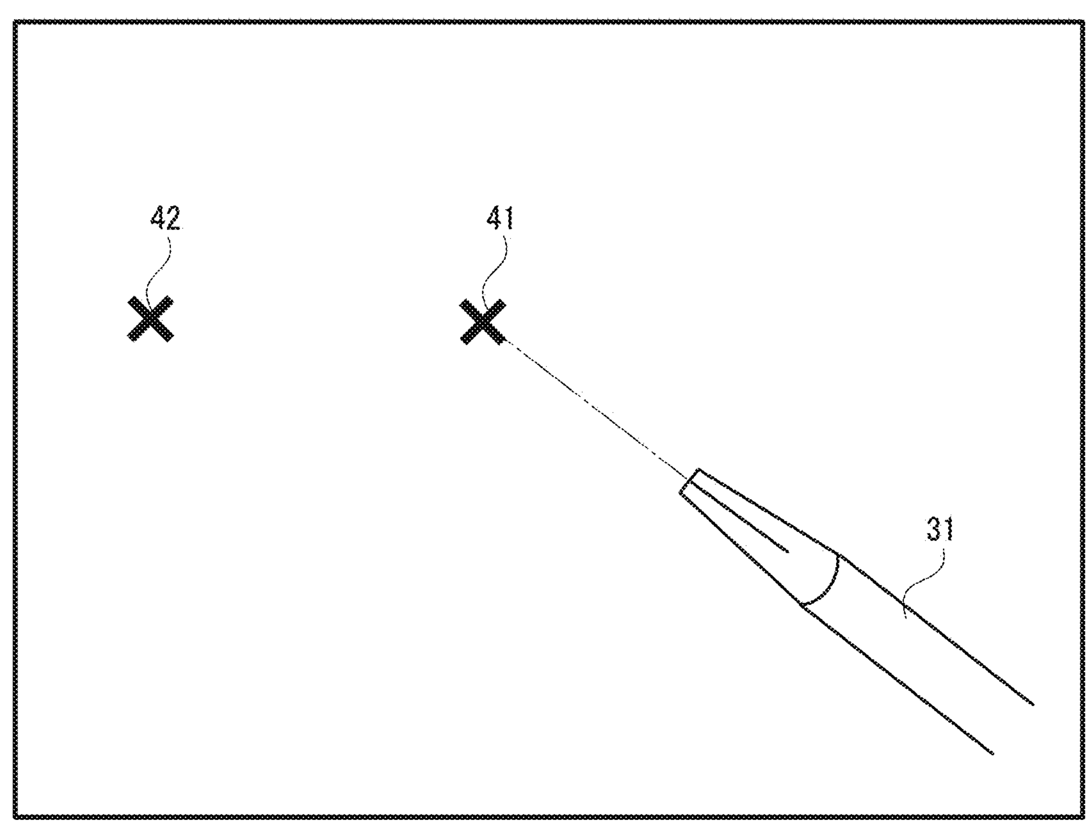

IMAGE PROCESSING DEVICE, ENDOSCOPE SYSTEM, IMAGE PROCESSING METHOD, AND INFORMATION STORAGE MEDIUM

CROSS REFERENCE TO RELATED APPLICATIONS

This application is based upon and claims the benefit of priority to U.S. Provisional Patent Application No. 63/564,011 filed on Mar. 12, 2024, the entire contents of which are incorporated herein by reference.

BACKGROUND

An image processing device that displays an image, which is acquired from an endoscope in surgery or the like, on a display has been conventionally known. The specification of U.S. Unexamined Patent Application Publication No. 2010/0317965 discloses a method of displaying a measurement value obtained by measurement of a distance between points designated by a distal end of a robot tool used in surgery.

SUMMARY

According to one aspect of the disclosure, there is provided an image processing device comprising: a processor comprising hardware, wherein the processor is configured to:

calculate, based on an endoscope image of a subject, the endoscope image being acquired by an endoscope, three-dimensional position information regarding a first treatment tool and a first portion in the endoscope image;

measure a distance between a first measurement point on a distal end side of the first treatment tool and a second measurement point associated with the first portion based on the three-dimensional position information regarding the first treatment tool and the first portion; perform a determination of whether a measurement of the distance is in a stable state; and control a display to display a result of the determination.

According to one aspect of the disclosure, there is provided an endoscope system comprising:

the image processing device as defined in claim 1; and an endoscope.

According to one aspect of the disclosure, there is provided an image processing method to be executed by a computer, the method comprising:

calculating, based on an endoscope image of a subject, the endoscope image being acquired by an endoscope, three-dimensional position information regarding a first treatment tool and a first portion in the endoscope image;

measuring a distance between a first measurement point on a distal end side of the first treatment tool and a second measurement point associated with the first portion based on the three-dimensional position information regarding the first treatment tool and the first portion;

performing a determination of whether a measurement of the distance is in a stable state; and controlling a display to display a result of the determination.

According to one aspect of the disclosure, there is provided a non-transitory information storage medium that stores a program to cause a computer to execute processes comprising:

performing processing of displaying an endoscope image of a subject on a display, the endoscope image being acquired by an endoscope;

using the endoscope image of the subject to calculate three-dimensional position information regarding a first treatment tool and a first portion in the endoscope image;

measuring a distance between a first measurement point on a distal end side of the first treatment tool and a second measurement point associated with the first portion based on the three-dimensional position information regarding the first treatment tool and the first-portion; and performing processing of displaying whether or not measurement of the distance is in a stable state.

BRIEF DESCRIPTION OF THE DRAWINGS

FIG. 4 is a flowchart describing a processing example of a method in accordance with the present embodiment.

FIG. 6 is a flowchart describing a processing example of first measurement point designation processing.

FIG. 7 is a flowchart describing a processing example of second measurement point designation processing.

FIG. 12 is a diagram for describing examples of modes representing a degree of stability of the treatment tool.

FIG. 15 is a view for describing examples of icons each representing a period of time in which distance measurement is stable.

FIG. 16 is a diagram for describing examples of modes of displaying a measured distance.

FIG. 30 is a view for describing an image example including the first measurement point designated in another processing example of the first measurement point designation processing.

DETAILED DESCRIPTION

Figure 1:
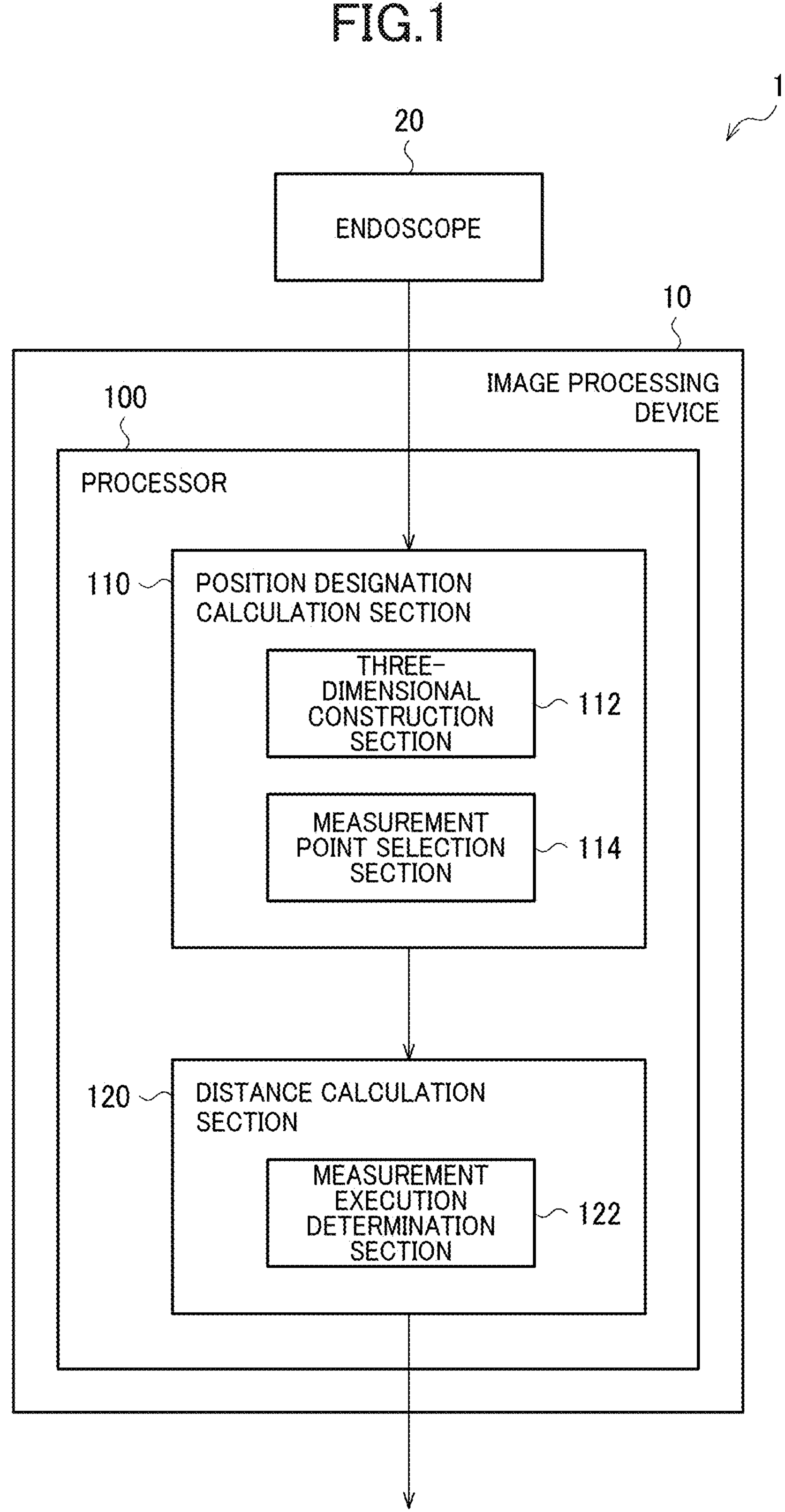
FIG. 1 is a block diagram for describing a configuration example of an image processing device included in an endoscope system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

FIG. 1 is a block diagram for describing a configuration example of an endoscope system 1 in accordance with the present embodiment. The endoscope system 1 in accordance with the present embodiment includes an image processing device 10 and an endoscope 20. The image processing device 10 includes a processor 100. The processor 100 in accordance with the present embodiment has the following hardware configuration. The hardware can include at least one of a circuit that processes a digital signal or a circuit that processes an analog signal. For example, the hardware can include one or more circuit devices mounted on a circuit board, or one or more circuit elements. The one or more circuit devices are, for example, integrated circuits (ICs) or the like. The one or more circuit elements are, for example, resistors, capacitors, or the like.

For example, the image processing device 10 in accordance with the present embodiment may have a configuration including a memory, which is not illustrated in FIG. 1, and the processor 100 that operates based on information stored in the memory. This allows the processor 100 to function as a position designation calculation section 110, a three-dimensional construction section 112, a measurement point selection section 114, a distance calculation section 120, a measurement execution determination section 122, and the like. Note that a main section that performs processing associated with the method in accordance with the present embodiment, which will be described below, is collectively described as the processor 100 for explanatory convenience. Additionally, the information stored in the memory is, for example, a program, various kinds of data, and the like. A central processing unit (CPU), a graphics processing unit (GPU), a digital signal processor (DSP), or the like can be used as the processor 100. The memory may be a volatile memory such as a static random access memory (SRAM) and a dynamic random access memory (DRAM), a non-volatile memory such as a read only memory (ROM), a register, a magnetic storage device such as a hard disk device, or an optical storage device such as an optical disk device. For example, the memory stores a computer-readable instruction. The instruction is executed by the processor 100, whereby a function of each section is implemented as processing. The instruction mentioned herein may be an instruction set that is included in the program, or may be an instruction that instructs the hardware circuit included in the processor 100 to operate. In addition, the memory is also referred to as a storage device.

Furthermore, the above-mentioned program can be stored in, for example, a non-transitory information storage medium, which is a computer-readable storage medium. The information storage medium can be implemented by, for example, an optical disk, a memory card, a hard disk device, a non-volatile memory, or the like.

Figure 2:
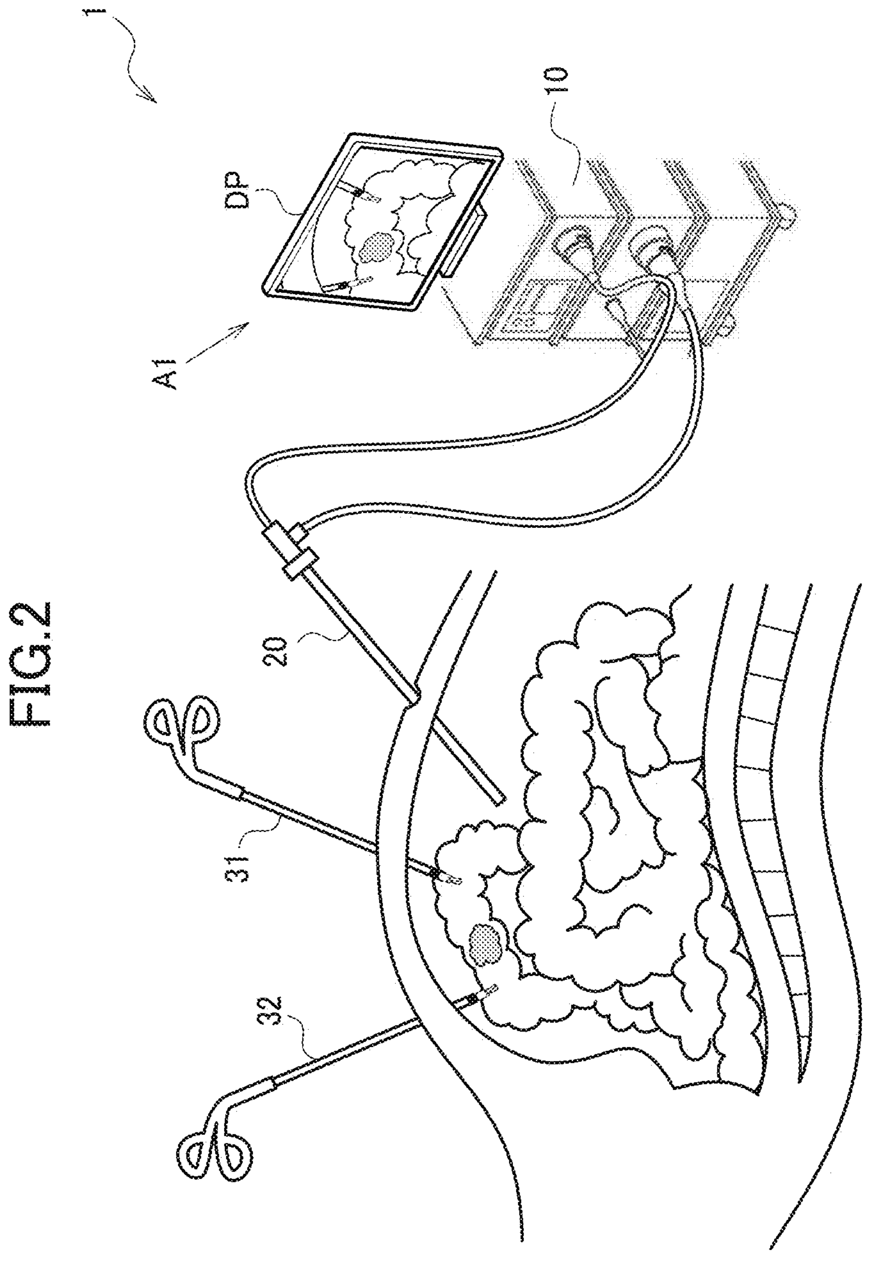
FIG. 2 is a view for describing the endoscope system in detail.

The method in accordance with the present embodiment can be applied to, for example, a treatment in endoscopic surgery, which is illustrated in FIG. 2. In this case, more specifically, it can be said that the endoscope system 1 functions as endoscopic surgery system. Note that FIG. 2 is a schematic view in which illustration of a trocar is omitted or the like, and does not illustrate endoscopic surgery in a strict manner.

In FIG. 2, the image processing device 10 is connected with the endoscope 20 and is also connected with a display DP. In the endoscopic surgery illustrated in FIG. 2, a plurality of holes is bored in a body wall of a subject, the endoscope 20 is inserted into a body cavity from one of the holes, and treatment tools are inserted into the body cavity from the other holes. In this case, the endoscope 20 is a rigid endoscope in which a major part of an insertion portion is rigid. Note that FIG. 2 illustrates a state where a first treatment tool 31 and a second treatment tool 32 are inserted into the body cavity, but the number of treatment tools is not limited to two.

While detailed illustration of the rigid endoscope is omitted because it is well known, the distal end of the endoscope 20 as the rigid endoscope includes an imager. That is, the image processing device 10 receives, via a cable, an image signal from the imager, which is provided at a distal end portion of the endoscope 20. The imager and the cable are not illustrated. Note that in the following description, the endoscope 20 may be referred to as a scope. The image processing device 10 then generates a display image based on the received image signal and performs processing of displaying the display image on the display DP as illustrated in A1 in FIG. 2. In other words, the processor 100 performs display control of the display DP. In the present embodiment, an image captured by the imager, which is provided at the distal end of the endoscope 20, is referred to as an endoscope image. Note that in the following description, the endoscope image may be simply denoted as an image. With the endoscope system 1 having such a configuration, the endoscope image obtained by the endoscope 20 is displayed on the display DP, which makes it possible for a user to perform a treatment on a biological tissue in the body cavity with the treatment tools while observing the biological tissue. The user in the present embodiment is, for example, other than an operator that handles the treatment tools, an endoscopist that operates the endoscope 20, a person in general who is associated with the treatment. Note that, in recent endoscopic surgery, there is a case where a surgery robot system in which the user operates a console to control a robot arm and perform a treatment is adopted, but the surgery robot system is not always adopted in all facilities. There is a case where the user operates the endoscope 20, the first treatment tool 31, the second treatment tool 32, or the like with hands.

Figure 3:
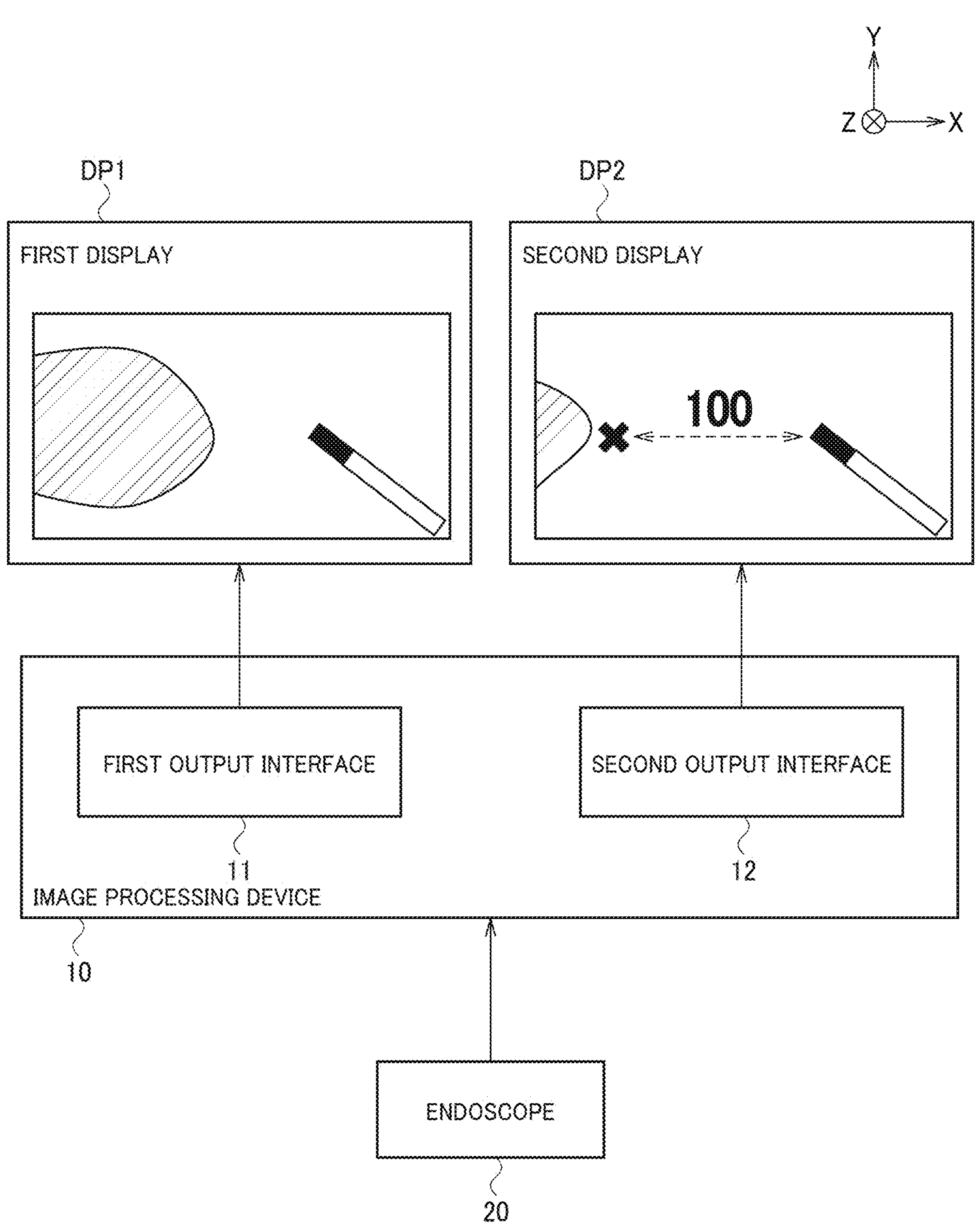
FIG. 3 is another view for describing the endoscope system in detail.

Additionally, FIG. 2 illustrates only one display DP, but the number of displays DP with which the image processing device 10 can be connected is not limited to one. For example, as illustrated in FIG. 3, the image processing device 10 may be connectable with a first display DP1 and a second display DP2. In this case, the processor 100, which is not illustrated in FIG. 2, may be connected with the first display DP1 via a first interface 11, and connected with the second display DP2 via a second interface 12. In this case, the processor 100 that displays an image on the first display DP1 and the processor 100 that displays an image on the second display DP2 may be identical, but may be different. In the following description, there is a case where the display DP is denoted by the first display DP1 and the second display DP2 being differentiated.

Additionally, the display DP in the present embodiment may be a display device having a first display mode of displaying a stereoscopic image. The stereoscopic image is an image that gives a three-dimensional appearance to the user. Specifically, this can be implemented by adopting a parallax barrier system display device, but may be implemented by a lenticular system display device, and various kinds of methods can be adopted. The parallax barrier system display device uses a system of using a parallax barrier to cause the user's left eye to visually recognize an image for a left eye and cause the user's right eye to visually recognize an image for a right eye and thereby displaying the stereoscopic image. Additionally, the display DP in the present embodiment may be a display device further having a second display mode of displaying a two-dimensional endoscope image, or may be configured to be capable of switching between the first display mode and the second display mode. For example, switching between valid and invalid of a parallax barrier function enables switching between the first display mode and the second display mode.

Additionally, the display DP in the present embodiment may further have a touch panel function. In other words, the display DP in the present embodiment may further include a pointing device for instructing a freely-selected position within a screen. A detection system is not specifically limited, and may be a static capacitance system, a resistive film system, an ultrasonic wave system, an infrared radiation system, an electromagnetic system, or the like and determined as appropriate by the user. For example, although not illustrated, the display DP includes a touch panel control circuit that detects the user's touch operation. The touch panel control circuit detects the user's touch operation, and outputs coordinate data, which is specified by the user's touch operation, on the display DP to the processor 100. The user's touch operation mentioned herein is, for example, an operation of bringing the user's finger into contact with a surface of the display DP, but may further include an operation of sliding the user's finger in a state where the finger is in contact with the surface of the display DP, an operation of separating the user's finger from the surface of the display DP, and the like. Additionally, the user's touch operation is not limited to an operation performed by the user's finger, and may be an operation performed with a touch pen gripped by the user. The touch pen is a device that implements a touch operation that is equivalent to a touch operation by the user's finger. For example, in a case where the touch panel function adopting the static capacitance system as the detection system is used, the touch pen is configured to include a conductive body at the distal end of the touch pen.

Additionally, for example, the first display DP1 and the second display DP2 may display different images. Specifically, for example, the first display DP1 may be capable of displaying an image observed mainly by the user and the second display DP2 may be capable of displaying predetermined information. The predetermined information is distance information or the like. The distance information is information regarding a distance between two predetermined measurement points designated by a predetermined method, which will be described later in detail. The two predetermined measurement points are, for example, a first measurement point 41 and a second measurement point 42, which will be described later. The method in accordance with the present embodiment relates to designation of the two measurement points, measurement of a distance between the two measurement points, and determination about whether or not the measurement can be performed.

Figure 10:
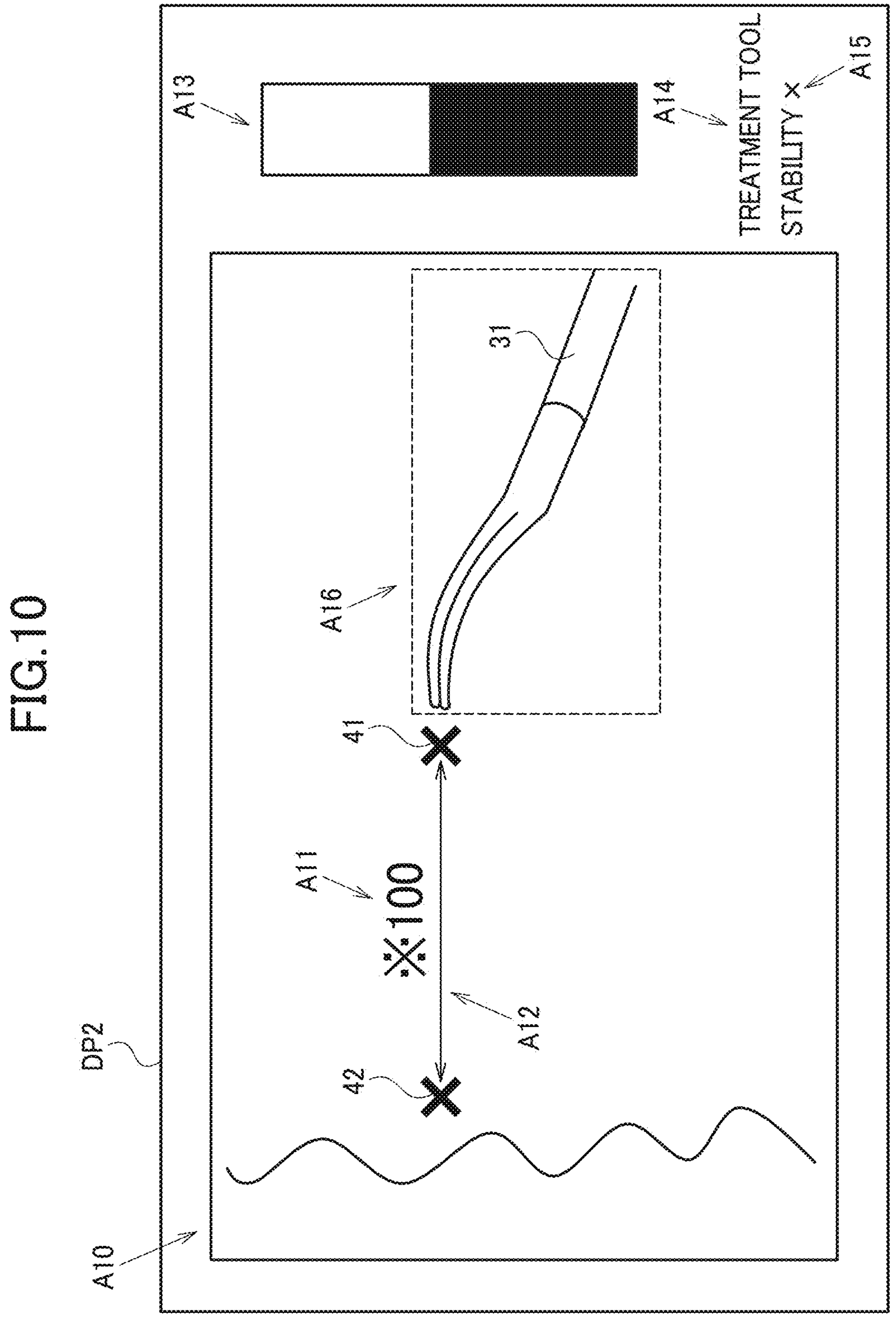
FIG. 10 is a view for describing a screen example in a case where a treatment tool is not stable.

In the present embodiment, for example, assume that a screen example to which the method in accordance with the present embodiment is applied is displayed on the second display DP2, as illustrated in FIG. 10, which will be described later. However, this is merely an example, and does not restrict the use of other display methods. For example, a screen similar to a screen illustrated in FIG. 10 may be displayed in part of the first display DP1. The same applies to screen examples in FIGS. 11, 14, 17, 18, 19, 22, 23, 25, 30, 36, and 37, which will be described later. Additionally, these screen examples are illustrated in a plan view for the sake of convenience, but in a case where the method in accordance with the present embodiment is actually applied, these screen examples are not prevented from being displayable as stereoscopic images.

Furthermore, in the present embodiment, as described later, a method of obtaining position information regarding the two predetermined measurement points is exemplified by a first method of performing calculation based on a distal end position of a treatment tool shown on the second display DP2 and a second method of performing calculation based on a subject position corresponding to a position, which is designated by the user, on the second display DP2. In the present embodiment, for simplification of the description, in a case where the position information regarding the two predetermined measurement points is obtained with use of both the first method and the second method, assume that a measurement point whose position information is obtained by the first method is the first measurement point 41 and a measurement point whose position information is obtained by the second method is the second measurement point 42. Note that, as described later with reference to FIG. 14, assume that the position information regarding the first measurement point 41 and the second measurement point 42 can be obtained with use of only the first method.

The processor 100 included in the image processing device 10 in accordance with the present embodiment functions as the position designation calculation section 110 illustrated in FIG. 1, and thereby calculates the position information regarding the designated, two predetermined measurement points. Additionally, the position designation calculation section 110 includes the three-dimensional construction section 112. That is, the position information regarding the two predetermined measurement points is three-dimensional position information, and the processor 100 functions as the three-dimensional construction section 112 and can thereby calculate the three-dimensional position information regarding the two predetermined measurement points, as described later.

Additionally, the processor 100 functions as the distance calculation section 120 illustrated in FIG. 1, and thereby calculates a distance based on the position information calculated by the position designation calculation section 110. Specifically, the processor 100 calculates a distance between the first measurement point 41 and the second measurement point 42 based on the three-dimensional position information regarding the first measurement point 41 and the three-dimensional position information regarding the second measurement point 42. The first measurement point 41 and the second measurement point 42 may be hereinafter simply referred to as the "distance". Additionally, the distance calculation section 120 includes the measurement execution determination section 122. That is, the processor 100 functions as the measurement execution determination section 122, and determines whether or not distance measurement (measurement of the distance) is stable so as to execute the distance measurement.

Note that, in the present embodiment, the distance measurement being stable specifically means, for example, a less variation in position information regarding the first measurement point 41 and a less variation in position information regarding the second measurement point 42. For example, the processor 100 performs treatment tool stability determination processing (step S250), which will be described later, to determine whether or not the distance measurement is stable. Additionally, the distance measurement being stable may mean a less variation in the measured distance, which will be described later with reference to FIG. 13. Furthermore, for example, the distance measurement being stable may include an endoscope image being stable, which will be described later in detail with reference to FIG. 21 and the like.

The processor 100 then functions as a video processor, and displays information regarding the measured distance on the display DP. More specifically, by taking an example in FIG. 3, the processor 100 performs processing of iconizing the information regarding the measured distance, and processing of displaying the information on the second display DP2 via the second interface 12. Additionally, the processor 100 is also capable of displaying information other than the information regarding the measured distance, which will be described later with reference to FIG. 10 and the like.

The imager in accordance with the present embodiment is, for example, a three-dimensional camera, and is, more specifically, a stereo camera. The stereo camera includes a criterion camera and a reference camera. In the present embodiment, assume that an image captured by the criterion camera is referred to as a criterion image, an image captured by the reference camera is referred to as a reference image, and a pair of the criterion image and the reference image is referred to as a stereo image. A camera parameter of the criterion camera and a camera parameter of the reference camera are adjusted to be equal, and only a position at which the criterion camera captures an image and a position at which the criterion camera captures an image are different from each other. Additionally, an arrangement relationship between the criterion camera and the reference camera is designed so that an optical axis of the criterion camera and an optical axis of the reference camera are parallel with each other, and a criterion camera imaging plane and a criterion camera imaging plane are flush with each other and arrayed in a horizontal direction. Note that, since a slight misalignment in the arrangement relationship may occur in actual image-capturing, an image may be able to be corrected in consideration of the misalignment.

In the stereo camera, the criterion camera is arranged on one of the left side or the right side and the reference camera is arranged on the other side, whereby the image for the left eye and the image for the right eye are captured and the three-dimensional position information regarding the subject can be calculated based on the image for the left eye and the image for the right eye. In other words, the processor 100 calculates the three-dimensional position information based on the image for the left eye and the image for the right eye as endoscope images acquired by the endoscope 20. The following description will be given assuming that the criterion camera is for the left side and the reference camera is for the right side. In other words, the following description will be given assuming that the image for the left eye is the criterion image and the image for the right eye is the reference image.

A method of acquiring the three-dimensional position information with the stereo camera is omitted since it is well known. For example, assuming that a desired position of an imaging target object on a three-dimensional space is a position P, two-dimensional coordinates of a position P1 corresponding to the position P on the criterion image and two-dimensional coordinates of a position P2 corresponding to the position P on the reference image are not matched with each other and a misalignment occurs. This misalignment is referred to as parallax. Since three-dimensional coordinates of the position P are unknown, the parallax is also unknown.

The processor 100 then functions as the three-dimensional construction section 112. When acquiring a stereo image from the endoscope 20, the processor 100 searches the reference image for a pixel corresponding to a pixel at the position P1 on the criterion image, that is, a pixel at a point P2, and calculates parallax at a point P based on two-dimensional coordinates of the pixel at the position P1 and two-dimensional coordinates of the searched pixel at the point P2. A method regarding calculation of the parallax is referred to as stereo matching. In response to the determination of the parallax at the point P, the processor 100 then calculates three-dimensional coordinates of the point P using the principle of triangulation based on position information regarding the center of the criterion camera, position information regarding the center of the reference camera, position information regarding the point P1, and position information regarding the point P2. As the accuracy of search for the pixel at the position P2 becomes higher, the accuracy of calculation of the parallax becomes higher, which makes it possible to also obtain the three-dimensional coordinates of the position P with high accuracy. By repeating the above-mentioned calculation with respect to each pixel on the criterion image, it is possible to acquire depth information regarding the subject, and acquire three-dimensional position information regarding the subject.

As an algorithm regarding the stereo matching, various kinds of methods have been proposed. In the present embodiment, for example, it is possible to adopt a method of calculating parallax based on semi-global matching. However, the use of other algorithms is not prevented. Additionally, to implement these algorithms on the image processing device 10, it is sufficient if programing using a predetermined open source library is performed, and a program based on the programing is stored in the above-mentioned non-transitory information storage medium.

As a matter of descriptive convenience, X-, Y-, and Z-axes are illustrated in FIG. 3 as three axes that are orthogonal to each other. In the following description, terms of an "X-direction", a "Y-direction", and a "Z-direction" may be used. The "X-direction" is a direction along the X-axis and a direction in parallel with a lateral direction of the second display DP2. The "Y-direction" is a direction along the Y-axis and a direction in parallel with a vertical direction of the second display DP2. The "Z-direction" is a direction along the Z-axis and a direction in parallel with a depth direction of the second display DP2. Note that the "X-direction" may be referred to as a "horizontal direction". Note that, in a case where the stereo camera is used as the imager in the present embodiment, the criterion camera and the reference camera are arranged in the horizontal direction as described above. Thus, the X-direction can be also referred to as a "parallax direction".

The following description will be given of a processing example of the method in accordance with the present embodiment and a screen example in a case where the processing example is applied. Note that the screen example is described on the assumption of the above-mentioned endoscopic surgery, but the method in accordance with the present embodiment is not limited to the endoscopic surgery using the endoscope 20 as the rigid endoscope. For example, the endoscope system 1 in accordance with the present embodiment may be configured to include the endoscope 20 as a flexible endoscope and the image processing device 10. With this configuration, it is possible to use the method in accordance with the present embodiment with an aim to measure a distance from an inlet into which the endoscope 20 is inserted to a desired position, for example, in endoscopy.

FIG. 4 is a flowchart describing a processing example of the method in accordance with the present embodiment. The processor 100 performs processing of determining whether or not measurement has started (step S10). In a case of determining that the measurement has started (YES in step S10), the processor 100 performs position designation calculation processing (step S100) or subsequent processing. In a case of determining that the measurement has not started (NO in step S10), the processor 100 performs step S10 again.

The processing associated with step S10 can be implemented by various kinds of methods. For example, a predetermined button included in the endoscope 20 may be pushed by a user, a button included in a treatment tool may be pushed by the user, a button provided on an operation panel of the image processing device 10 may be pushed by the user, and a foot pedal connected with the image processing device 10 may be hit by the user. The operation panel and the foot pedal are not illustrated. Alternatively, the image processing device 10 may include a voice command device, and the processor 100 may be capable of determining YES in step S10 based on a predetermined voice. Alternatively, a memory, which is not illustrated, may include a gesture recognition program, and the processor 100 may be capable of determining YES in step S10 based on the gesture recognition program in response to the user's operation of a distal end portion of a treatment tool to perform a predetermined gesture. Alternatively, one treatment tool may be detected from the endoscope image, and the processor 100 may determine YES in step S10 at a timing at which the user touches a touch panel of the second display DP2 as described later. Alternatively, the processor 100 may determine YES in step S10 at a timing at which a plurality of treatment tools is detected from the endoscope image.

Thereafter, the processor 100 performs the position designation calculation processing (step S100), measurement processing (step S200), and display updating processing (step S300), and then performs processing of determining whether or not to end the measurement (step S400). In a case of determining not to end the measurement (NO in step S400), the processor 100 performs the position designation calculation processing (step S100) again. In a case where the processor 100 determines to end the measurement (NO in step S400), the flow ends. While details of the position designation calculation processing (step S100) and the measurement processing (step S200) will be described later, three-dimensional position information regarding the first measurement point 41 and the second measurement point 42 is calculated by the position designation calculation processing (step S100). The processor 100 then functions as the distance calculation section 120, and performs the measurement processing (step S200) to measure the distance between the first measurement point 41 and the second measurement point 42. The processor 100 then performs step S300 to display image data newly generated or updated by the position designation calculation processing (step S100) and the measurement processing (step S200) on the second display DP2.

The processor 100 then performs the position designation calculation processing (step S100), the measurement processing (step S200), and the display updating processing (step S300) at a timing of acquiring endoscope images for one frame period from the endoscope 20 until an event that causes the determination to be YES in step S400 occurs.

That is, in the present embodiment, the processor 100 continues the distance measurement until the event that causes the determination to be YES in step S400 occurs. Examples of the event that causes the determination to be YES in step S400 include pushing of a button to end a program regarding the measurement by the user and the elapse of predetermined time from a timing at which the determination is made as YES in step S10.

Figure 5:
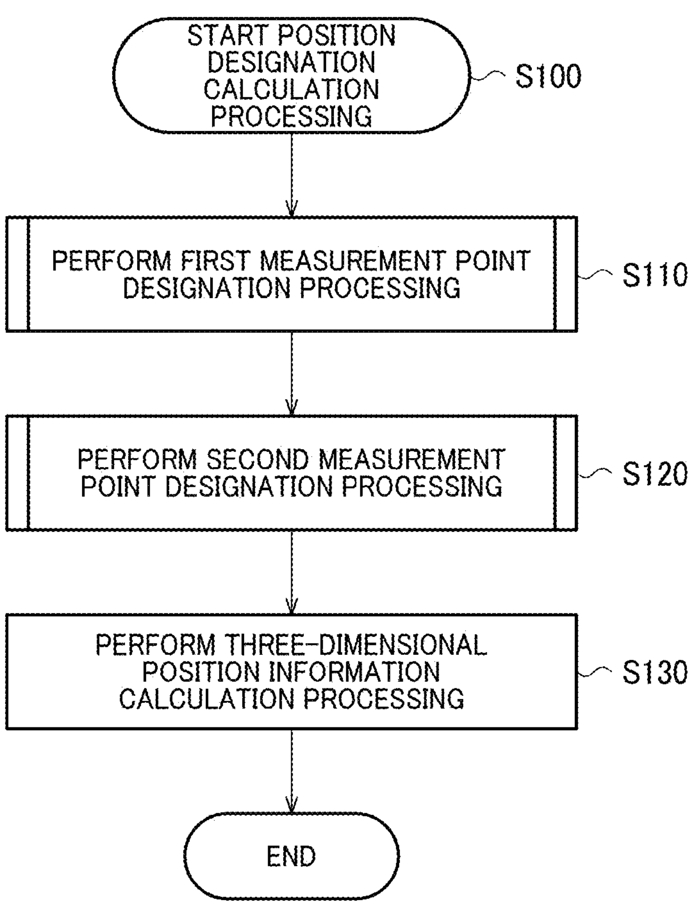
FIG. 5 is a flowchart describing a processing example of position designation calculation processing.

Details of the position designation calculation processing (step S100) will be described with reference to a flowchart in FIG. 5. Note that the position designation calculation processing (step S100) in FIG. 5 is processing of obtaining the first measurement point 41 using the above-mentioned first method and obtaining the second measurement point 42 using the above-mentioned second method. In FIG. 5, the processor 100 performs first measurement point designation processing (step S110) and second measurement point designation calculation processing (step S120), and thereafter performs the three-dimensional position information processing (step S130), and the flow ends.

Details of the first measurement point designation processing (step S110) are now described with reference to a flowchart in FIG. 6. The processor 100 performs processing of recognizing each treatment tool in an image (step S112), and thereafter performs processing of recognizing the distal end portion of each treatment tool (step S114). For example, since each treatment tool contains metal, the treatment tool has a luminance value that is higher than that of a tissue among subjects. In this regard, the processor 100 converts the endoscope image into a luminance image, detects pixels each having a luminance value that is higher than or equal to a predetermined threshold, groups the pixels by detecting contours of a gathering of the pixels, and detects a group of a predetermined or higher number of pixels, whereby step S112 can be implemented. Additionally, the processor 100 regards a distal end of the group of pixels detected in step S112 as the distal end of the treatment tool, whereby step S114 can be implemented. Note that steps S112 and S114 may be implemented by another method. For example, the treatment tool may be recognizable with use of a trained model that has been subjected to machine learning so as to enable image recognition with respect to the presence/absence of the treatment tool in the endoscope image. The trained model in this case is, for example, a convolution neural network (CNN) or the like. Additionally, since a position of the treatment tool in the Z-direction is located at a front side of a position of the tissue in the Z-direction in the endoscope image, it is possible to consider an image of a portion associated with the treatment tool as a foreground image and an image associated with a portion other than the treatment tool as a background image. Hence, processing of extracting a region associated with the treatment tool as the foreground image from the endoscope image and acquiring a treatment tool mask image, which is an image in which a region other than the region associated with the foreground image is masked, may be step S112. Note that a method of automatically generating a foreground mask image in response to designation of the region associated with the foreground image can be implemented by storage of a program using a known software library in the above-mentioned non-transitory information storage medium or the like.

Thereafter, the processor 100 performs processing of designating selected one distal end portion as the first measurement point 41 (step S116). In a case where a plurality of treatment tools is displayed on the second display DP2, the number of distal end portions of the treatment tools recognized by the processor 100 in step S114 is equal to the number of treatment tools displayed on the second display DP2. The processor 100 then functions as the measurement point selection section 114, and selects a distal end portion of a desired treatment tool as the first measurement point 41 in step S116. Step S116 may be, for example, notification processing of prompting selection of the distal end portion of the desired treatment tool or processing performed by the processor 100 to select a distal end portion of a predetermined treatment tool. The predetermined treatment tool is, for example, a treatment tool whose distal end portion have coordinates that are the closest to coordinates of the center of the second display DP2. Note that, in a case where the first measurement point designation processing (step S110) is performed when only one treatment tool is displayed on the second display DP2, step S116 may be omitted.

FIG. 7 is a flowchart describing a processing example of the second measurement point designation processing (step S120). The processor 100 designates the second measurement point 42 based on the portion designated by the user (step S122). For example, as described above, in a case where the second display DP2 functions as the touch panel, the user touches a desired position among subjects displayed on the second display DP2. A touch panel control circuit for the second display DP2 then outputs position information data based on the touched position to the processor 100. The processor 100 then performs processing of converting the position information data received from the touch panel control circuit into position information on the endoscope image. That is, the second measurement point 42 is at a subject position corresponding to a position, which is designated by the user, on the second display DP2.

Returning to FIG. 5, the three-dimensional position information calculation processing (step S130) is now described. As described above, the processor 100 performs, by following the algorithm of the stereo matching, three dimensional construction of the subject and calculation in the depth direction, and thereby calculates three-dimensional position information regarding the first measurement point 41 and the second measurement point 42. More specifically, for example, the processor 100 performs preprocessing such as re-size processing on the stereo image, and thereafter performs processing of parallelizing the stereo image. The processing of parallelizing the stereo image is performed with use of an intrinsic parameter and an extrinsic parameter, which have been preliminarily obtained. The intrinsic parameter corresponds to distortion due to a lens in the criterion camera or the reference camera, a focal length of a lens, a pixel pitch, or the like. The extrinsic parameter corresponds to a position and rotation amount of the reference camera with respect to the criterion camera. Additionally, in a case where the processor 100 has acquired the above-mentioned treatment tool mask image, the treatment tool mask image is distorted along with the processing of parallelizing the stereo image. Thus, the processor 100 may perform preprocessing on the treatment tool mask image before performing the stereo matching.

The processor 100 then performs the stereo matching using an algorithm such as semi-global block matching. This allows the processor 100 to calculate information regarding the depth direction based on the parallax and obtain the three-dimensional position information regarding the distal end portion of the first treatment tool 31 selected in step S116.

Details of the measurement processing (step S200) are now described with reference to a flowchart in FIG. 8. The processor 100 functions as the measurement execution determination section 122, and performs treatment tool stability determination processing (step S250). Thereafter, the processor 100 performs processing of measuring the distance between the first measurement point 41 and the second measurement point 42 (step S270). Details of the treatment tool stability determination processing (step S250) will be described later. In step S270, the processor 100 calculates the distance between the first measurement point 41 and the second measurement point 42 based on the three-dimensional position information regarding the first measurement point 41 and the three-dimensional position information regarding the second measurement point 42, each of which is calculated in step S130 in FIG. 6. The processor 100 then performs step S270, and thereafter performs processing of generating display data (step S290). The display data generated in step S290 is display data in which information regarding treatment tool stability obtained by the treatment tool stability determination processing (step S250) described later is iconized, display data in which information regarding the distance obtained by step S270 is iconized, or the like.

Figure 9:
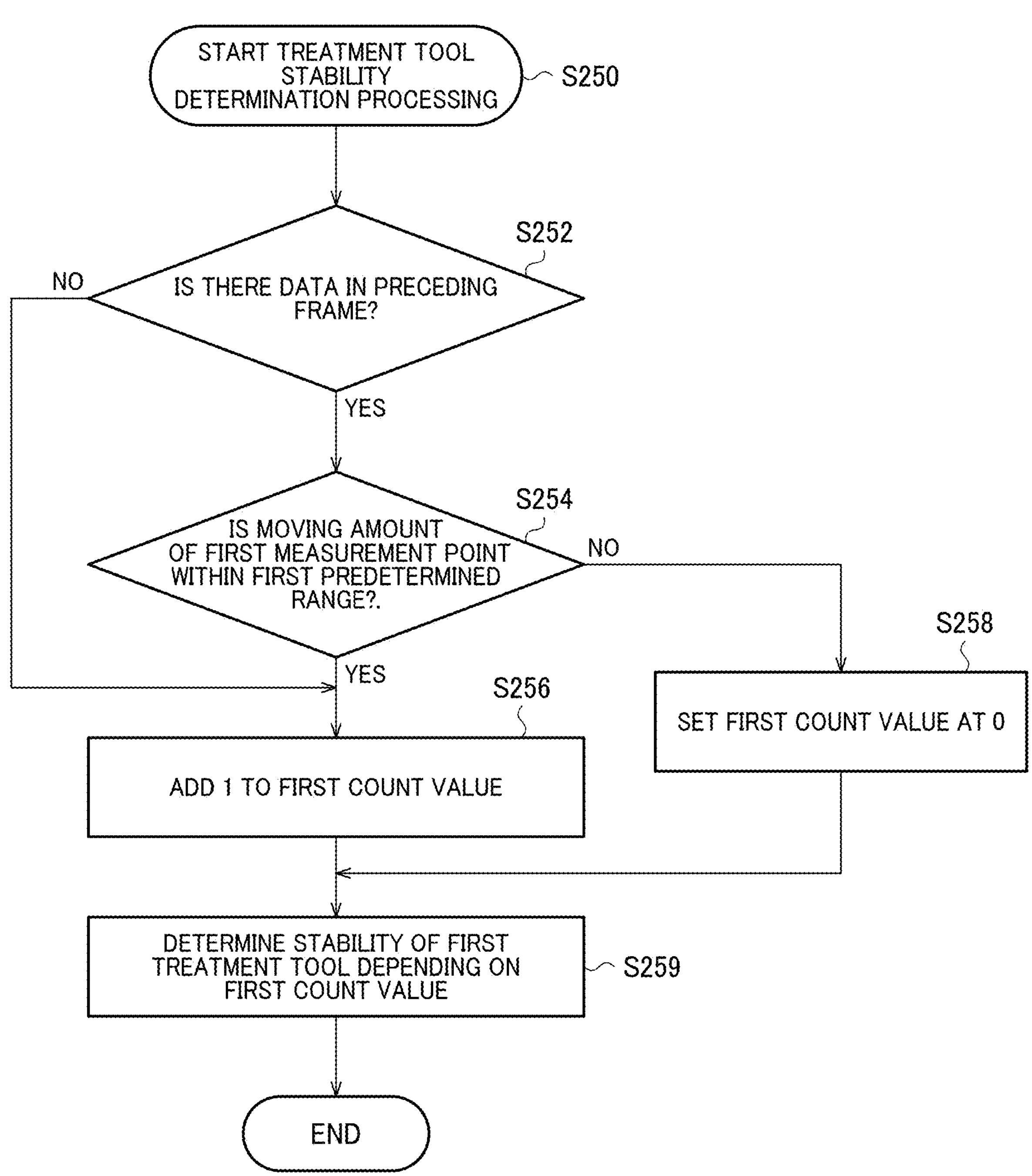
FIG. 9 is a flowchart describing a processing example of treatment tool stability determination processing.

Details of the treatment tool stability determination processing (step S250) will be described with reference to a flowchart in FIG. 9. The processor 100 performs processing of determining whether or not there is data in a preceding frame (step S252). In a case where there is the data in the preceding frame (YES in step S252), the processor 100 performs processing of determining whether or not a moving amount of the first measurement point 41 is within a first predetermined range (step S254). The moving amount of the first measurement point 41 mentioned herein corresponds to a distance between three-dimensional position coordinates of the first measurement point 41 in the preceding frame and three-dimensional position coordinates of the first measurement point 41 in the present frame. Since the first treatment tool 31 and the endoscope 20 are operated with the user's hands, there is a case where endoscope images are captured so that the distal end of the first treatment tool 31 is moving. To address this, the first predetermined range is set as a permissible range of displacement of the distal end position of the first treatment tool 31, and the processor 100 monitors whether or not the displacement that occurs along with updating of a frame is permissible in step S254. Note that the first predetermined range may be a permissible range of change in inclination of the first treatment tool 31 with respect to the horizontal direction.

In contrast, in a case where there is no data in the preceding frame (NO in step S252), the processor 100 performs processing of adding 1 to a first count value (step S256). Details of the first count value will be described later. The case where the determination is made as NO in step S252 is, in other words, a case where a frame is the first frame of endoscope images captured by the imager.

In a case of determining that the moving amount of the first measurement point 41 is within the first predetermined range (YES in step S254), the processor 100 then performs processing of adding 1 to the first count value (step S256).

In a case of also determining YES again in step S254, the processor 100 further adds 1 to the first count value. That is, in a case where the distal end position of the first treatment tool 31 is stable, the first count value cumulatively increases by addition as the number of frames of captured images increases. Additionally, a first predetermined value may be further set as an upper limit of the first count value. With this setting, in a case where the first count value is more than or equal to the first predetermined value, the user can determine that the distal end position of the first treatment tool 31 is stable to the extent that allows for determination that the accuracy of the measured distance between the first measurement point 41 and the second measurement point 42 is sufficiently high. Note that, in a case where the processor 100 determines YES in step S254 in a state where the first count value has reached the first predetermined value, step S256 may be processing of maintaining the first count value at the first predetermined value. More specifically, in a case where it is desirable that the distal end of the first treatment tool 31 be stable in a period of time obtained by multiplying one frame period by thirty frames, the first predetermined value is only required to be set at 30.

Note that, in the present embodiment, the period of time obtained by multiplying one frame period by the first predetermined value is referred to as a first predetermined period of time. That is, in a case where the distal end position of the first treatment tool 31 is stable for the first predetermined period of time, the user can determine that the accuracy of the measured distance between the first measurement point 41 and the second measurement point 42 is sufficiently high. That is, the first count value has a technical meaning as an index of a period of time in which the distal end position of the first treatment tool 31 continues to be stable.

Additionally, although illustration in a flowchart or the like is omitted, for example, the processor 100 may further perform processing of calculating a ratio of the first count value and the first predetermined value and storing the ratio in the treatment tool stability determination processing (step S250).

In contrast, in a case of determining that the moving amount of the first measurement point 41 is out of the first predetermined range (NO in step S254), the processor 100 performs processing of setting the first count value at 0 (step S258). Since the moving amount of the first measurement point 41 being out of the first predetermined range means that the distal end position of the first treatment tool 31 is not stable, it is thought to take a certain period of time until the distal end position of the first treatment tool 31 becomes stable again, and thus the first count value is set at 0.

Note that the processing in a case where the determination is made as NO in step S254 is not limited thereto, and may be changeable as appropriate by the user. For example, the processor 100 may subtract a predetermined number from the first count value in step S258, or may perform step S259, which will be described later, without performing addition or subtraction to/from the first count value. For example, in a case where the distal end of the first treatment tool 31 is stable but the result is NO in step S254 due to temporary occurrence of noise, it is thought that there is no need for setting the first count value at 0.

The processor 100 then performs step S256 or step S258, and thereafter performs processing of determining stability of the first treatment tool 31 depending on the first count value (step S259). For example, the processor 100 presents a ratio of the first count value accumulated at a point of time in step S259 to a target value, and determines whether or not the distal end position of the first treatment tool 31 is stable.

FIG. 10 illustrates a screen example of the second display DP2 to which the method in accordance with the present embodiment is applied. The processor 100 displays, based on the endoscope images captured by the imager of the endoscope 20, a screen indicated by A10, an icon indicated by A13, an icon indicated by A14, and an icon indicated by A15 on the second display DP2.

On the screen indicated by A10 in FIG. 10, the first treatment tool 31 is recognized and the distal end of the first treatment tool 31 is displayed as the first measurement point 41 as a result of the above-mentioned first measurement point designation processing (step S110). While only the first treatment tool 31 associated with the first measurement point 41 selected by the above-mentioned step S116 is displayed for the sake of convenience in FIG. 10, a treatment tool other than the first treatment tool 31 may be displayed on the screen indicated by A10. The same applies to screen examples in FIGS. 11, 14, 17, 18, 19, 22, 23, 25, 30, 36, and 37, which will be described later.

The icon indicated by A13 represents a ratio of a period of time in which the treatment tool is determined to be stable to a period of time in which it is desirable that the treatment tool be stable. In other words, the ratio between the first count value accumulated in step S256 and the first predetermined value is displayed with a graph icon. Note that a mode of the icon indicated by A13 is not limited thereto, and details will be described later.

The icon indicated by A14 is a character icon regarding a stable state of the distance measurement, and is, in other words, a character icon regarding the stability of the treatment tool. The icon indicated by A15 is a symbol icon representing a degree of stability in a simple manner. Note that a mode of the icon indicated by A15 is not limited thereto, and details will be described later with reference to FIG. 12.

In the screen example illustrated in FIG. 10, the icon indicated by A13 represents the ratio of the first count value to the first predetermined value being insufficient as a period of time that allows for determination that the treatment tool is stable. The icons indicated by A14 and A15 represent the treatment tool being not stable in a simple manner.

Meanwhile, the user uses the touch panel function of the second display DP2 to designate the second measurement point 42. A distance information icon indicated by A11 and an arrow icon indicated by A12 are then displayed based on a result of the measurement performed in step S270 in FIG. 8. That is, the processor 100 generates the icons indicated by A11, A12, A13, A14, and A15, the icon representing the first measurement point 41, and the icon representing the second measurement point 42 in step S290 in FIG. 8. The processor 100 then displays these icons, together with the endoscope image, on the second display DP2 in step S300.

The distance information icon indicated by A11 is configured not to include unit information in the present embodiment, but, for example, the icon may be displayable by including a specific unit such as "100 mm", or a display mode including a unit and a display mode not including the unit may be switchable. Additionally, for example, a table regarding a unit of length and conversion of the unit is stored in the memory, which is not illustrated, and the user selects the unit of length, whereby the distance information icon indicated by A11 may be changeable to an icon based on a number corresponding to the selected unit.

Additionally, the icon representing the first measurement point 41 and the icon representing the second measurement point 42 are superimposed on the screen indicated by A10 and displayed on the second display DP2 for explanatory convenience, but are not necessarily displayed. It is sufficient if the user makes determination about this as appropriate. Note that in FIG. 10, the distal end position of the first treatment tool 31 and a display position of the icon representing the first measurement point 41 are shifted for the sake of convenience. The same applies to FIGS. 11, 14, 17, 18, 19, 22, 23, 25, 29A, 36, and 37, which will be described later.

Additionally, in FIG. 10, the arrow icon indicated by A12 is not necessarily displayed. It is sufficient if the user makes determination about this as appropriate. The same applies to FIGS. 11, 14, 22, 23, 36, and 37, which will be described later.

Additionally, a dotted line frame indicated by A16 is a frame representing the first treatment tool 31 being recognized in image processing, and may be displayed on the second display DP2 so as to supplementarily represent the first treatment tool 31 being recognized, but is not necessarily displayed. The description and illustration of the dotted line frame may be omitted below as appropriate.

Figure 11:
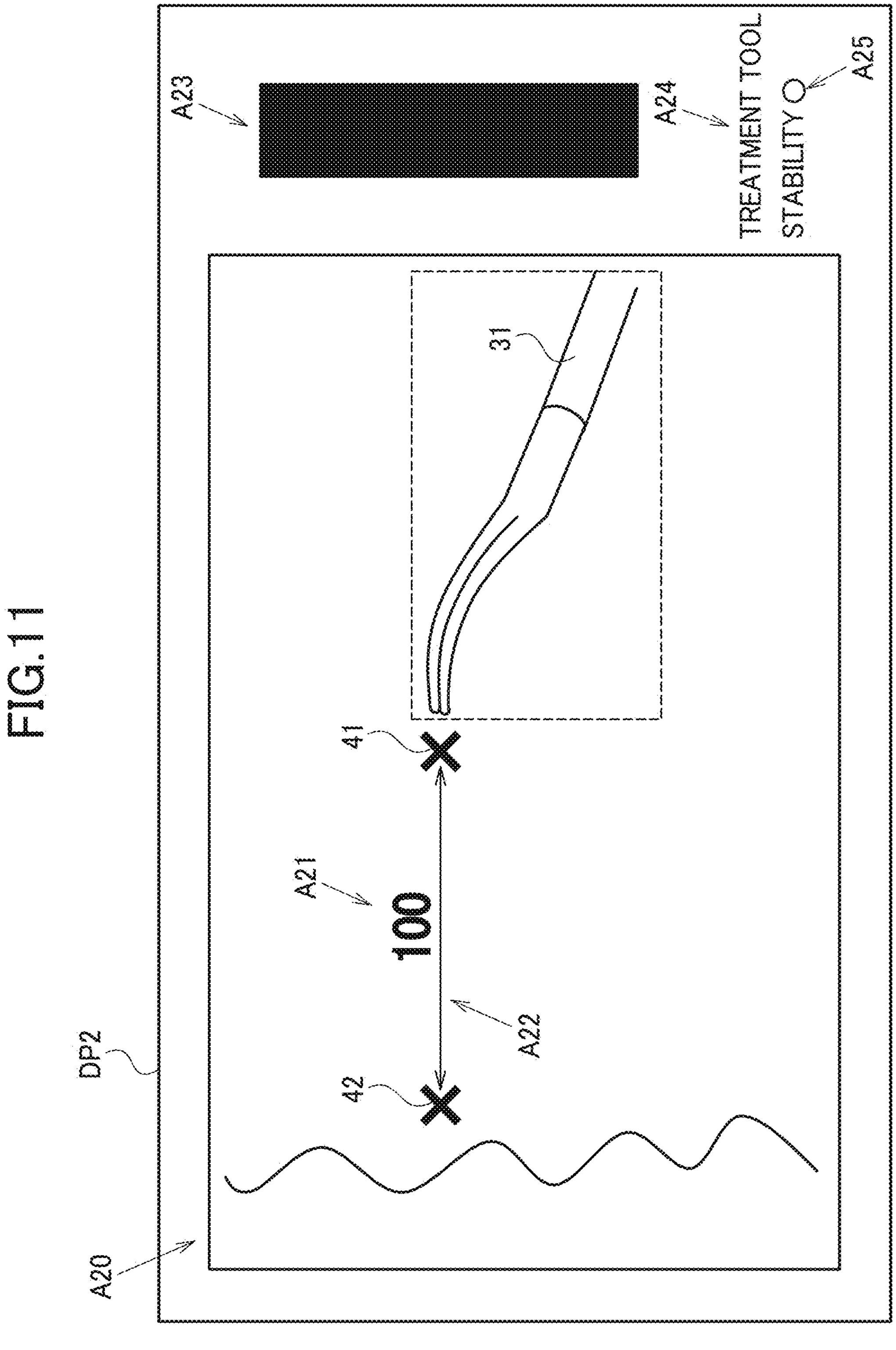
FIG. 11 is a view for describing a screen example in a case where the treatment tool is stabilized.

FIG. 11 illustrates another screen example of the second display DP2 to which the method in accordance with the present embodiment is applied. Similarly to FIG. 10, in addition to a screen indicated by A20, a graph indicated by A23 and a character icon indicated by A24 are displayed on the second display DP2. The character icon indicated by A24 includes a character icon indicated by A25. In addition, similarly to the case in FIG. 10, the first treatment tool 31 is recognized and the distal end of the first treatment tool 31 is displayed as the first measurement point 41 as a result of the above-mentioned first measurement point designation processing (step S110). Meanwhile, the user touches the second display DP2 as the touch panel, whereby the second measurement point 42 is designated. A distance information icon indicated by A21 and an arrow icon indicated by A22 are displayed based on a result of the measurement performed in step S270 in FIG. 8.

While FIG. 10 illustrates the screen example in the case where the stability of the treatment tool is insufficient, FIG. 11 illustrates a screen example in which the stability of the treatment tool is sufficient. Hence, there are differences in various kinds of icons displayed on the second display DP2. For example, the icon indicated by A23 represents the ratio of the first count value to the first predetermined value being sufficient as a period of time that allows for determination that the treatment tool is stable. The icons indicated by A24 and A25 represent the treatment tool being stable in a simple manner. The distance information icon indicated by A11 in FIG. 10 and the distance information icon indicated by A21 in FIG. 11 are also different in display modes, which will be described in detail later with reference to FIG. 16.

Note that the symbol icon representing stability of the treatment tool is not limited to the modes indicated by A15 in FIGS. 10 and A25 in FIG. 11, and can be modified in various manners. For example, as illustrated in FIG. 12, mode patterns regarding the stability of the treatment tool corresponding to the stability of the treatment tool are stored in the memory, which is not illustrated, and a mode pattern may be selectable in accordance with required stability of the treatment tool. The stability of the treatment tool in FIG. 12 corresponds to, for example, the ratio of the first count value to the first predetermined value.

For example, assume that the first predetermined value is set at 30. In a case where the processor 100 determines YES thirtieth-consecutive times in a row in step S254, the stability of the treatment tool is at 100%. Additionally, in a case where the processor 100 determines YES eighteenth-consecutive times in a row in step S254, the stability of the treatment tool is at 60%.

For example, if an error in the measured distance is permitted to some extent, there is a case where no problem occurs if a distance measurement value at the time of the stability of the treatment tool exceeding 60% is used. In this case, for example, with use of a pattern P-A1 in FIG. 12, modes of a degree of stability of the treatment tool may be classified into a case where the degree of stability of the treatment tool is 100%, a case where the degree of stability of the treatment tool is 80% or more and less than 100%, a case where the degree of stability of the treatment tool is 60% or more and less than 80%, and a case where the degree of stability of the treatment tool is 0% or more and less than 60%. Note that the notation of "80% to 100%" in FIG. 12 means "80% or more and less than 100%", and the same applies to the other notation. Additionally, for example, in a case where there is no need of distinguishing whether or not the degree of stability of the treatment tool is 100%, a pattern P-A2 in FIG. 12 may be used. The pattern P-A2 is different from the pattern P-A1 in employing an identical display mode in the case where the degree of stability of the treatment tool is 100% and the case where the degree of stability of the treatment tool is 80% or more and less than 100%.

Additionally, for example, in a case where a measured distance is desired to be grasped as accurately as possible, it is preferable that the degree of stability of the treatment tool reach 100%. In this case, for example, a mode pattern like a pattern P-A3 in FIG. 12 may be used. The pattern P-A3 is a mode pattern including two modes: a mode in the case where the degree of stability of the treatment tool is 100% and a mode in other cases. Additionally, the pattern P-A3 represents the degree of stability of the treatment tool in a symbol mode, but may represent the degree of stability of the treatment tool, for example, in a character mode as represented by a pattern P-A4. This allows the user to easily grasp the degree of stability of the treatment tool.

Figure 13:
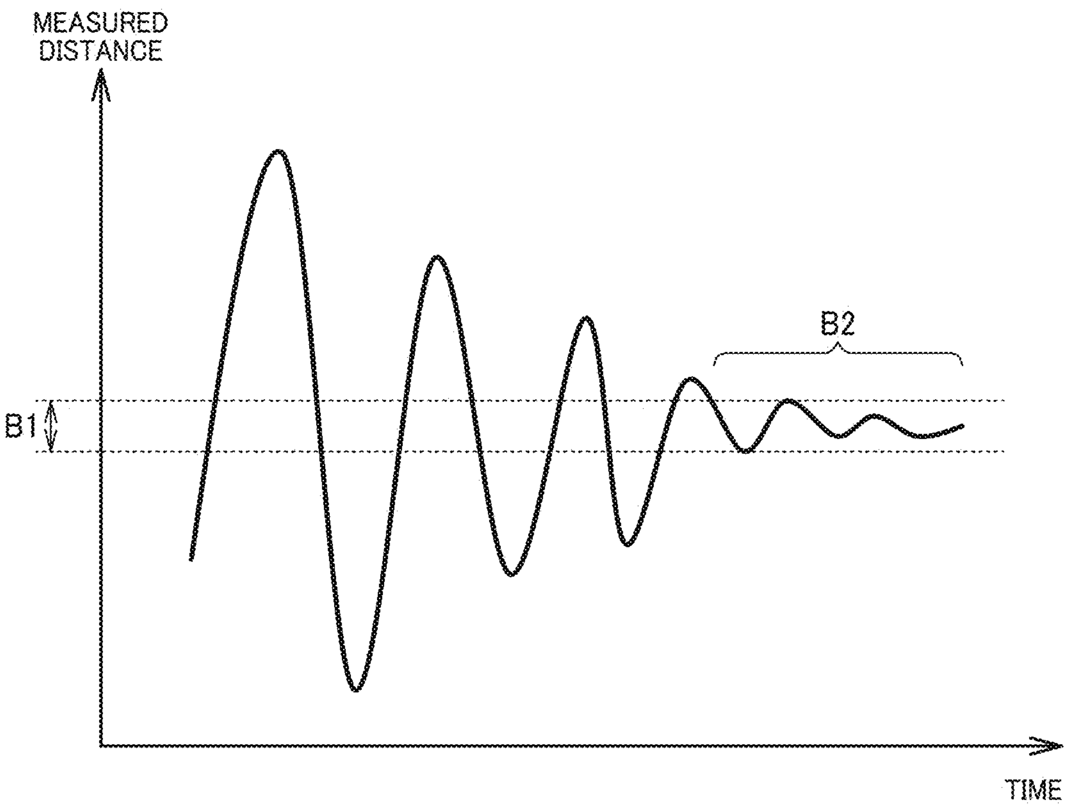
FIG. 13 is a chart for describing an example of displaying a measured distance as time-series data.

Additionally, although illustration in the flowchart is omitted, for example, the processor 100 may store the measured distances as time-series data in the memory, which is not illustrated, and perform processing of displaying change in measured distance over time as a graph illustrated in FIG. 13. An ordinate axis of the graph in FIG. 13 represents the distance information measured in step S270 in FIG. 8, and an abscissa axis of the graph in FIG. 13 represents time.

For example, the second display DP2 has the touch panel function, and in a case where the user designates the second measurement point 42 using the touch panel function, it is possible to quantitatively grasp the stability of the distal end of the first treatment tool 31 from the graph illustrated in FIG. 13. That is, in a case where the second measurement point 42 is designated in step S122 in FIG. 7, a subject associated with the second measurement point 42 can be handled as being stationary. As a result, the behavior of the graph in FIG. 13 is thought to be dependent on the stability of the distal end of the first treatment tool 31 operated by the user. For example, since the behavior of the distal end of the first treatment tool 31 becomes more stable as the user, after starting an operation of the first treatment tool 31, gets used to the operation of the first treatment tool 31, a fluctuation width of the measured distance becomes narrower over time.

Figure 8:
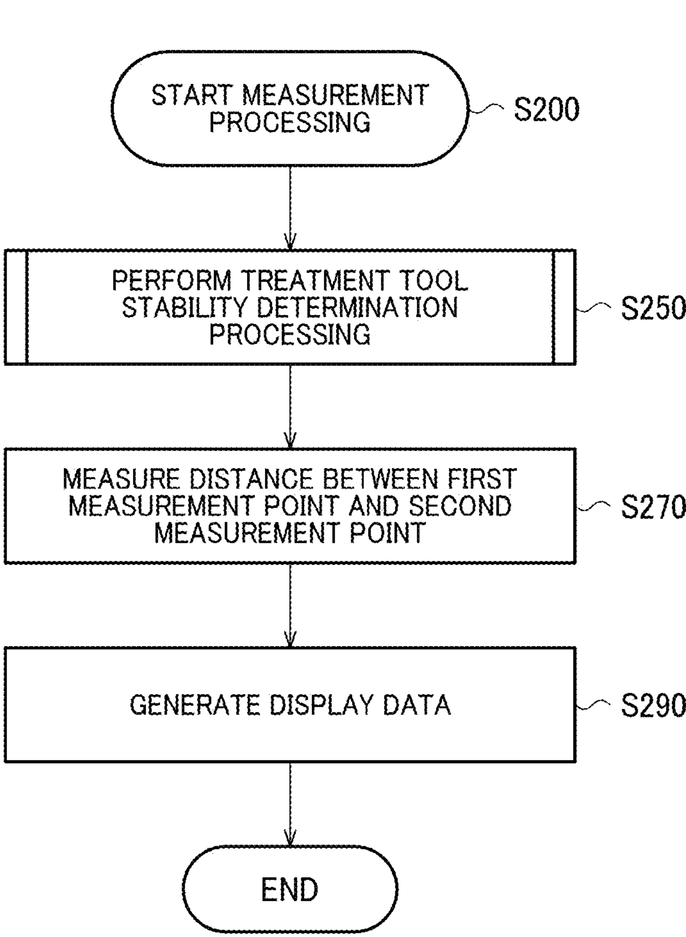
FIG. 8 is a flowchart describing a processing example of measurement processing.

Hence, for example, in a case where the change amount of the measured distance falls within a second predetermined range in the measurement processing (step S200) in FIG. 8 during a second predetermined period of time, the processor 100 may perform processing of determining that the distance measurement is stable. Specifically, for example, a width indicated by B1 in FIG. 13 corresponds to the second predetermined range, and a width indicated by B2 corresponds to the second predetermined period of time.

Figure 14:
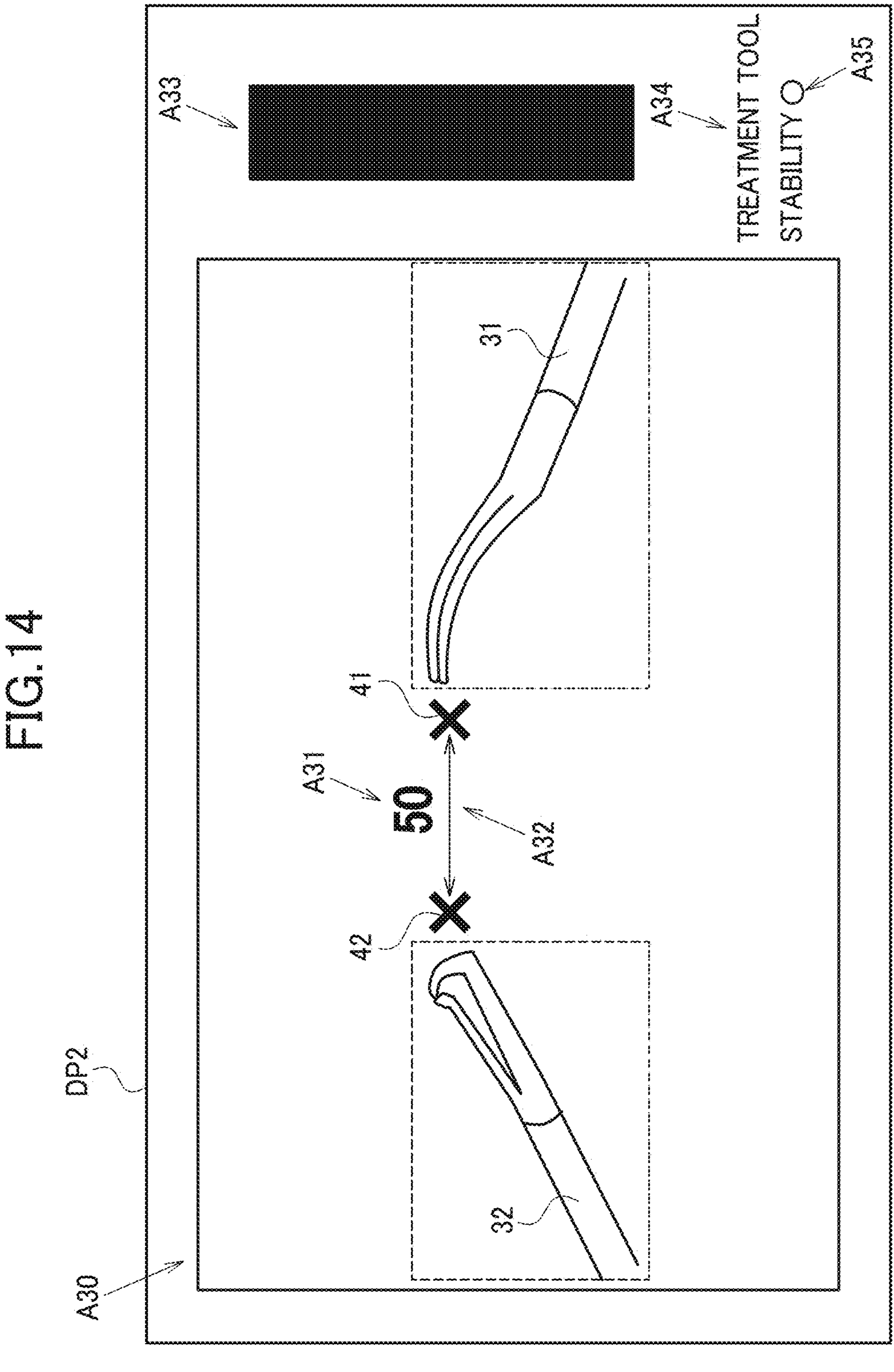
FIG. 14 is a view for describing a screen example in a case where a distance is measured with two treatment tools.

Additionally, as described above, since it is also possible to obtain the position information regarding the first measurement point 41 and the position information regarding the second measurement point 42 using only the first method, a screen example of the second display DP2 to which the method in accordance with the present embodiment is applied can be a screen example as illustrated in FIG. 14. In FIG. 14, in addition to a screen indicated by A30, an icon indicated by A33, an icon indicated by A34, and an icon indicated by A35 are displayed on the second display DP2. The icons indicated by A31, A32, A33, A34, and A35 in FIG. 14 correspond to the icons indicated by A21, A22, A23, A24, and A25 in FIG. 11. Meanwhile, the screen indicated by A30 in FIG. 14 is different from the screen example indicated by A20 in FIG. 11 in that the position information regarding the distal end of the second treatment tool 32 serves as the position information regarding the second measurement point 42.

For example, although illustration in the flowchart is omitted, the processor 100 executes step S110 in a state where at least the first treatment tool 31 and the second treatment tool 32 are seen in the imager of the endoscope 20. In step S112, the processor 100 then recognizes the first treatment tool 31 and the second treatment tool 32. The processor 100 then recognizes the distal end portion of the first treatment tool 31 and the distal end portion of the second treatment tool 32 in step S114. The processor 100 then designates the distal end portion of the first treatment tool 31 as the first measurement point 41 and the distal end portion of the second treatment tool 32 as the second measurement point 42 in step S116. This step enables designation of the second measurement point 42 in substitution for step S120. The processor 100 further performs steps S130, S200, and S300, whereby display of the screen example in FIG. 14 can be implemented.

Additionally, in a case where the position information regarding the distal end of the second treatment tool 32 serves as the position information regarding the second measurement point 42 as illustrated in FIG. 14, the processor 100 may further determine the stability of the distal end of the second treatment tool 32. In other words, the treatment tool stability determination processing (step S250) in FIG. 9 may be applied to both the first measurement point 41 and the second measurement point 42.

Although the illustration is omitted, for example, the icons indicated by A13, A14, and A15 in FIG. 10 may be displayed with respect to each of the first measurement point 41 and the second measurement point 42. Alternatively, the icons indicated by A13, A14, and A15 in FIG. 10 may be displayed so that one of the first measurement point 41 and the second measurement point 42 having a lower degree of stability of the treatment tool is prioritized over the other.

As described above, the image processing device 10 in accordance with the present embodiment includes the processor 100 that performs display processing on the display DP. The processor 100 uses an endoscope image of a subject acquired by the endoscope 20 to calculate three-dimensional position information regarding the first treatment tool 31 and a predetermined portion (first portion) in the endoscope image (step S100), Additionally, the processor 100 measures the distance between the first measurement point 41 at the distal end side of the first treatment tool 31 and the second measurement point 42 associated with the predetermined portion based on the three-dimensional position information regarding the first treatment tool 31 and the predetermined portion (step S200), and performs processing of displaying whether or not the distance measurement is in the stable state on the display DP (second display DP2) (step S300).

In this manner, the processor 100 included in the image processing device 10 in accordance with the present embodiment is capable of calculating the three-dimensional position information regarding the first measurement point 41 and the second measurement point 42 in the endoscope image acquired from the endoscope 20. Additionally, since the processing of displaying whether or not the measurement of the distance between the first measurement point 41 and the second measurement point 42 is in the stable state is performed, the user is able to easily determine whether or not the distance can be stably measured from the display DP. This allows the user to perform a treatment based on the appropriately measured distance.

For example, since the endoscope 20 and the first treatment tool 31 are operated by the user's hands or the like in the endoscopic surgery as described above, there is a possibility that a variation in position information regarding the distal end of the first treatment tool 31 increases. Similarly, there is a possibility for higher influence of blurring of images due to hand movement on the imager of the endoscope 20. In this regard, the application of the method in accordance with the present embodiment allows the user to grasp whether or not the distance measurement is stable, and thereby allows the user to perform a manipulation using a distance when the distance measurement is stable. This allows the user to perform a more appropriate treatment. For example, in a case where a surgical margin regarding partial resection of a malignant tumor is evaluated, distance information regarding the measured surgical margin has a significant meaning.

The above-mentioned U.S. Unexamined Patent Application Publication No. 2010/0317965 discloses the method of displaying a measured value obtained by measurement of a distance between points designated by a distal end of a robot tool used in surgery, but does not propose the method of displaying information regarding whether or not the distance measurement is stable.

Additionally, the method in accordance with the present embodiment may be implemented as the endoscope system 1. That is, the endoscope system 1 in accordance with the present embodiment includes the image processing device 10 and the endoscope 20. With this configuration, it is possible to obtain an effect that is similar to the above-mentioned effect.

Alternatively, the method in accordance with the present embodiment may be implemented as a processing method. That is, the processing method in accordance with the present embodiment causes a computer to execute processing of displaying an endoscope image of a subject acquired by the endoscope 20 on the display DP and processing of using the endoscope image of the subject to calculate three-dimensional position information regarding the first treatment tool 31 and the predetermined portion in the endoscope image. Additionally, the processing method in accordance with the present embodiment causes the computer to further perform processing of measuring the distance between the first measurement point 41 at the distal end side of the first treatment tool 31 and the second measurement point 42 associated with the predetermined portion based on the three-dimensional position information regarding the first treatment tool 31 and the predetermined portion, and processing of displaying whether or not the distance measurement is in the stable state. With this configuration, it is possible to obtain an effect that is similar to the above-mentioned effect.

Additionally, the method in accordance with the present embodiment may be implemented as a non-transitory information storage medium. That is, the non-transitory information storage medium in accordance with the present embodiment stores a program that causes the computer to execute the processing of displaying the endoscope image of the subject acquired by the endoscope 20 on the display DP and the processing of using the endoscope image of the subject to calculate the three-dimensional position information regarding the first treatment tool 31 and the predetermined portion in the endoscope image. Additionally, the non-transitory information storage medium in accordance with the present embodiment further stores a program that causes the computer to execute the processing of measuring the distance between the first measurement point 41 at the distal end side of the first treatment tool 31 and the second measurement point 42 associated with the predetermined portion based on the three-dimensional position information regarding the first treatment tool 31 and the predetermined portion, and the processing of displaying whether or not the distance measurement is in the stable state. With this configuration, it is possible to obtain an effect that is similar to the above-mentioned effect.

Additionally, the processor 100 may calculate the three-dimensional position information based on the image for the left eye and the image for the right eye as endoscope images acquired by the endoscope 20. With this configuration, it is possible to construct the image processing device 10 capable of determining whether or not the distance measured using the position information regarding the first measurement point 41 and the position information regarding the second measurement point 42 is in the stable state. Each position information is obtained by the stereo matching.

Additionally, the three-dimensional position information regarding the predetermined portion may be three-dimensional position information regarding the second treatment tool 32. Furthermore, the processor 100 may measure the distance between the first measurement point 41 at the distal end side of the first treatment tool 31 and the second measurement point 42 on the distal end side of the second treatment tool 32 based on the three-dimensional position information regarding the first treatment tool 31 and the predetermined portion. With this configuration, it is possible to construct the image processing device 10 capable of determining whether or not the distance measurement using the distal end position of the first treatment tool 31 and the distal end position of the second treatment tool 32 is in the stable state.

Additionally, the three-dimensional position information regarding the predetermined portion may include three-dimensional position information regarding the second measurement point 42, which is designated by the user and is at a subject position corresponding to a position on the display DP (second display DP2). Furthermore, the processor 100 may measure the distance between the first measurement point 41 at the distal end side of the first treatment tool 31 and the second measurement point 42 based on the three-dimensional position information regarding the first treatment tool 31 and the predetermined portion. With this configuration, it is possible to construct the image processing device 10 capable of determining whether or not the distance measurement using the distal end position of the first treatment tool 31 and the position designated by the user is in the stable state.

Furthermore, in a case where the first measurement point 41 and the second measurement point 42 are stably measured for a predetermined period of time or in a case where the distance measurement is in the stable state for a predetermined period of time, the processor 100 may determine that the distance measurement is in the stable state. With this configuration, it is possible to construct the image processing device 10 that quantifies the stability of the distance measurement depending on a period of time.

Additionally, in a case where at least the moving amount of the first measurement point 41 is within the first predetermined range in the first predetermined period of time, the processor 100 may determine that the distance measurement is in the stable state. With this configuration, it is possible to construct a determination criterion regarding the stability of the distance measurement using the calculated position information regarding the first measurement point 41.

Additionally, in a case where the change amount of the distance is within the second predetermined range in the second predetermined period of time, the processor 100 may determine that the distance measurement is in the stable state. With this configuration, it is possible to construct a determination criterion regarding the stability of the distance measurement using the measured distance information.

The method in accordance with the present embodiment is not limited to the above-mentioned method, and can be modified in various manners. For example, a display mode of an icon representing a period of time in which the treatment tool is determined as stable can be modified in various manners. For example, the display mode may be, other than a bar graph-type icon indicated by B11 in FIG. 15, a circle graph-type icon indicated by B12, or a meter display-type icon indicated by B13. Additionally, the meter display-type icon indicated by B13 may further include an icon representing a ratio of the first count value to the first predetermined value as indicated by B14. Additionally, the display mode is not limited to the graph-type icon, and may be, for example, a fraction display-type icon indicated by B15. Note that, for example, a denominator indicated by B16 corresponds to the first predetermined value, and a numerator indicated by B17 corresponds to the first count value. This allows the user to easily determine the ratio of the period of time in which the treatment tool is determined as stable to the period of time in which it is desirable that the treatment tool be stable.

Additionally, the display mode of the measured distance information is not limited to the modes indicated by A11 in FIGS. 10 and A21 in FIG. 12, and can be modified in various manners. For example, as illustrated in FIG. 16, display mode patterns of the measured distance information are stored in the memory, which is not illustrated, and a display mode pattern may be selectable by the user.

In a pattern P-B1 in FIG. 16, a display mode in a case where the treatment tool is not stable is a mode in which a measured number indicated by B21 is iconized and a symbol-type icon indicated by B22 is added to the icon indicated by B21. Additionally, in the pattern P-B1, a display mode in a case where the treatment tool is stable is a mode in which a measured number indicated by B23 is iconized. By seeing the symbol-type icon indicated by B22, the user can grasp that the treatment tool is not stable. Alternatively, by making comparison between the icon indicated by B21 and the icon indicated by B23, the icon indicated by B23 is displayed in boldface. This can make visibility of the icon indicated by B23 higher than visibility of the icon indicated by B21, and can thereby suggest to the user that the treatment tool is stable. Similarly, in a pattern P-B2 in FIG. 16, an icon displayed in a case where the treatment tool is stable is displayed in a darker color than a color of an icon displayed in a case where the treatment tool is not stable, whereby it is possible to suggest to the user that the treatment tool is stable. Additionally, a pattern P-B3 in FIG. 16 is a display mode pattern in which an icon used in the pattern P-B1 is combined with a graph icon. A graph icon indicated by B24 represents that the treatment tool is not stable, and a graph icon indicated by B25 represents that the treatment tool is stable. Additionally, a pattern P-B4 is different from the pattern P-B1 in that distance information is not displayed in a case where the treatment tool is not stable.

In this manner, in the image processing device 10 in accordance with the present embodiment, the processor 100 changes a display mode of a measured distance value depending on whether or not the distance measurement is in the stable state. This allows the user to easily determine whether or not the distance measurement is stable.

Additionally, the processor 100 may display a period of time in which the distance measurement is in the stable state with a graph. This allows the user to visually grasp the stability of the distance measurement.

Figure 17:
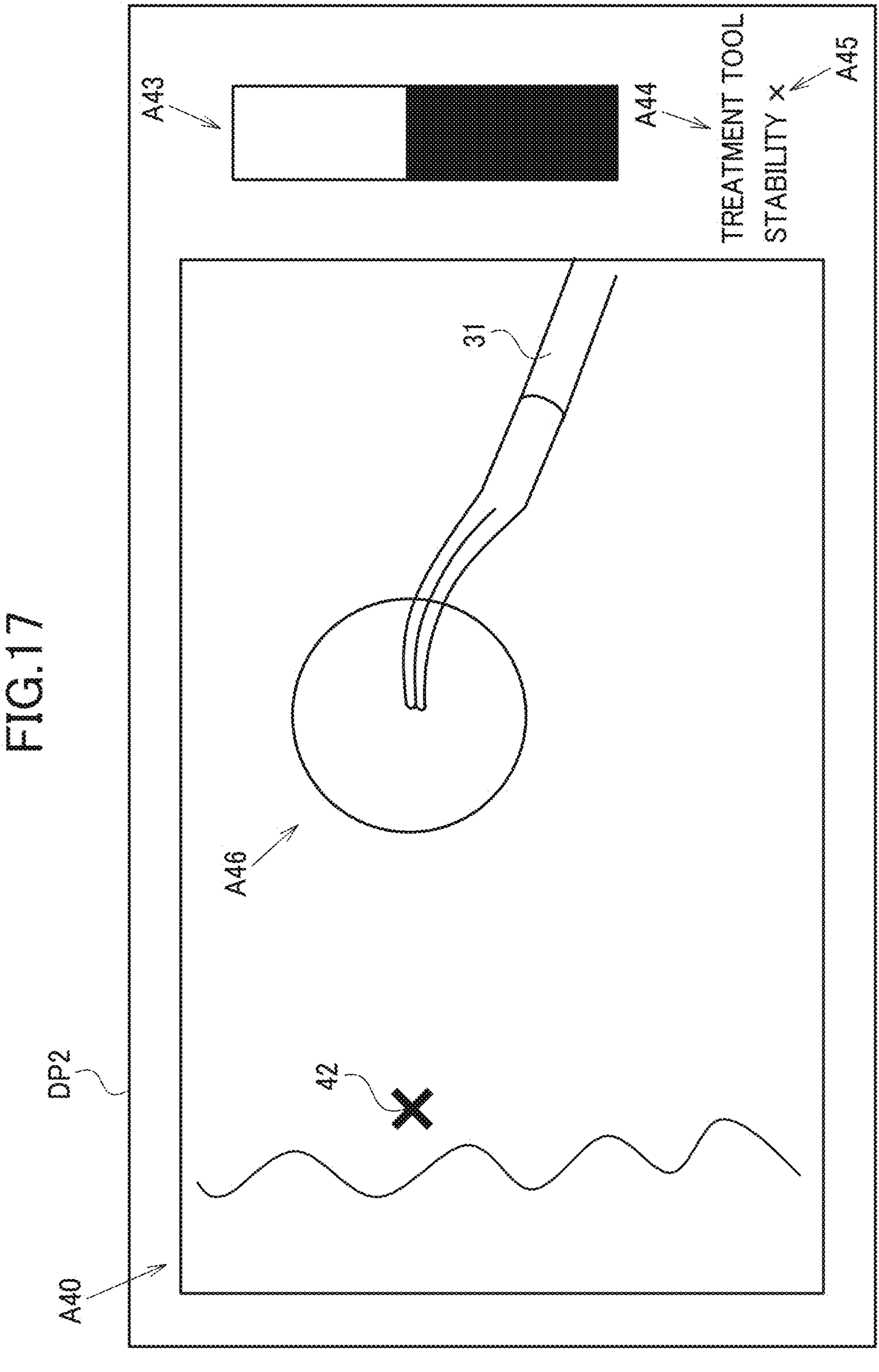
FIG. 17 is a view for describing a screen example including an image indicating a range in which a distal end of a first treatment tool is stable.

Additionally, for example, in a case where the stability of the treatment tool is insufficient, the processor 100 may perform processing of displaying a screen example illustrated in FIG. 17 on the second display DP2. In FIG. 17, a screen indicated by A40, an icon indicated by A43, an icon indicated by A44, and an icon indicated by A45 are displayed on the second display DP2. Additionally, in addition to the first treatment tool 31, an icon indicated by A46 is displayed on the screen indicated by A40. The icon indicated by A46 is an icon that suggests to the user at which position the distal end of the first treatment tool 31 should be located to stabilize the distal end of the first treatment tool 31. Note that the icons indicated by A43, A44, and A45 in FIG. 17 correspond to the icons indicated by A13, A14, and A15 in FIG. 10. Additionally, in FIG. 17, as a display mode of the distance information icon, the pattern P-B4 in FIG. 16 is used. That is, since the stability of the treatment tool is insufficient, the icon associated with the measured distance information is not displayed on the second display DP2 in FIG. 17.

For example, although illustration in a flowchart or the like is omitted, in a case where the determination is made as YES in step S254, the processor 100 may perform, in addition to step S256, processing of storing predetermined data in the memory, which is not illustrated. The predetermined data is, for example, position information regarding the distal end of the first treatment tool 31 associated with a frame with which the determination is made as YES in step S254. The processor 100 then searches information regarding previous frames stored in the memory for a frame including the predetermined data, and performs, based on the predetermined data in the searched frame, processing of generating aggregation information of position information regarding the distal end of the first treatment tool 31.

The processor 100 then performs processing of generating predetermined graphic image data based on the aggregation information in step S290. The predetermined graphic image data can be said as image information to make the moving amount of the first measurement point 41 within the first predetermined range.

The processor 100 then performs step S300 to perform display processing so as to superimpose the icon indicated by A46 in FIG. 17 on the image indicated by A40 in FIG. 17. Note that the icon indicated by A46 is a circular shaped icon, but may be an icon having another graphic pattern, such as an ellipse shape and a polygon shape.

Figure 18:
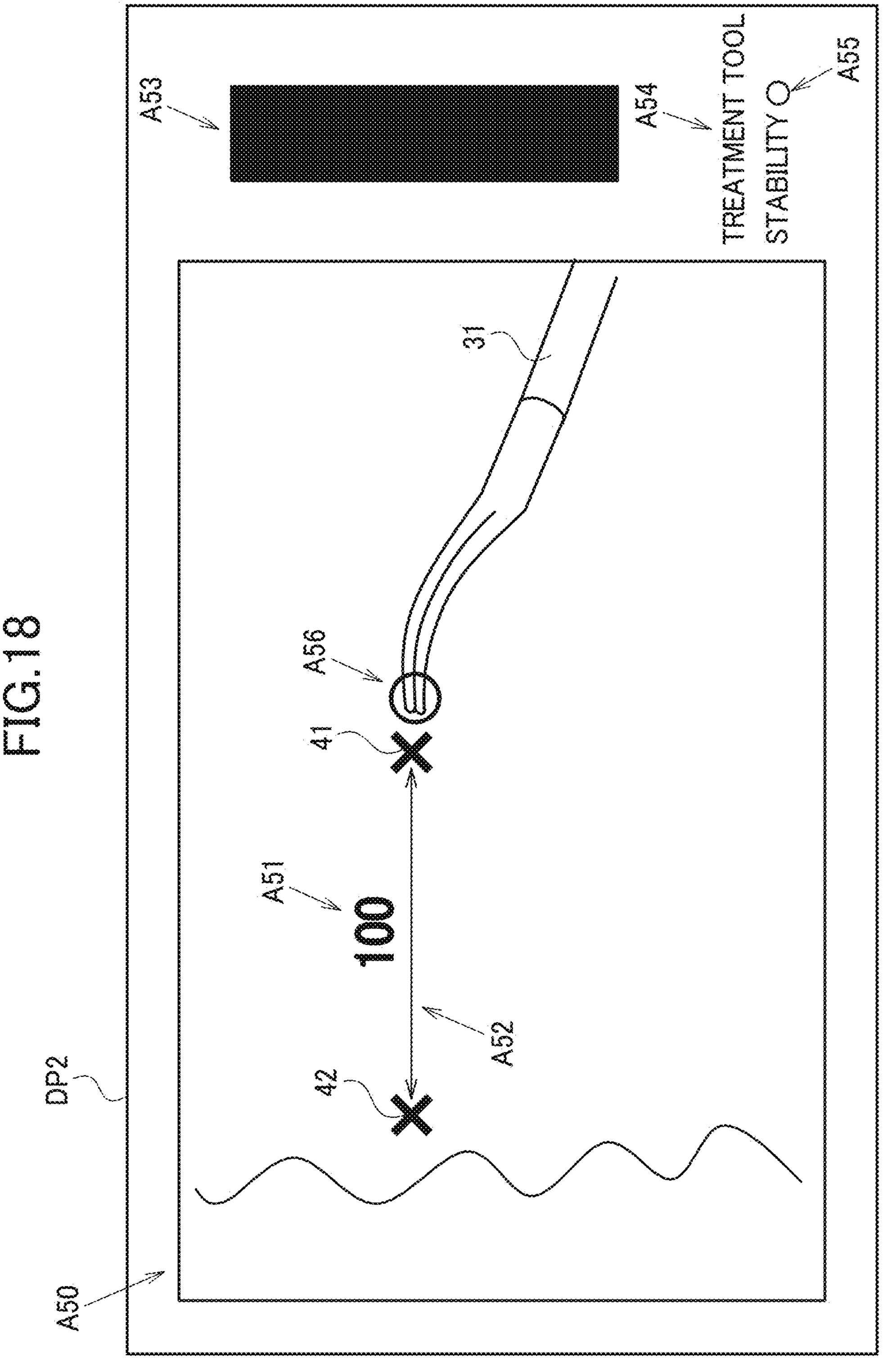
FIG. 18 is another view for describing a screen example including an image indicating a range in which the distal end of the first treatment tool is stable.

This allows the user to easily stabilize the distal end of the first treatment tool 31. With this configuration, the screen example illustrated in FIG. 17 becomes a screen example illustrated in FIG. 18. In FIG. 18, a screen indicated by A50, an icon indicated by A53, an icon indicated by A54, and an icon indicated by A55 are displayed on the second display DP2. Additionally, in addition to the first treatment tool 31, an icon indicated by A51, an icon indicated by A52, and an icon indicated by A56 are displayed on the screen indicated by A50. Since the distal end of the first treatment tool 31 is stable, the icons indicated by A51, A52, A53, A54, and A55 in FIG. 18 are displayed in modes similar to those of the icons indicated by A21, A22, A23, A24, and A25 in FIG. 11. Since the distal end of the first treatment tool 31 is stable under such a state, the moving amount of positional coordinates of the distal end of the first treatment tool 31 is small in each of the previous imaging frames. Hence, a size of the icon indicated by A56 in FIG. 18 is displayed to be smaller than the icon indicated by A46 in FIG. 17.

Figure 19:
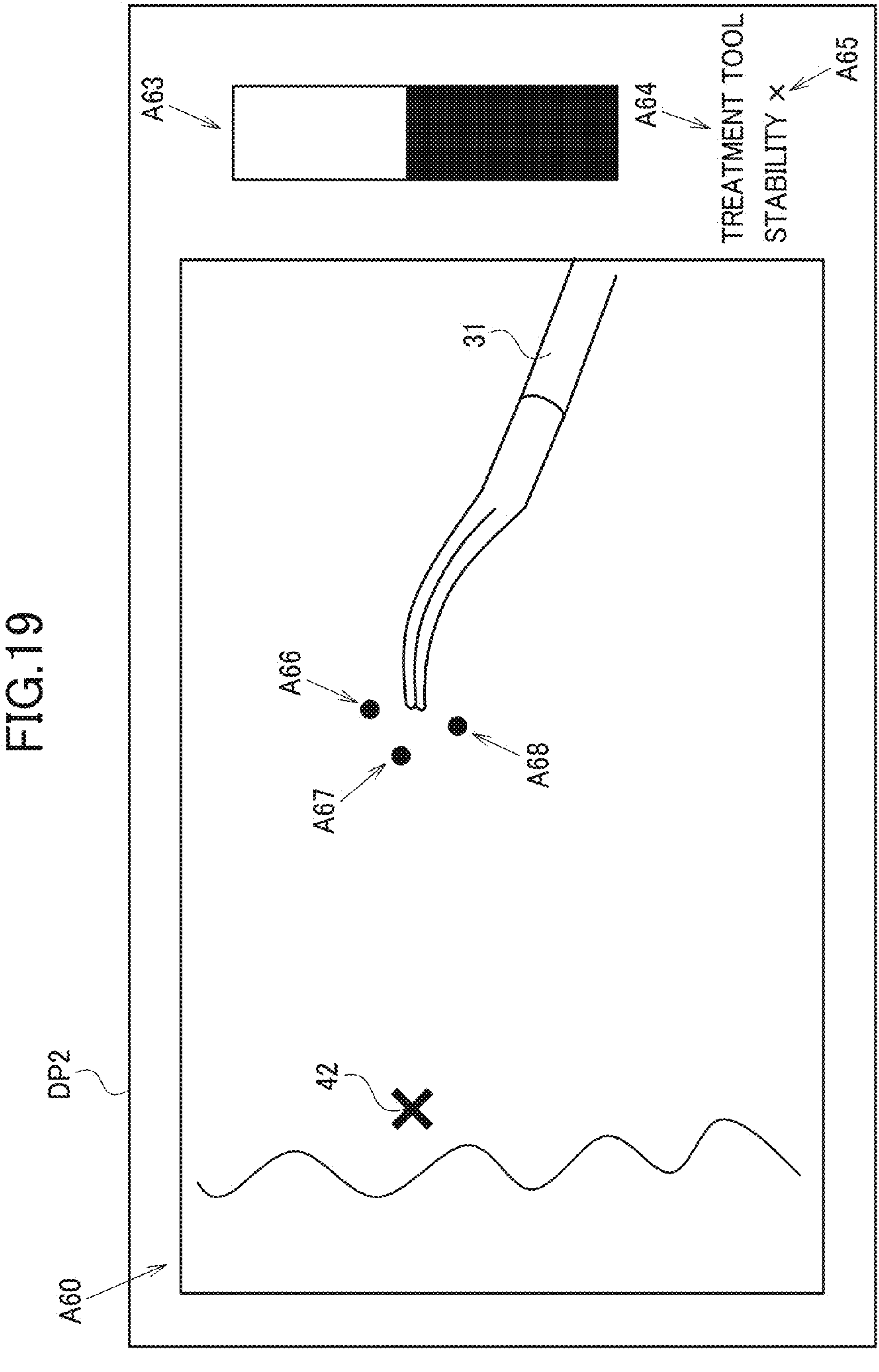
FIG. 19 is a view for describing a screen example including distal end position information regarding the first treatment tool in a previous frame.

Additionally, in a case where the stability of the treatment tool is insufficient, the processor 100 may perform processing of displaying a screen example illustrated in FIG. 19 on the second display DP2. In FIG. 19, a screen indicated by A60, an icon indicated by A63, an icon indicated by A64, and an icon indicated by A65 are displayed on the second display DP2. Additionally, in addition to the first treatment tool 31, an icon indicated by A66, an icon indicated by A67, and an icon indicated by A68 are displayed on the screen indicated by A60.

For example, although the illustration in a flowchart or the like is omitted, in step S290, the processor 100 performs processing of generating display data associated with a predetermined dotted icon based on position information regarding the distal end of the first treatment tool 31 and included in frame data with which the determination is made as YES in step S254 among the previous frame data stored in the memory, which is not illustrated. In step S300, the processor 100 then performs display processing so as to superimpose the icons indicated by A66, A67, and A68 on the image indicated by A60 based on the display data generated in step S290.

Additionally, although illustration is omitted, in a case where the stability of the treatment tool is insufficient, the icons indicated by A66, A67, and A68 in FIG. 19 may be displayed together with the icon indicated by A46 in FIG. 17.

Note that, in the screen examples in FIGS. 17, 18, and 19, the second measurement point 42 is a point selected by the user with the touch panel in step S122 in FIG. 7, but the method illustrated in FIGS. 17 and 18 may also be applied to a case where the distal end of the second treatment tool 32 serves as the second measurement point 42. For example, in a case where neither the distal end of the first treatment tool 31 nor the distal end of the second treatment tool 32 is stable, the icon indicated by A46 in FIG. 17 or the icons indicated by A66, A67, and A68 in FIG. 19 may be displayed at the distal end of each of the first treatment tool 31 and the second treatment tool 32.

In this manner, in the image processing device 10 in accordance with the present embodiment, the processor 100 displays at least the image information for making the moving amount of the first measurement point 41 within the first predetermined range on the display DP (second display DP2). This allows the image processing device 10 to give assistance for stabilizing the distance measurement to the user.

Figure 20:
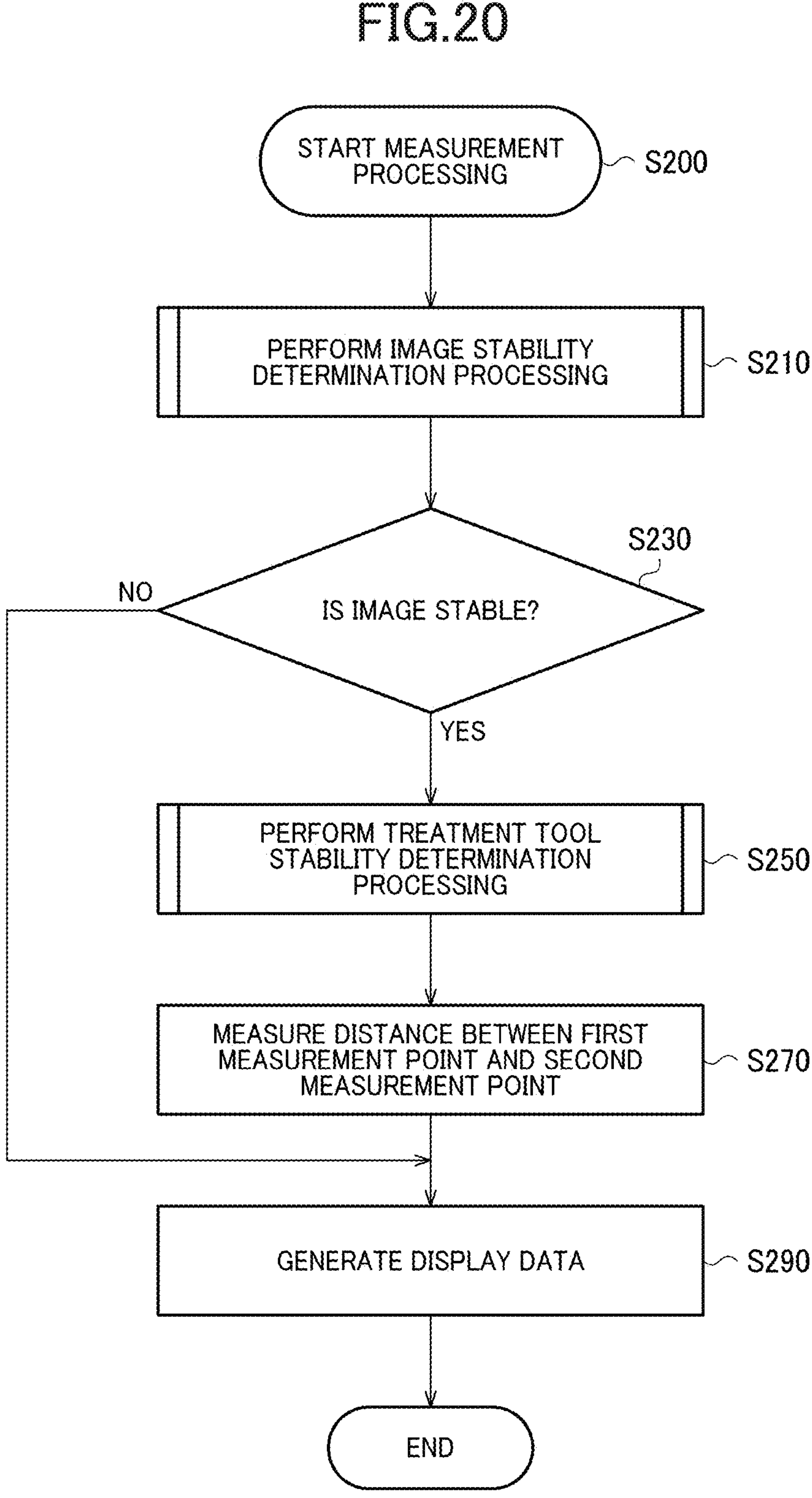
FIG. 20 is a flowchart describing another processing example of measurement processing.

Additionally, for example, the measurement processing (step S200) may be a processing example described in a flowchart in FIG. 20. FIG. 20 is different from FIG. 8 in that image stability determination processing (step S210) and step S230 are added. Note that a description about processing that is similar to the processing that has been already described is omitted below as appropriate.

In FIG. 20, the processor 100 performs the image stability determination processing (step S210), and thereafter performs processing of determining whether or not the image is stable (step S230). Although details of the image stability determination processing (step S210) and step S230 will be described later, the processor 100 determines whether or not an imaging state of the imager of the endoscope 20 is stable. In a case of determining that the image is stable (YES in step S230), the processor 100 performs the treatment tool stability determination processing (step S250) and performs steps S270 and S290 similarly to FIG. 8, and the flow ends.

In contrast, in a case of determining that the image is not stable (NO in step S230), the processor 100 performs step S290, and the flow ends. That is, in FIG. 20, in a case where the image is not stable, the processor 100 determines the stability of the first treatment tool 31 or the like, and updates the endoscope image associated with the frame without performing measurement of the distance between the first measurement point 41 and the second measurement point 42.

Note that a processing example of the measurement processing (step S200) including the image stability determination processing (step S210) is not limited to that illustrated in FIG. 20, and can be modified in various manners. For example, even in a case where the determination is made as NO in step S230, the processor 100 may determine the stability of the first treatment tool 31 or the like, and perform measurement of the distance between the first measurement point 41 and the second measurement point 42. In this case, although illustration in the flowchart is omitted, step S230 is only required to be omitted in FIG. 20. Alternatively, although illustration in the flowchart is omitted, the processor 100 may perform the image stability determination processing (step S210) and the treatment tool stability determination processing (step S250) in parallel in the measurement processing (step S200), and thereafter perform step S230. In this case, in a case of determining YES in step S230, the processor 100 is only required to perform the processing in step S270. In a case of determining NO in step S230, the processor 100 is only required to perform processing in step S290.

A more detailed processing example of the image stability determination processing (step S210) is now described with reference to a flowchart in FIG. 21. The processor 100 performs processing of determining whether or not the endoscope image includes a feature that is inappropriate for measurement (step S212). The feature of the endoscope image that is inappropriate for the measurement is a phenomenon regarding inappropriateness for the stereo matching. Examples of the phenomenon include the image being out-of-focus, the brightness of the whole image being insufficient, and contrast of the whole image being insufficient.

In a case of determining that the endoscope image does not include the feature that is inappropriate for the measurement (NO in step S212), the processor 100 adds 1 to a second count value (step S214). For example, in a case of determining YES in step S214 again in a frame of captured images, the processor 100 further adds 1 to the second count value. That is, in a case where the endoscope image is stable, the second count value cumulatively increases by addition as the number of frames of captured images increases. That is, the second count value has a technical meaning as an index of a period of time in which the state that is appropriate for the measurement continues. Note that a second predetermined value may be set as an upper limit of the second count value. With this setting, in a case where the second count value is more than or equal to the second predetermined value, the user can determine that a state appropriate for the measurement of the distance between the first measurement point 41 and the second measurement point 42 continues for a sufficient amount of time.

In contrast, in a case of determining that the endoscope image includes a feature that is inappropriate for the measurement (YES in step S212), the processor 100 sets the second count value at 0 (step S216). For example, when the second count value continues to increase by addition as a result of determination as NO in step S212, assume a case where determination as YES is made in step S212 for certain reasons. The certain reasons include a change of how an endoscope image is seen due to an external factor such as mist and significant image blurring due to hand movement in the operation of the user who holds the endoscope 20. In a case where such a certain reason occurs, it is thought to be appropriate to set the second count value at 0 so as to allow for the restart of the determination about the stability of the image from the beginning.

Figure 21:
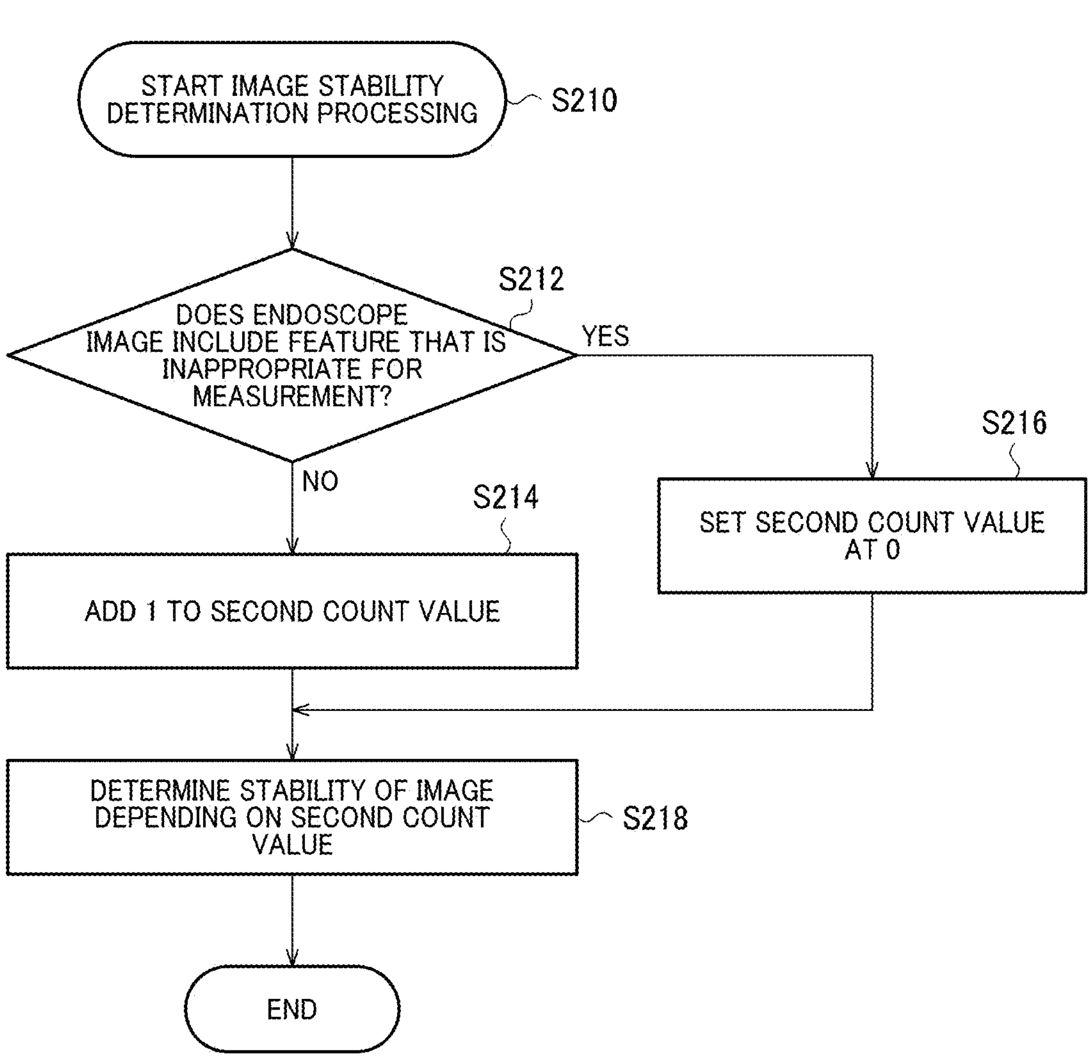
FIG. 21 is a flowchart describing a processing example of image stability determination processing.

Note that contents of step S216 are not limited to those illustrated in FIG. 21, and can be determined as appropriate by the user. For example, processing in step S216 may be processing of subtracting a predetermined number from the second count value. Alternatively, the processor 100 may perform processing of performing neither addition nor subtraction on the second count value, that is, in a case where the determination of NO is made in step S212, perform processing to proceed to step S218 without performing step S214.

The processor 100 then performs step S214 or step S216, and thereafter determines the stability of the image depending on the second count value (step S218). Step S218 is processing similar to the above-mentioned step S259. For example, the processor 100 calculates a ratio of the accumulated second count value to the second predetermined value and obtains a degree of stability of the endoscope image. In subsequent step S290, the processor 100 generates display data corresponding to the result of determination in step S218. In subsequent step S300, the processor 100 displays an image corresponding to the display data generated in step S290 on the second display DP2.

Figure 22:
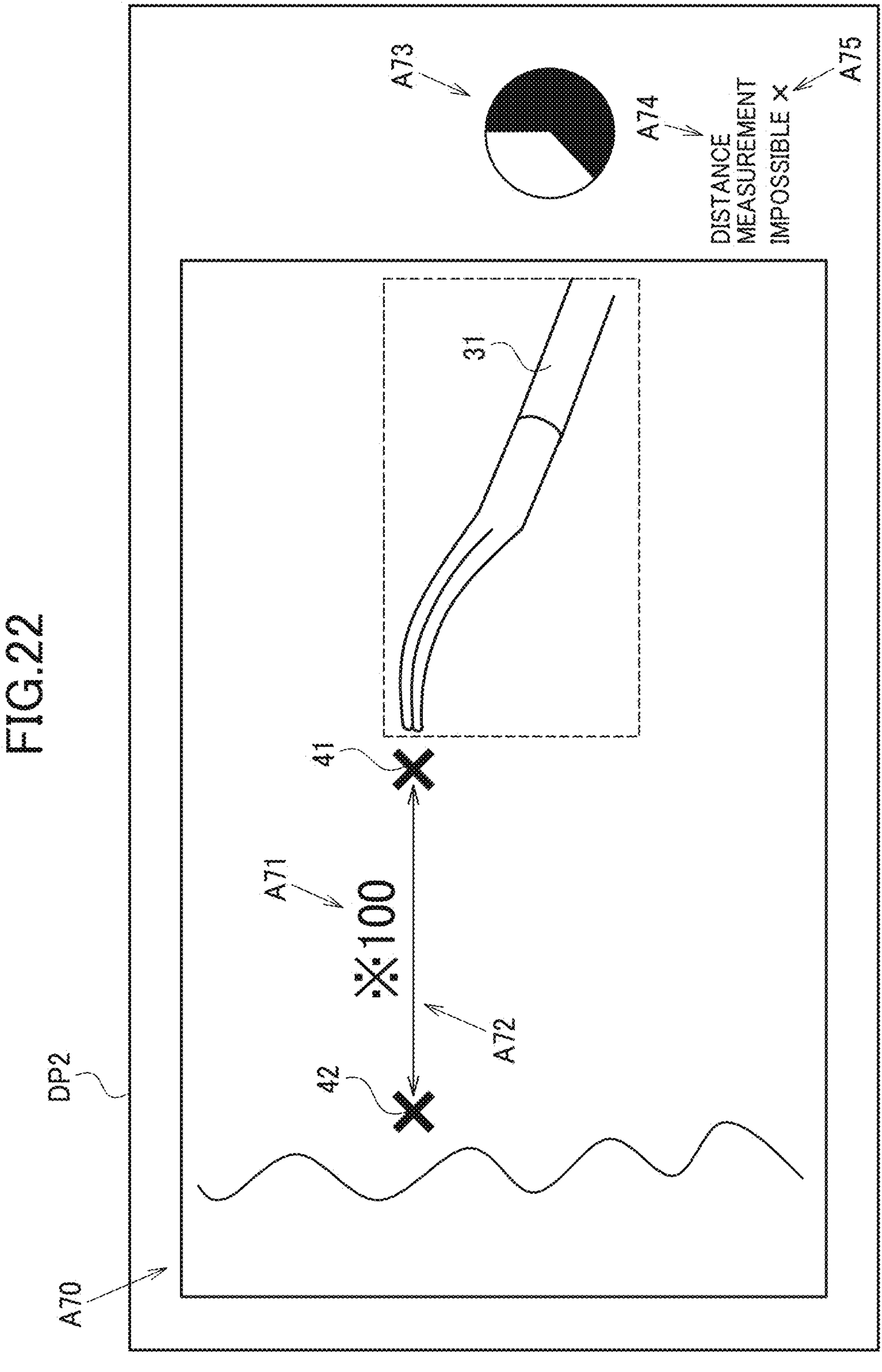
FIG. 22 is a view for describing a screen example including display indicating stability of an image.

FIG. 22 illustrates a screen example in a case where processing in FIGS. 20 and 21 is applied. In FIG. 22, a screen indicated by A70, an icon indicated by A73, an icon indicated by A74, and an icon indicated by A75 are displayed on the second display DP2. The icon indicated by A73, which a circle graph-type icon, represents a ratio of a period of time in which the endoscope image is determined as stable to a period of time in which it is desirable that the endoscope image be stable. In other words, the ratio between the second count value accumulated in step S214 and the second predetermined value is displayed with the graph icon. The icon indicated by A74 includes the character icon regarding the stability of the endoscope image. The icon indicated by A75 is a symbol icon representing a degree of stability of the endoscope image in a simple manner. A state illustrated in FIG. 22 is a state where the stability of the screen is insufficient because the second count value subjected to addition in step S214 in FIG. 21 has not reached a value that satisfies a predetermined ratio with respect to the second predetermined value, and is inappropriate for the measurement of the distance between the first measurement point 41 and the second measurement point 42. The circle graph-type icon indicated by A73 visually represents the ratio of the second count value to the second predetermined value, and the second count value not having reached a value that satisfies the predetermined ratio with respect to the second predetermined value. The icons indicated by A74 and A75 represent the endoscope image being not stable in a simple manner.

Note that a screen example in FIG. 22 is a screen example in which processing that omits step S230 in FIG. 20 is applied. Hence, steps S250 and S270 in FIG. 20 are performed, and a distance information icon indicated by A71 and representing distance information and an arrow icon indicated by A72 are displayed together in FIG. 22. Note that the distance information icon indicated by A71 is similar to the icon indicated by A11 in FIG. 10. Note that the illustration of the icons indicated by A13, A14, and A15 in FIG. 10 is omitted in FIG. 22 for simplification of description, but these icons may be displayed on the second display DP2.

Figure 23:
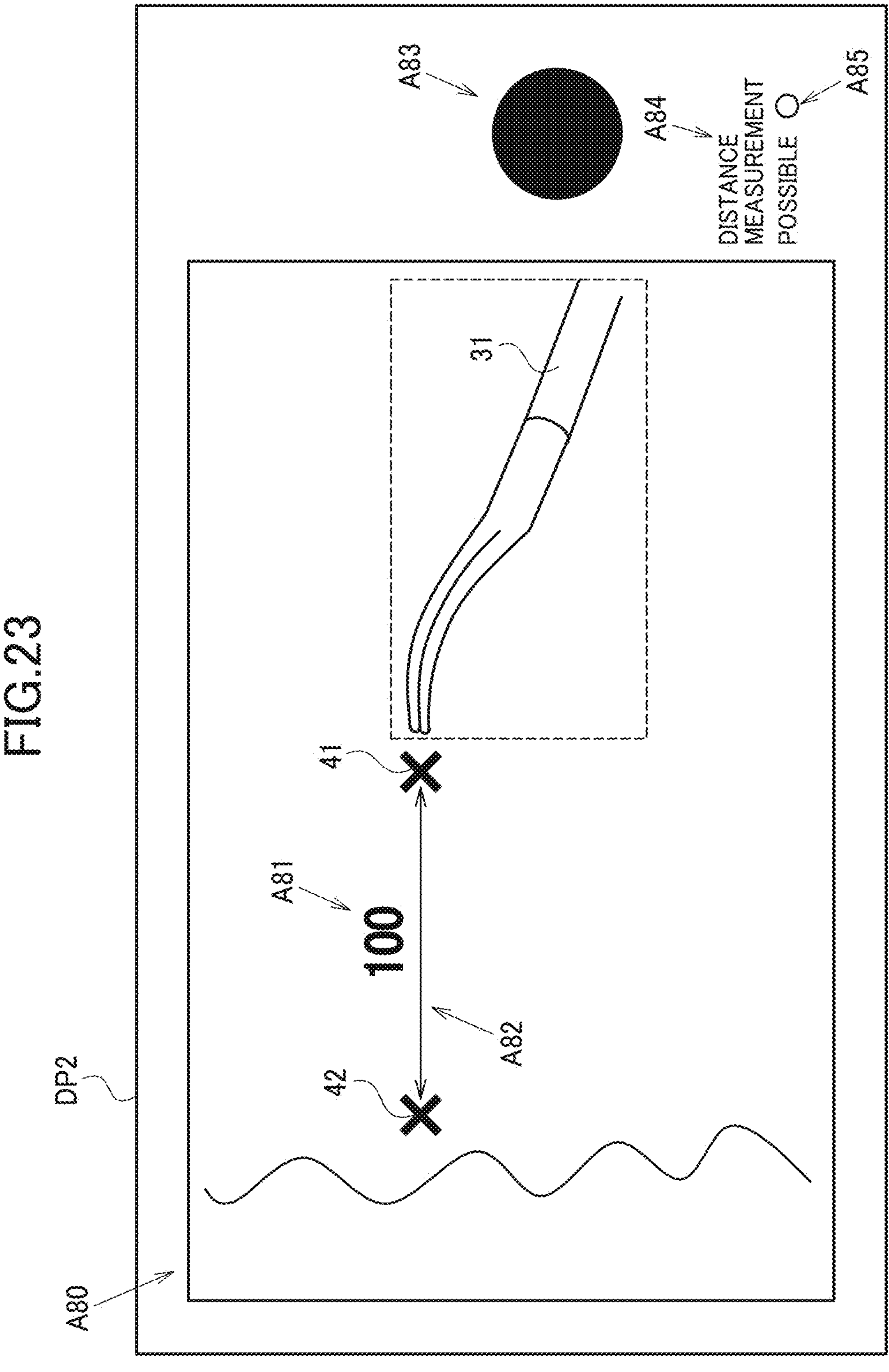
FIG. 23 is another view for describing a screen example including display indicating stability of an image.

FIG. 23 illustrates another screen example in a case where processing in FIGS. 20 and 21 is applied. In FIG. 23, a screen indicated by A80, an icon indicated by A83, an icon indicated by A84, and an icon indicated by A85 are displayed on the second display DP2. A state illustrated in FIG. 23 is a state where the stability of the endoscope image is sufficient because the second count value subjected to addition in step S214 in FIG. 21 has reached the second predetermined value, and it is appropriate for the measurement of the distance between the first measurement point 41 and the second measurement point 42. The circle graph-type icon indicated by A83 represents the second count value having reached the second predetermined value. The icons indicated by A84 and A85 represent the endoscope image being stable in a simple manner.

Note that modes of the icons indicated by A73 and A75 in FIG. 22 are not limited to those illustrated in FIG. 22. Similarly, modes of the icons indicated by A83 and A85 in FIG. 23 are not limited to those illustrated in FIG. 23. For example, a mode of the icon indicated by A73 in FIG. 22 and a mode of the icon indicated by A83 in FIG. 23 may adopt the examples described above with reference to FIG. 15. Similarly, a mode of the icon indicated by A75 in FIG. 22 and a mode of the icon indicated by A85 in FIG. 23 may adopt the patterns described above with reference to FIG. 12.

In this manner, in the image processing device 10 in accordance with the present embodiment, the processor 100 calculates, in a case where the endoscope image is stable for a predetermined period of time, a definite value of the distance. Additionally, the processor 100 performs display indicating that the endoscope image is stable for the predetermined period of time on the display DP (second display DP2). This allows the user to easily grasp that the endoscope image is stable.

Figure 24:
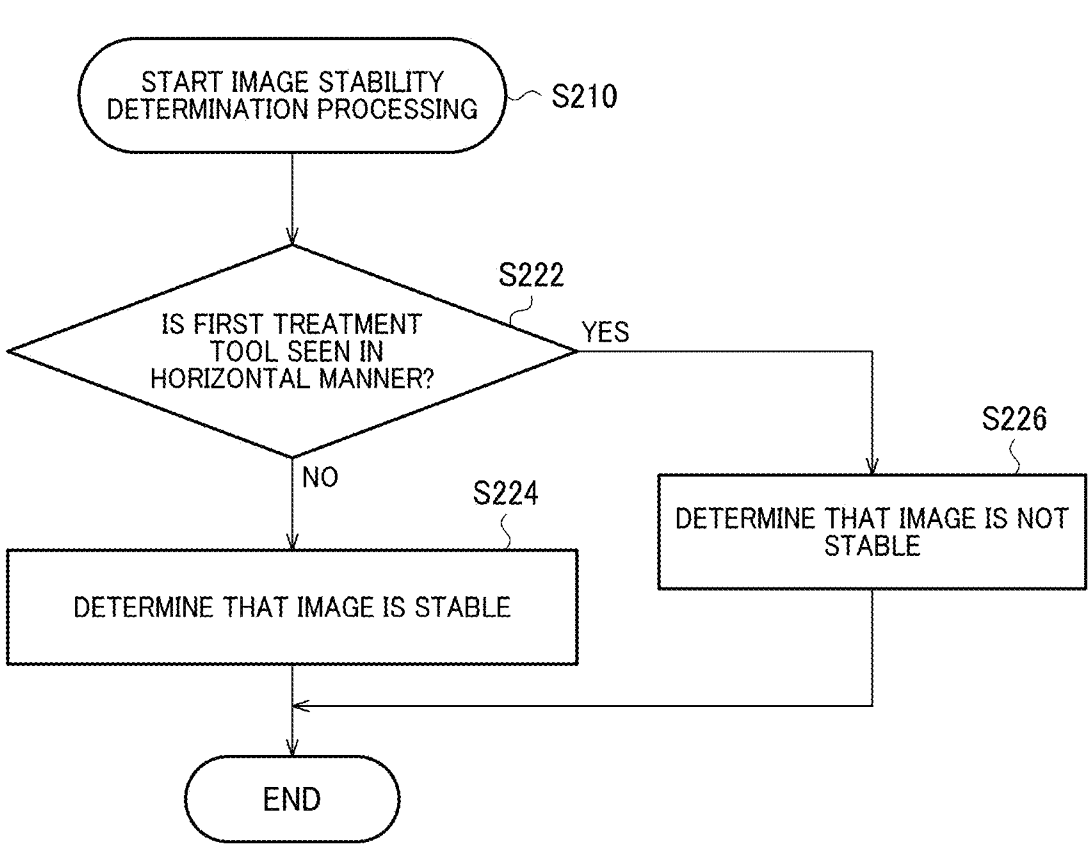
FIG. 24 is a flowchart describing another processing example of image stability determination processing.

Additionally, the image stability determination processing (step S210) may be a processing example described in a flowchart in FIG. 24. In FIG. 24, the processor 100 performs processing of determining whether or not the first treatment tool 31 is seen in a horizontal manner (step S222). For example, the processor 100 performs, based on the treatment tool mask image associated with the first treatment tool 31 designated in step S110, processing of calculating a directional vector in a direction that is parallel with a longitudinal direction of the first treatment tool 31 and processing of calculating an angle formed between the directional vector and the X-axis direction. In a case where the calculated angle is within a predetermined range, the processor 100 then determines that the first treatment tool 31 is seen in the horizontal manner, whereby processing in step S222 can be implemented. Note that the predetermined range may be changed as appropriate depending on a condition of the stereo matching.

In a case of determining that the first treatment tool 31 is not seen in the horizontal manner (NO in step S222), the processor 100 performs processing of determining that the image is stable (step S224), and the flow ends. In contrast, in a case of determining that the first treatment tool 31 is seen in the horizontal manner (YES in step S222), the processor 100 performs processing of determining that the image is not stable (step S226), and the flow ends. In subsequent step S290, the processor 100 performs processing of generating image data corresponding to step S224 or step S226. In subsequent step S300, the processor 100 then performs processing of displaying the image data generated in step S290 on the second display DP2. Note that the image stability determination processing (step S210) may be a combination of the processing in FIG. 21 and the processing in FIG. 24.

Figure 25:
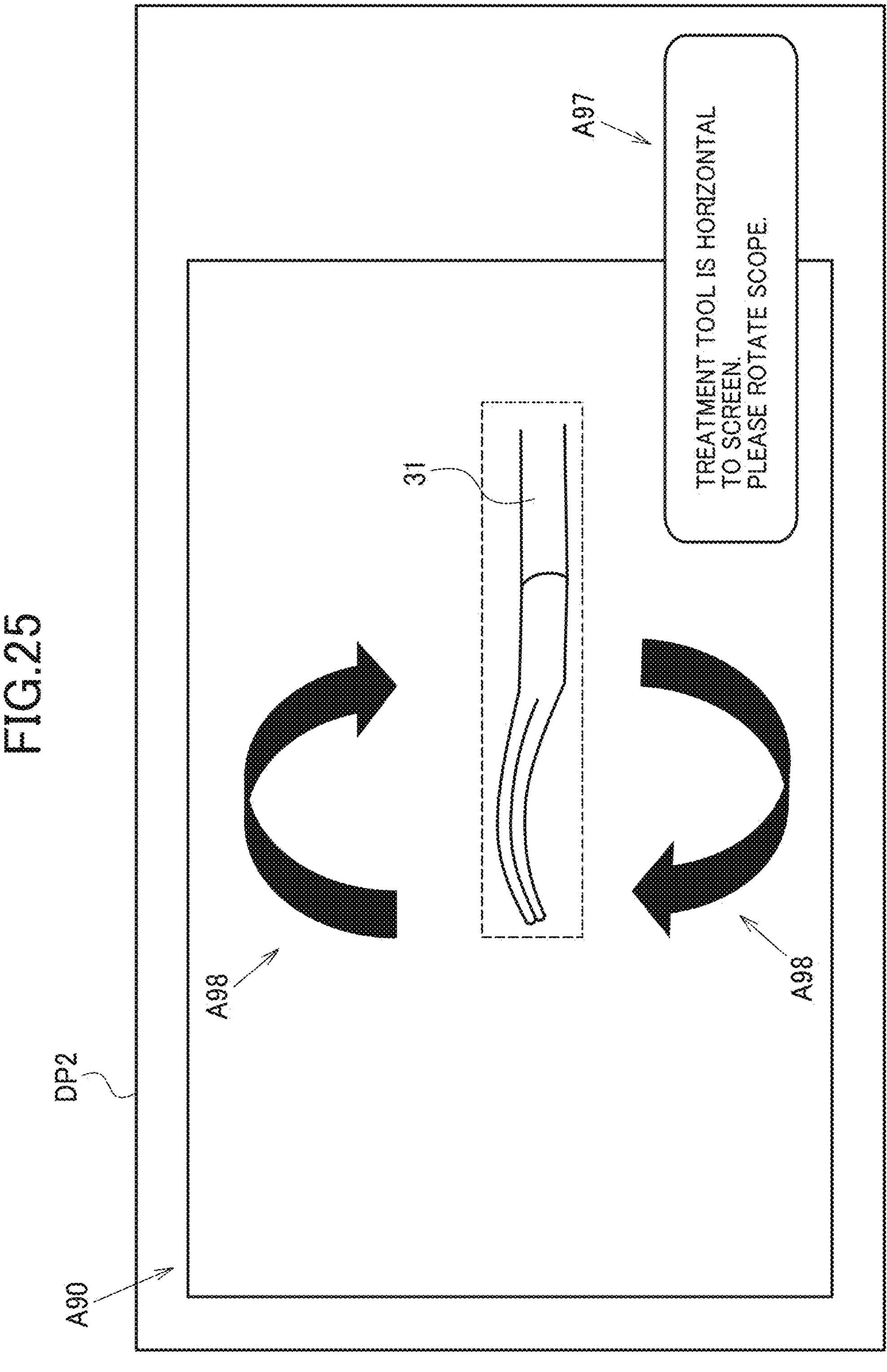
FIG. 25 is a view for describing a screen example including an image prompting the rotation of a scope.

FIG. 25 illustrates a screen example in a case where the processing example in FIG. 24 is applied. Note that in FIG. 25, the display of the icons indicated by A81, A82, A83, A84, and A85, the icon representing the first measurement point 41, and the icon representing the second measurement point 42, which are illustrated in FIG. 23, is omitted, but these icons may be displayed.

In FIG. 25, a screen indicated by A90 is displayed on the second display DP2. On a screen indicated by A90, the first treatment tool 31 is seen in parallel with the horizontal direction. In other words, the first treatment tool 31 is seen in parallel with the parallax direction. Hence, the processor 100 determines YES in step S222 in FIG. 24, and performs step S226. As a result of step S290 and step S300, an image indicated by A97 and the image indicated by A90 are displayed so that the image indicated by A97 is superimposed on the image indicated by A90. The image indicated by A97 includes display of the first treatment tool 31 being seen in the horizontal direction with respect to the screen and display of an instruction for prompting the user to incline the first treatment tool 31 with respect to the horizontal direction. Note that the inclination of the first treatment tool 31 with respect to the horizontal direction is, for example, displacement of the first treatment tool 31 by the user who operates the first treatment tool 31, but is not limited thereto, and may be, for example, rotation or the like of a scope of the endoscope 20 by the user who operates the endoscope 20. For example, in a case where the distal end of the first treatment tool 31 has already been positioned with respect to a desired position, the rotation of the scope of the endoscope 20 is more appropriate than the displacement of the first treatment tool 31. In this manner, in the image processing device 10 in accordance with the present embodiment, the processor 100 displays, in a case where the first treatment tool 31 is in parallel with the parallax direction in a stereo view of the endoscope image, the instruction for inclining the first treatment tool 31 with respect to the parallax direction on the display DP (second display DP2). This can further increase the accuracy of the stereo matching. Since the treatment tool has a scarce texture, there is a possibility that the whole of the treatment tool is seen in the horizontal direction and thereby the accuracy of the stereo matching decreases. Note that the texture mentioned herein is a pattern, a design, or the like that appears by light and dark of each pixel in the image. In this regard, the application of the method in accordance with the present embodiment can prevent the decrease of the accuracy of the stereo matching.

Alternatively, for example, instead of the image indicated by A97 in FIG. 25, an image indicated by A98 may be displayed. Alternatively, the image indicated by A97 and the image indicated by A98 may be displayed together. The image indicated by A98 is an object image indicating a rotation direction of the scope so as to prompt the user to rotate the scope of the endoscope 20. That is, in the image processing device 10 in accordance with the present embodiment, the processor 100 displays, in a case where the first treatment tool 31 is in parallel with the parallax direction in the stereo view of the endoscope image, the object indicating the inclination direction of the first treatment tool 31 on the display DP (second display DP2). This allows the user to easily determine an operation necessary for further increasing construction accuracy of the stereo image.

Note that FIGS. 24 and 25 each illustrate an example of a case where the distance is measured using the first treatment tool 31, but in a case where the distance is measured using the first treatment tool 31 and the second treatment tool 32 as described above with reference to FIG. 14, the images indicated by A97 and A98 in FIG. 25 may be displayed by application of the processing in FIG. 24 also to the second treatment tool 32, and various modifications can be made.

Figure 26:
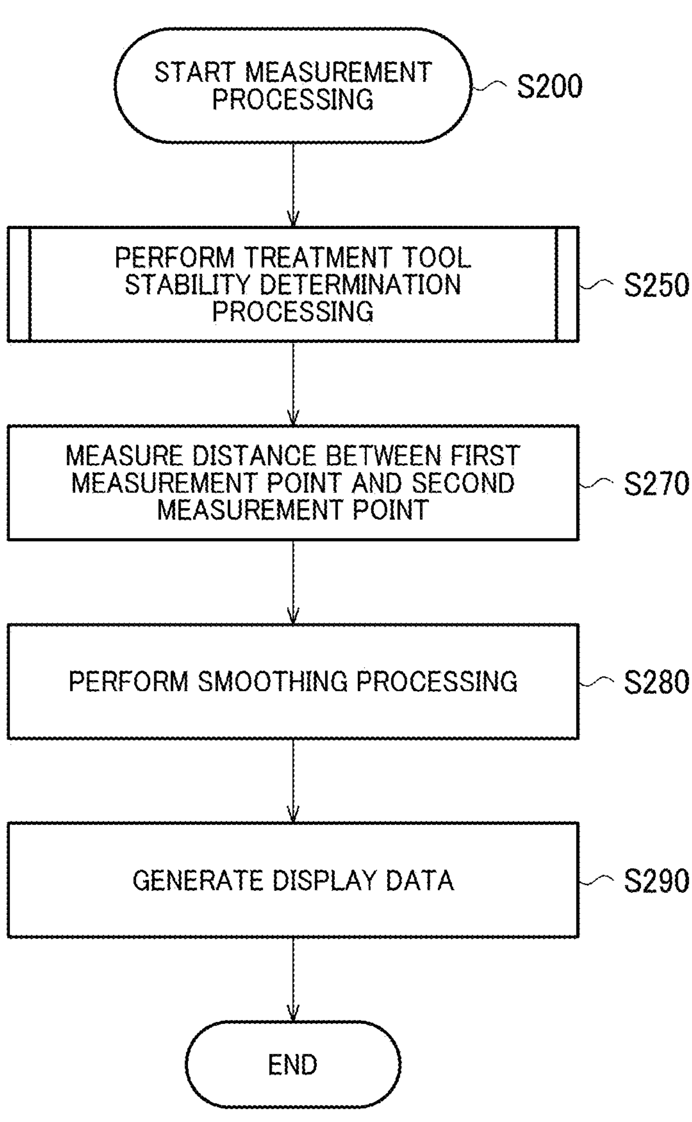
FIG. 26 is a flowchart describing another processing example of measurement processing.

Additionally, for example, the measurement processing (step S200) in the present embodiment may be a processing example described in a flowchart in FIG. 26. The processing example in FIG. 26 is different from the processing example in FIG. 8 in that smoothing processing (step S280) is further performed after the processing in step S270.

Examples of the smoothing processing (step S280) include processing of smoothing a measured distance in a time direction. More specifically, for example, the processor 100 performs processing of calculating an average value of the distance information measured in step S270 and distance information in previous frames stored in the memory, which is not illustrated. The average value mentioned herein is an arithmetic mean value, and is, for example, a value obtained by division of a sum of the distance information stored in the memory, which is not illustrated, by the number of frames. The processor 100 then generates display data of the distance information based on the average value calculated in step S290. With this processing, although illustration is omitted, an icon representing smoothed distance information is displayed on the second display DP2.

In calculation of the average value in step S280 in FIG. 26, the required number of previous frames of captured images is preferably identical to the first predetermined value. This enables display of more accurate distance information on the second display DP2. Note that the three-dimensional position information regarding the first measurement point 41 and the second measurement point 42 and calculated in step S130 may be similarly smoothed in the time direction.

In other words, to smooth the measured distance, the distance measurement needs to be stable for a predetermined period of time. The predetermined period of time may be, for example, the first predetermined period of time described above with reference to FIG. 9, and may be the second predetermined period of time described above with reference to FIG. 13.

Alternatively, processing of smoothing the three-dimensional position information regarding the first measurement point 41 over time may be performed instead of step S280. In this case, processing of smoothing the three-dimensional position information regarding the first measurement point 41 over time is performed before step S270 is performed. The same applies to the second measurement point 42.

Figure 27:
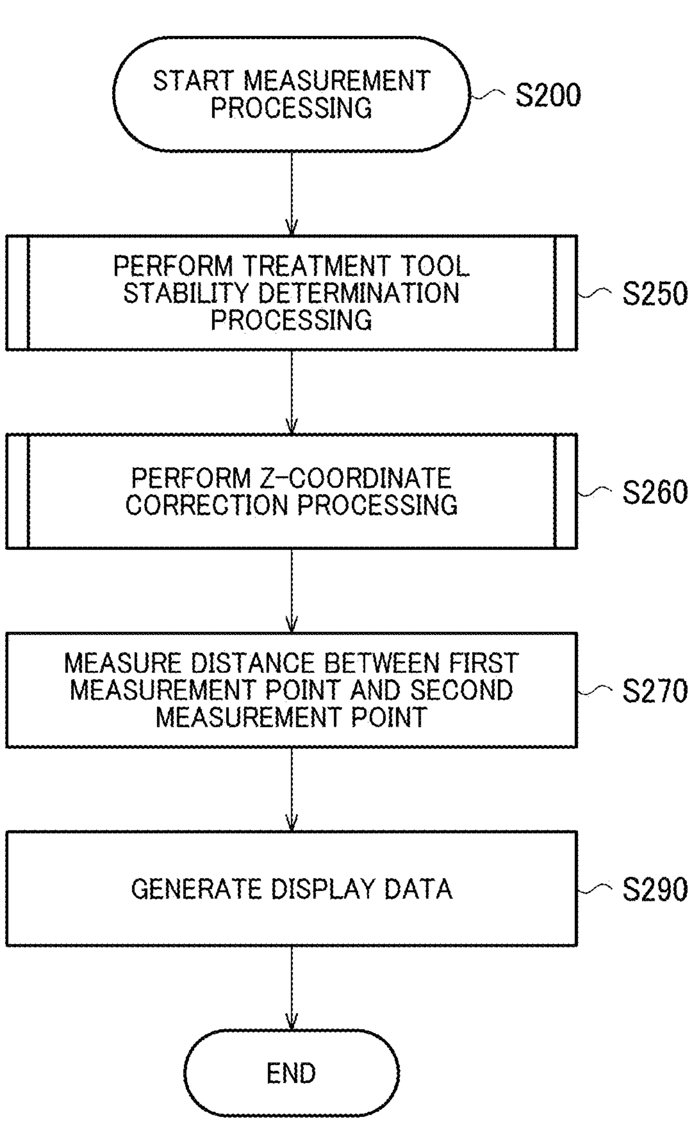
FIG. 27 is a flowchart describing another processing example of measurement processing.

Alternatively, for example, a method of smoothing the three-dimensional position information in a spatial direction may be applied. More specifically, for example, by making the measurement processing (step S200) like the processing example in FIG. 27, Z-coordinates, among the three-dimensional position information regarding the first measurement point 41, may be smoothed in the spatial direction. The processing in FIG. 27 is different from FIG. 8 in inclusion of Z-coordinate correction processing (step S260).

Figure 28:
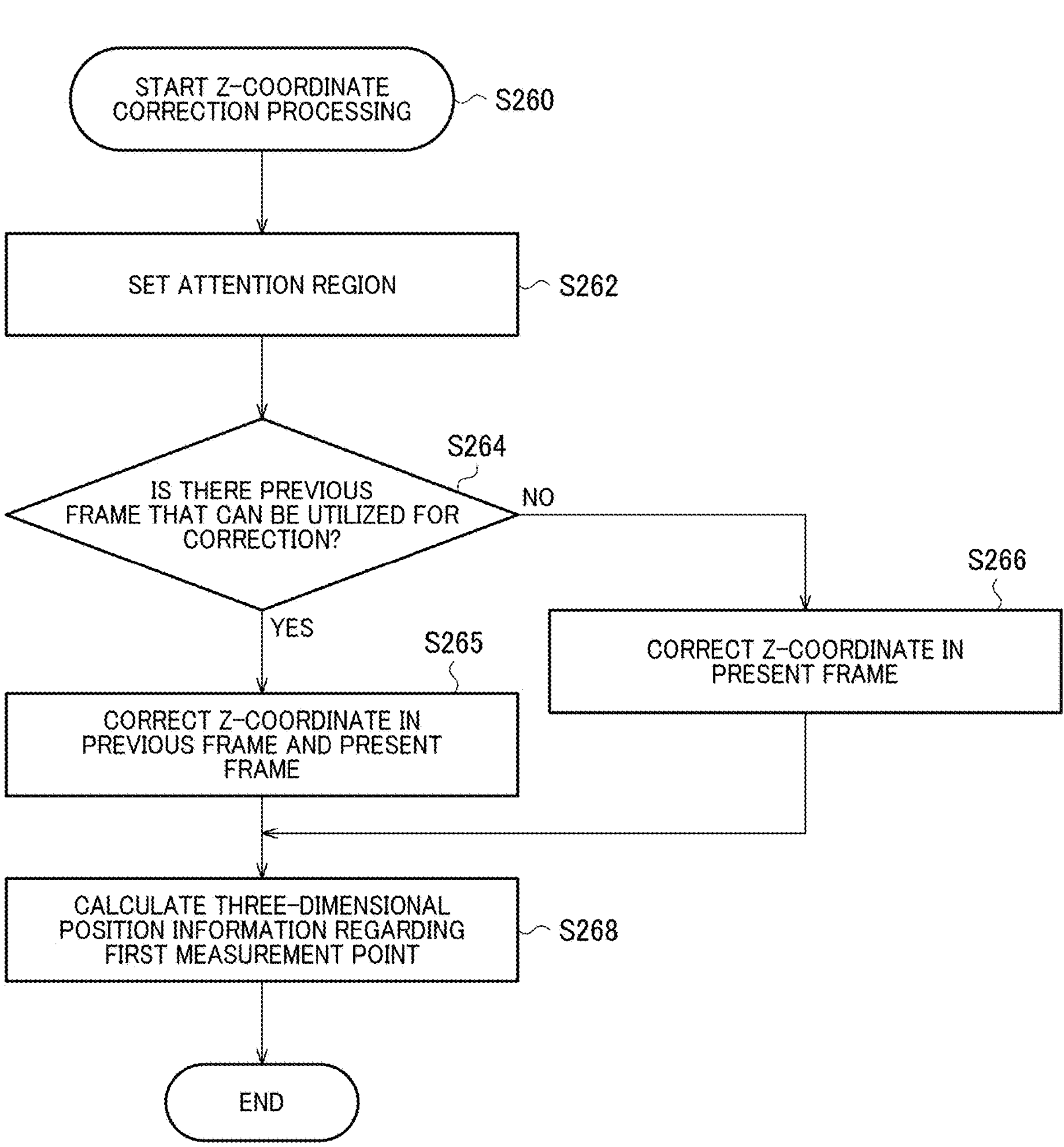
FIG. 28 is a flowchart describing a processing example of Z-coordinate correction processing.

FIG. 28 is a more detailed flowchart of the Z-coordinate correction processing (step S260). The processor 100 performs processing of setting an attention region (step S262). Specifically, as indicated by B30 in FIG. 29A, the attention region is set in the perimeter of the first measurement point 41. The processor 100 then performs processing of determining whether or not there is a previous frame that can be utilized for correction (step S264). More specifically, the processor 100 determines whether or not data in the frame that is determined as YES in step S254 in FIG. 9 is stored in the memory, which is not illustrated.

In a case of determining that there is the previous frame that can be utilized for correction (YES in step S264), the processor 100 performs processing of correcting a Z-coordinate with respect to the previous frame and the present frame (step S265). In contrast, in a case of determining that there is no previous frame that can be utilized for correction (NO in step S264), the processor 100 performs processing of correcting the Z-coordinate with respect to the present frame (step S266).

The correction of the Z-coordinate in step S266 is, more specifically, calculation of an average value or a median value with respect to Z-coordinates of pixels associated with an edge at the distal end of the first treatment tool 31 in the attention region of the stereo image in the present frame. The pixels associated with the edge at the distal end of the first treatment tool 31 in the attention region are, for example, pixels associated with a region indicated by B31 in FIG. 29A. Note that whether the average value is adopted or the median value is adopted may be determined as appropriate by the user, but, for example, in a case where distribution of data of the Z-coordinates tends to be different from normal distribution due to occurrence of large noise, the median value is more appropriate than the average value. For example, in a case where a value of the Z-coordinate includes five pieces of data (1, 3, 5, 6, and 20), the average value is 7 and the median value is 5. However, if data of Z=20 is handled as noise, it is thought that the median value is more appropriate than the average value.

Note that, to correct the Z-coordinate in step S265, the processor 100 is only required to perform, for example, calculation similar to that in step S266 on each of the previous frames and use a median value of Z-coordinates calculated in the respective frames.

Figure 29A:
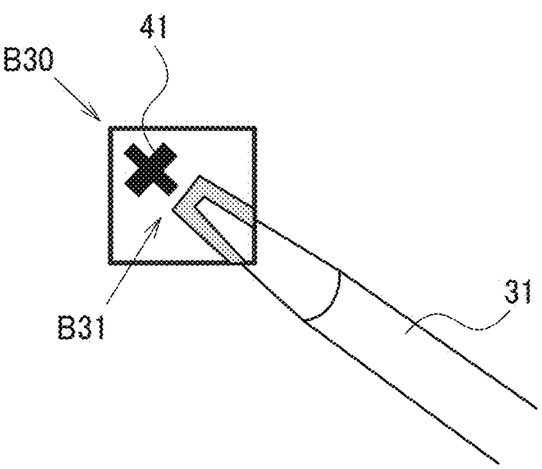
FIG. 29A is a view for describing an attention region.
Figure 29B:
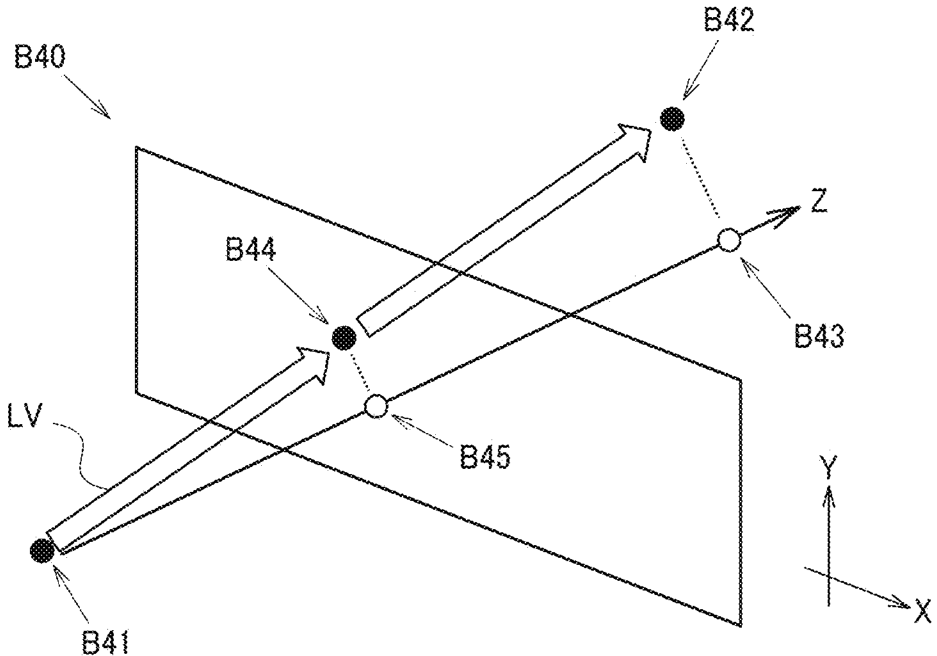
FIG. 29B is a view for describing a method of calculating three-dimensional position information regarding a first measurement point after correction.

Thereafter, the processor 100 performs processing of calculating the three-dimensional position information regarding the first measurement point 41 (step S268). For example, by using a method of perspectively projecting the three-dimensional position information regarding the first measurement point 41 to a plane of the criterion image, it is possible to implement the processing in step S268. For example, a position indicated by B41 in FIG. 29B is a point of origin of the criterion camera, a position indicated by B42 is a three-dimensional position of the first measurement point 41 after the correction, and a position indicated by B43 is a position of the Z-coordinate of the first measurement point 41 after the correction. On the plane of the criterion image indicated by B40, a position indicated by B44 is a position corresponding to the first measurement point 41 in the criterion image, and a point indicated by B45 is an intersection point between the Z-axis of the criterion camera and the plane of the criterion image. A line-of-sight vector LV is a vector that is headed from a position of the point of origin indicated by B41 toward the position indicated by B44, and is headed further toward the three-dimensional position of the first measurement point 41, which is indicated by B42.

In this case, the position information indicated by B44 is known by step S100, and the Z-coordinate of the position indicated by B45 is known because it is the Z-coordinate corrected in step S265 or step S266. Additionally, a triangle formed by the point indicated by B41, the point indicated by B42, and the point indicated by B43 has a similarity relationship with a triangle formed by the point indicated by B41, the point indicated by B44, and the point indicated by B45. Hence, by using a camera parameter such as a focal length, it is possible to change a scale of the line-of-sight vector LV, and obtain the three-dimensional position information regarding the point indicated by B42, that is, the three-dimensional position information regarding the first measurement point 41 after correction.

In this manner, in the image processing device 10 in accordance with the present embodiment, the processor 100 uses the line-of-sight vector LV based on a median value or an average value of depth coordinates in a peripheral region in measurement position coordinates of the first measurement point 41 in the endoscope image and the measurement position coordinates to obtain the three-dimensional position information regarding the first measurement point 41. With this configuration, it is possible to obtain the position information regarding the first measurement point 41 by the stereo matching with higher accuracy. Since reflection or ghost occurs due to the treatment tool containing metal, the treatment tool having a scarce texture, or the like, a variation in Z-coordinates is larger after the stereo matching. In this regard, by the application of the method in accordance with the present embodiment, it is possible to smooth the Z-coordinates over a space without smoothing X-coordinates and Y-coordinates of the first measurement point 41. As a result, it is possible to further increase the accuracy of calculation of the first measurement point 41. With this configuration, it is possible to obtain the measured distance with higher accuracy.

Note that the above-mentioned smoothing processing in the time direction or the above-mentioned smoothing processing in the spatial direction can be applied also to the case where the distal end of the second treatment tool 32 serves as the second measurement point 42.

As described above, in the image processing device 10 in accordance with the present embodiment, the processor 100 performs smoothing processing in the time direction or the smoothing processing in the spatial direction on at least the first measurement point 41 to measure the distance. This can further increase the accuracy of the distance measurement.

Additionally, for example, as illustrated in a screen example indicated by A100 in FIG. 30, a position away from the distal end position of the first treatment tool 31 may be able to be designated as the first measurement point 41. Note that, in the screen example indicated by A100, the second measurement point 42 is illustrated as the point designated by step S120 in FIG. 7.

Figure 31:
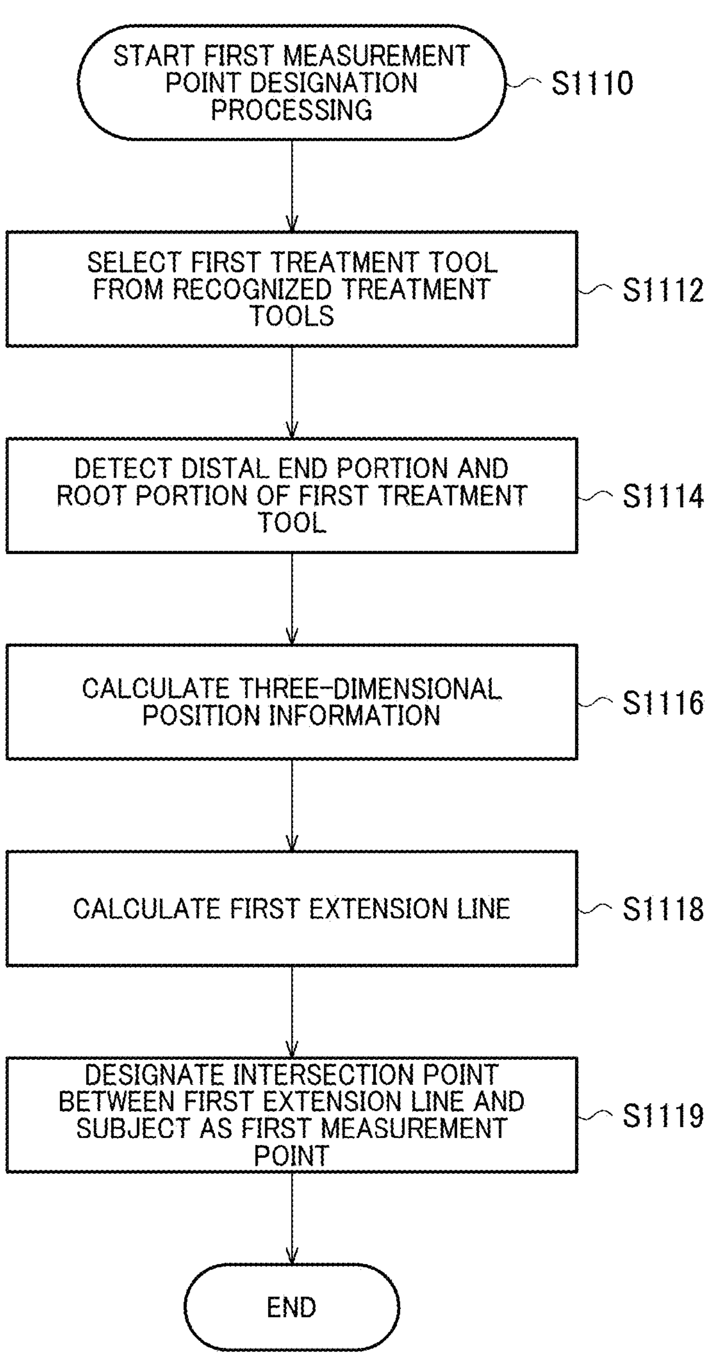
FIG. 31 is a flowchart describing another processing example of the first measurement point designation processing.

For example, the processor 100 performs processing that is modified to the first measurement point designation processing (step S1110) described in FIG. 31, whereby the screen example indicated by A100 in FIG. 30 can be implemented. In FIG. 31, the processor 100 functions as the measurement point selection section 114, and performs processing of selecting the first treatment tool 31 among the recognized treatment tools (step S1112). Step S1112 in FIG. 31 is processing corresponding to steps S112 and S114 in FIG. 6. The processor 100 then performs processing of detecting the distal end portion and root portion of the selected first treatment tool 31 (step S1114). The root portion of the first treatment tool 31 is, among a portion of the first treatment tool 31 that can be displayed on the second display DP2, a portion on the most root side.

Thereafter, the processor 100 performs processing of calculating the three-dimensional position information (step S1116). Step S1116 is similar to the three-dimensional position information calculation processing (steps S130) in FIG. 5 and the like. More specifically, for example, the processor 100 performs step S1112 to generate the treatment tool mask image associated with the first treatment tool 31, and performs step S1116 to perform stereo matching based on the treatment tool mask image and stereo matching based on a subject image excluding a portion associated with the first treatment tool 31 from the stereo image.

Figure 32:
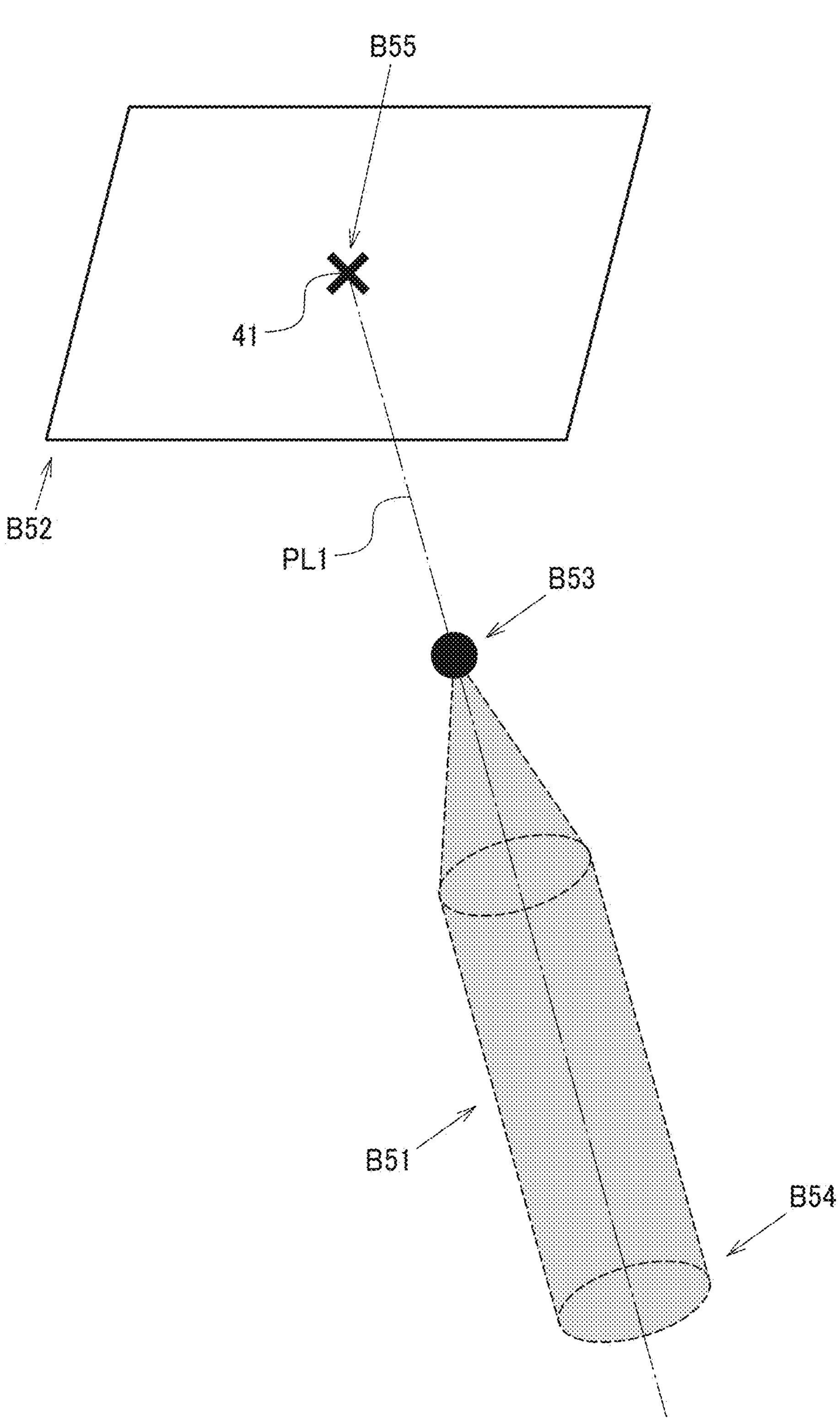
FIG. 32 is a view for describing designation of the first measurement point in detail.

In this manner, the processor 100 performs steps S1112, S1114, and S1116, and thereby constructs a three-dimensional structure of the first treatment tool 31, for example, as indicated by B51 in FIG. 32. Note that a region indicated by B52 conceptually represents a part of the three-dimensional structure of the subject excluding the portion associated with the first treatment tool 31. Note that FIG. 32 does not specifically identify the structure of the first treatment tool 31 and the like.

Back to the flowchart in FIG. 31, the description continues. Thereafter, the processor 100 performs processing of calculating a first extension line PL1 (step S1118). Specifically, for example, the distal end portion of the first treatment tool 31, which is detected by step S1114, is three-dimensionally constructed by step S1116 as indicated by B53. Similarly, the root portion of the first treatment tool 31, which is detected by step S1114, is three-dimensionally constructed by step S1116 as indicated by B54. Subsequently, the first extension line PL1 is calculated by step S1118 based on the constructed distal end portion and the root portion. For example, the processor 100 performs processing of calculating a straight line passing coordinates of the barycentric position of the distal end portion indicated by B53 and coordinates of the barycentric position of the root portion indicated by B54. With this processing, the first extension line PL1 becomes a straight line that is substantially identical to a straight line that passes through the distal end of the first treatment tool 31 and that is parallel with the longitudinal direction of the first treatment tool 31. With this configuration, it is possible to obtain a direction which the distal end of the first treatment tool 31 faces with high accuracy. As a result, it is possible to designate the first measurement point 41 at a desired position with high accuracy.

Thereafter, the processor 100 performs processing of designating an intersection point between the first extension line PL1 and the subject as the first measurement point 41 (step S1119). As a result, as indicated by B55 in FIG. 32, an intersection point between the first extension line PL1 obtained in step S1118, and the subject indicated by B52 is obtained. That is, the point indicated by B55 is designated as the first measurement point 41, whereby the first measurement point designation processing (step S1110) illustrated in FIG. 31 ends.

Note that, although illustration in the flowchart is omitted, for example, executing the processing in step S1116 or subsequent steps between steps S1114 and S1116 in a state where the second measurement point 42 is further designated by processing similar to step S122 in FIG. 7 causes a state similar to the state where the flow of the position designation calculation processing (step S100) ends.

Additionally, although illustration in the flowchart is omitted, in a case where the second measurement point 42 is desired to be further designated at a position away from the distal end of the second treatment tool 32, the processor 100 is only required to select the first treatment tool 31 and the second treatment tool 32 in step S1112, and perform steps S1114, S1116, S1118, and S1119 with respect to the selected first treatment tool 31 and the selected second treatment tool 32.

Additionally, although the first measurement point 41 is designated using the three-dimensional construction processing based on the stereo image in FIGS. 31 and 32, the method in accordance with the present embodiment is not limited thereto, and the first measurement point 41 may be able to be designated on a two-dimensional image. In this case, for example, the processor 100 is only required to perform the first measurement point designation processing (step S2110) described in a flowchart in FIG. 33.

Figure 33:
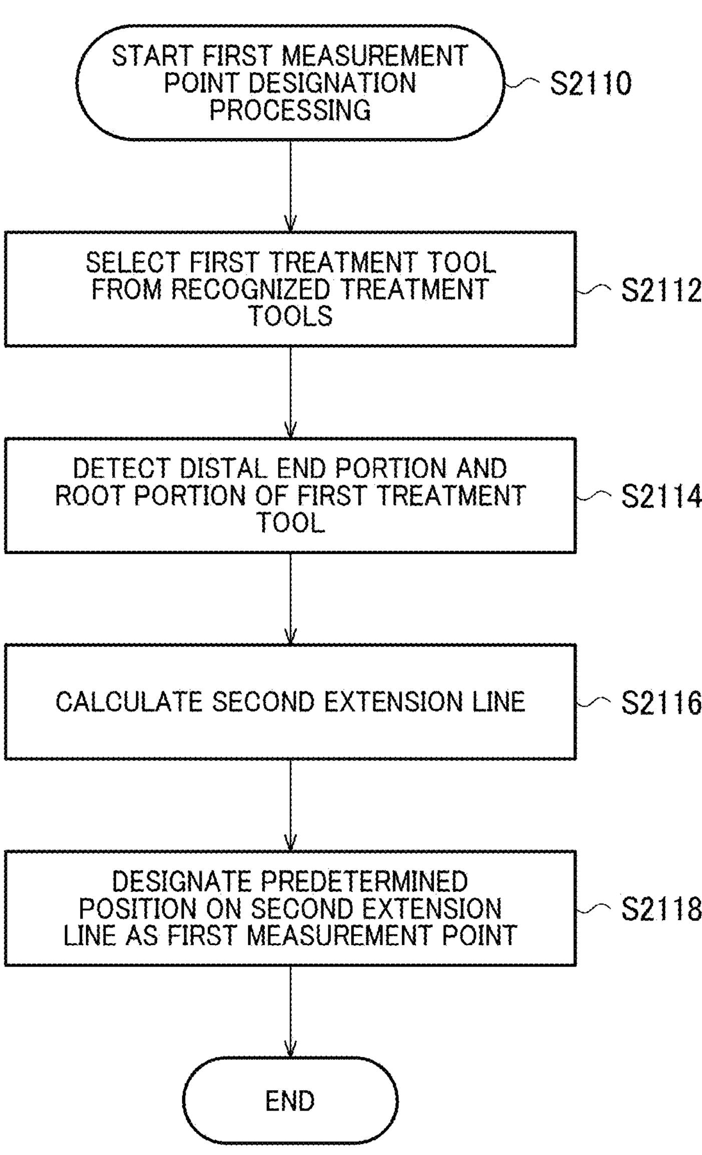
FIG. 33 is a flowchart describing another processing example of the first measurement point designation processing.

In FIG. 33, the processor 100 functions as the measurement point selection section 114, and performs processing of selecting the first treatment tool 31 among the recognized treatment tools (step S2112) similarly to step S1112 in FIG. 31. The processor 100 then performs processing of detecting the distal end portion and root portion of the selected first treatment tool 31 (step S2114) similarly to step S1114 in FIG. 31.

Thereafter, the processor 100 performs processing of calculating a second extension line PL2 (step S2116). Specifically, for example, in a criterion image indicated by B60 in FIG. 34, the processor 100 performs step S2112 to recognize a region indicated by B61 as the first treatment tool 31. The processor 100 then performs step S2114 to detect a distal end portion indicated by B62 and a root portion indicated by B63. The processor 100 then performs step S2116 to calculate the second extension line PL2. For example, the processor 100 performs processing of calculating a straight line passing coordinates of the barycentric position of the distal end portion indicated by B62 and coordinates of the barycentric position of the root portion indicated by B63. With this processing, the second extension line PL2 becomes a straight line that is substantially identical to a straight line that passes through the barycenter of the distal end portion of the first treatment tool 31 recognized in the criterion image and that is parallel with the longitudinal direction of the first treatment tool 31. In this manner, the method of calculating the second extension line PL2 is different from the above-mentioned method of calculating the first extension line PL1 in that the processor 100 does not function as the three-dimensional construction section 112.

Back to the flowchart in FIG. 33, the description continues. Thereafter, the processor 100 performs processing of designating a predetermined position on the second extension line PL2 as the first measurement point 41 (step S2118). Specifically, for example, the processor 100 performs, as indicated by B65 in FIG. 34, processing of setting the first measurement point 41 at a position at which the second extension line PL2 is extended by a length indicated by B64 from the coordinates of the barycenter of the distal end portion indicated by B62.

Figure 34:
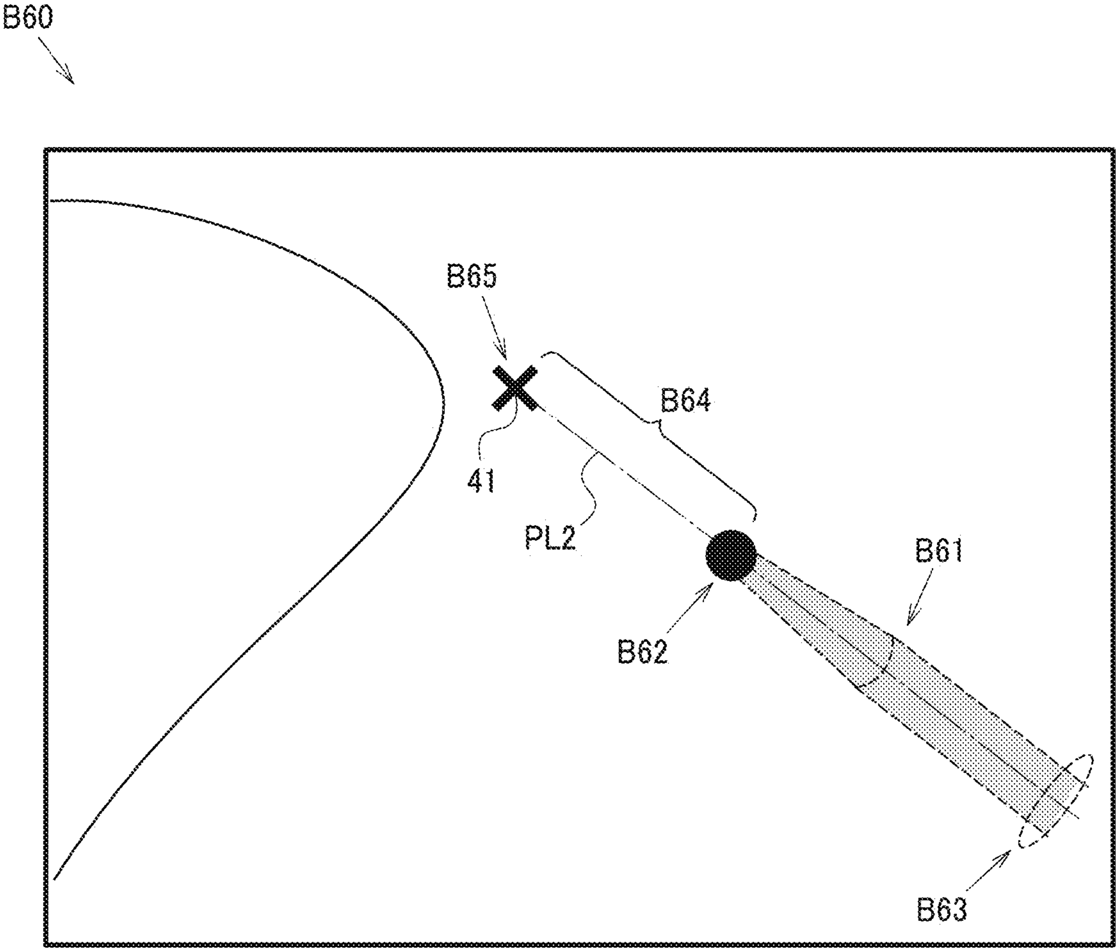
FIG. 34 is another view for describing designation of the first measurement point in detail.

Note that, similarly to the criterion image indicated by B60 in FIG. 34, the processing in FIG. 33 is also performed on the reference image. Thereafter, similarly to FIG. 4, the processor 100 performs the second measurement point designation processing (step S120) and the three-dimensional position information calculation processing (step S130), and thereby ends the position designation calculation processing (step S100). As a result, the stereo matching based on the stereo image is performed, and the three-dimensional position information regarding the first measurement point 41 is obtained.

Note that, in a case where the second measurement point 42 is desired to be further designated at a position away from the distal end of the second treatment tool 32 with use of the method described in FIG. 33, the processor 100 is only required to perform processing of selecting the first treatment tool 31 and the second treatment tool 32 in step S2112, and perform steps S2114, S2116, and S2118 with respect to the selected first treatment tool 31 and the selected second treatment tool 32.

As described above, in the image processing device 10 in accordance with the present embodiment, the processor 100 obtains the three-dimensional position information with the intersection point between the straight line based on the three-dimensional position information regarding at least a portion of an axis portion of the first treatment tool 31 and the three-dimensional position information regarding the distal end of the first treatment tool 31 and the subject serving as the first measurement point 41. This enables designation of the first measurement point 41 at a freely-selected position in a region which the distal end of the first treatment tool 31 does not directly reach. For example, there is a case where a desired position on a surface of a predetermined tissue is desired to be designated as the first measurement point 41 but the distal end portion of the first treatment tool 31 does not reach the desired position due to an insufficient length of the axis portion of the first treatment tool 31. In this regard, by application of the method in accordance with the present embodiment, it is possible to handle a position on the extension line in a direction which the distal end of the first treatment tool 31 faces as the first measurement point 41.

Additionally, the processor 100 may calculate the three-dimensional position information regarding the first measurement point 41 based on a predetermined position on a straight line based on two-dimensional position information regarding at least a portion of the axis portion of the first treatment tool 31 and two-dimensional position information regarding the distal end of the first treatment tool 31. With this configuration, it is possible to obtain an effect that is similar to the above-mentioned effect.

Additionally, for example, in a case of having succeeded in measurement of a desired distance, the processor 100 may be capable of tracking the first measurement point 41 and the second measurement point 42 for predetermined time. For example, the position designation calculation processing (step S100) may be as a processing example described in a flowchart in FIG. 35.

Figure 35:
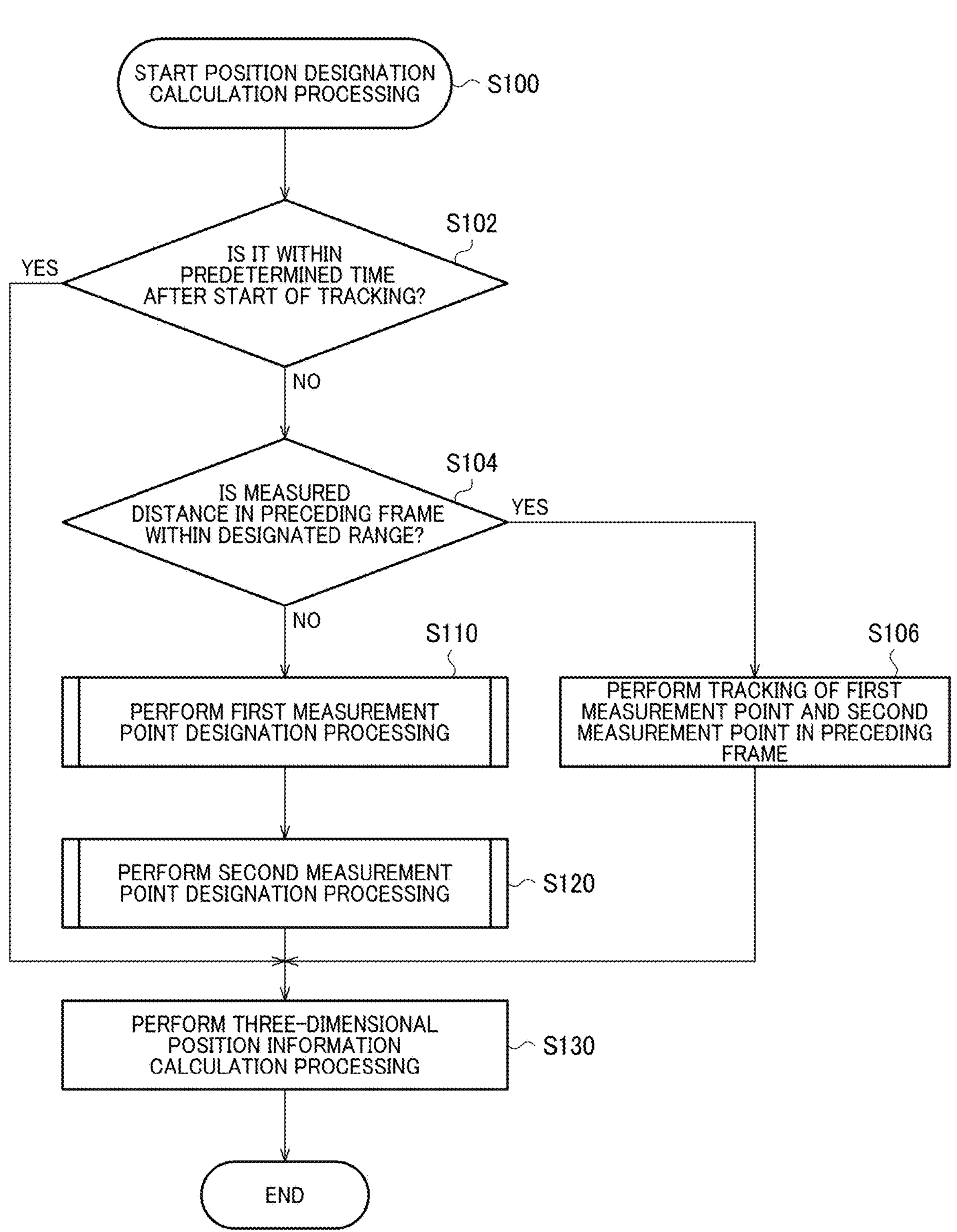
FIG. 35 is a flowchart describing another processing example of the position designation calculation processing.

In FIG. 35, the processor 100 performs processing of determining whether or not it is within the predetermined time after the start of tracking (step S102). In a case of determining that it is not within the predetermined time after the start of the tracking (NO in step S102), the processor 100 performs processing of determining whether or not a measured distance in a preceding frame is within a designated range (step S104). In step S104, more specifically, for example, the processor 100 determines whether or not the distance measured in the last measurement processing (step S200) is within a range of a target measurement value. That is, the designated range in step S104 is a range of a target value in a case where a target distance is desired to be measured. For example, in a treatment of resecting a tumor, there is a case where a resection range is away from a tumor at a designated distance and preliminarily determined based on an inspection result or the like before the treatment. To measure a width of a region associated with resection in such a case, the target distance is set.

Additionally, in a case of determining that the measured distance in the preceding frame is out of the designated range (NO in step S104), the processor 100 performs the first measurement point designation processing (step S110), the second measurement point designation processing (step S120), and the three-dimensional position information calculation processing (step S130), and the flow ends. In contrast, in a case of determining that the measured distance in the preceding frame is within the designated range (YES in step S104), the processor 100 performs processing of tracking the first measurement point 41 and the second measurement point 42 in the preceding frame (step S106). After executing step S106, the processor 100 performs image processing until the elapse of predetermined time to continue tracking of the first measurement point 41 and the second measurement point 42. Note that a method of performing image processing associated with the tracking is known, so that a description thereof is omitted.

In contrast, in a case of determining that it is within the predetermined time after the start of the tracking (YES in step S102), the processor 100 performs the above-mentioned three-dimensional position information calculation processing (step S130), and the flow ends. Note that specific time of the predetermined time is only required to be determined by the user as appropriate. The case where the determination is made as YES in step S102 is a case where the tracking of the first measurement point 41 and the second measurement point 42 continues. In this case, the processor 100 performs stereo matching on a stereo image in a frame newly acquired by the three-dimensional position information calculation processing (step S130) without newly performing the first measurement point designation processing (step S110) and the second measurement point designation processing (step S120). Thereafter, the processor 100 performs display on the second display DP2 so as to superimpose image information regarding the first measurement point 41 and the second measurement point 42 associated with step S106 performed in the preceding frame on the stereo image subjected to the stereo matching. Note that, in a case where the processor 100 performs step S130 as a result of the determination as YES in step S102, the measurement processing (step S200) may be omitted. This is because, due to tracking, the measured distance does not change. Additionally, after the elapse of the above-mentioned predetermined time, the distance information stored in the memory, which is not illustrated, may be deleted. This allows the processor 100 to determine NO in step S104 after the elapse of the predetermined time since the start of the tracking.

Figure 36:
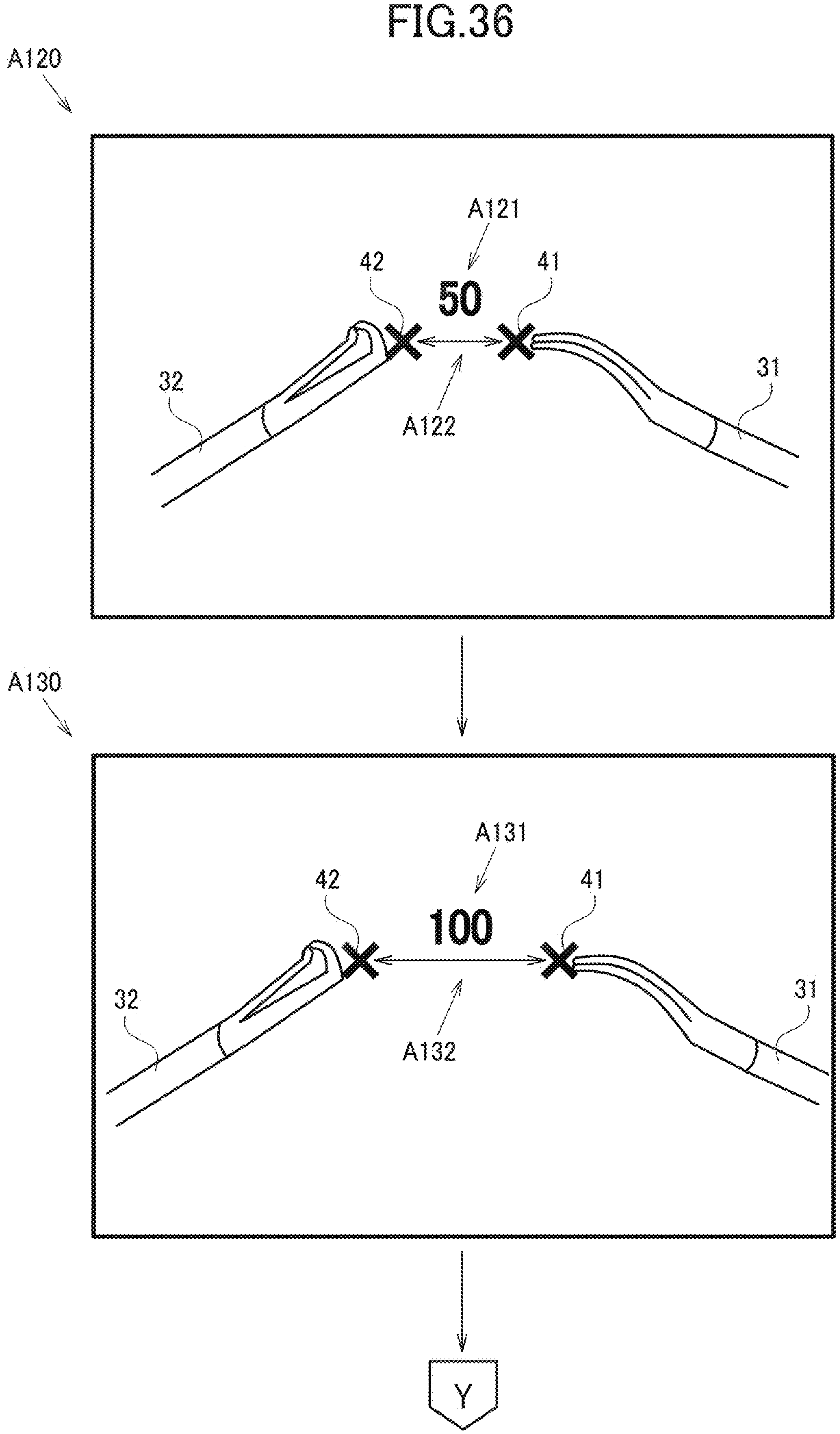
FIG. 36 is a view for describing tracking of the first measurement point and a second measurement point.
Figure 37:
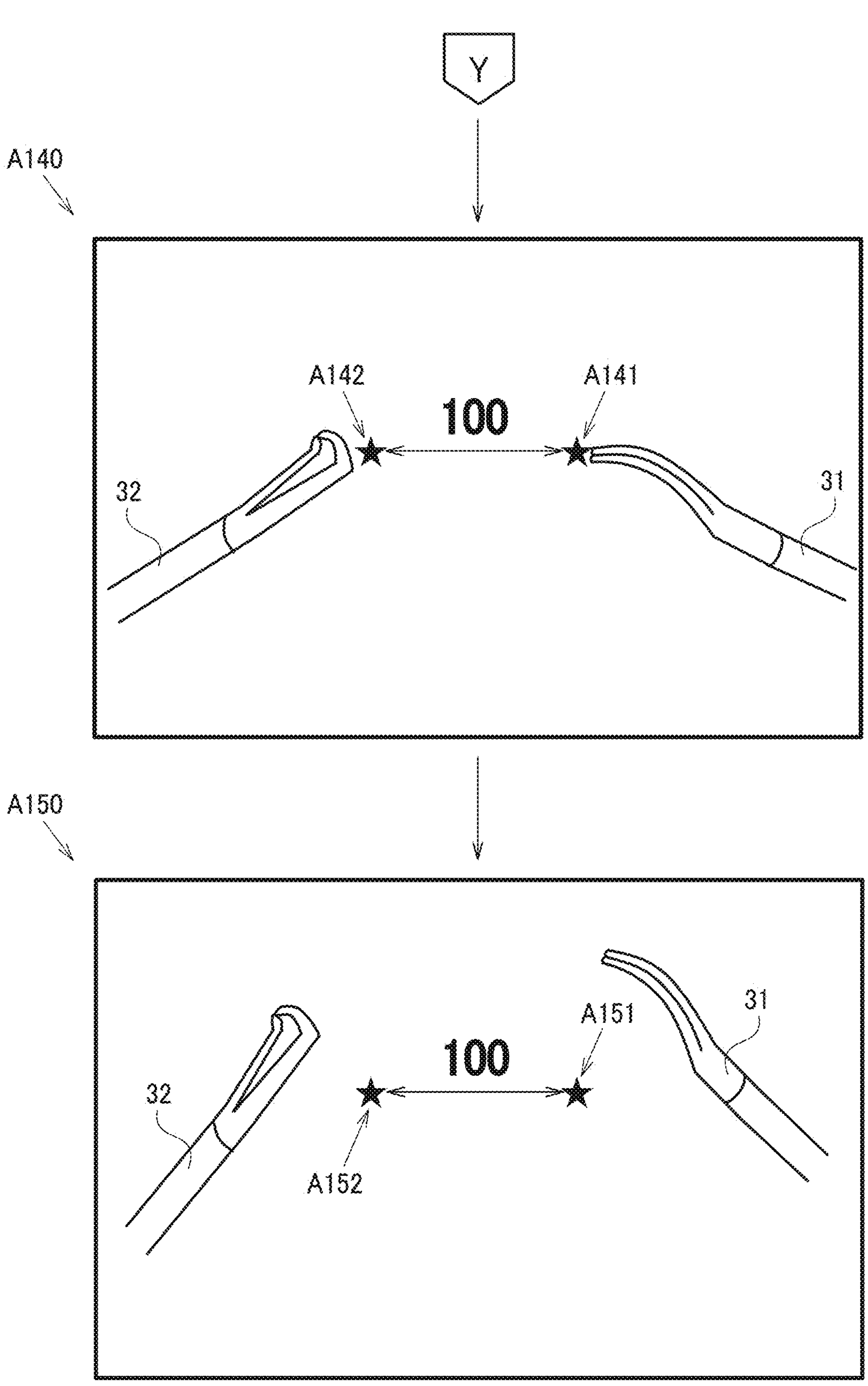
FIG. 37 is another view for describing tracking of the first measurement point and the second measurement point.

A screen example in a case where the processing in FIG. 35 is applied is now described with reference to FIGS. 36 and 37. Note that screen examples in FIGS. 36 and 37 are examples in which the second measurement point 42 is designated as the distal end of the second treatment tool 32, but the processing in FIG. 35 is not prevented from being applied to the case where the second measurement point 42 is designated by the processing in step S122 in FIG. 7.

For example, assume that a screen example indicated by A120 is displayed on the second display DP2 at a first timing. In the screen example indicated by A120, the processor 100 performs the position designation calculation processing (step S100) to designate the distal end of the first treatment tool 31 as the first measurement point 41, and designate the distal end of the second treatment tool 32 as the second measurement point 42. The processor 100 then performs the measurement processing (step S200) and the display updating processing (step S300) to perform display on the second display DP2 so as to superimpose a distance information image indicated by A121 and an arrow image indicated by A122 on the endoscope image.

Additionally, assume that the first timing in the screen example indicated by A120 is a timing at which the distance information associated with the image indicated by A121 is out of the range of the target measurement value. In this case, the processor 100 determines NO in step S104 in FIG. 35 and performs processing in the order of the first measurement point designation processing (step S110), the second measurement point designation processing (step S120), and the three-dimensional position information calculation processing (step S130). That is, the position designation calculation processing (step S100) described in FIG. 35 is substantially identical to the position designation calculation processing (step S100) in FIG. 5 at the first timing illustrated in the screen example indicated by A120.

Assume that the user thereafter operates at least one of the first treatment tool 31 or the second treatment tool 32 so as to change the distance between the first measurement point 41 and the second measurement point 42, and a second timing at which the screen example indicated by A130 is displayed comes. Even in the screen example indicated by A130, similarly to the screen example indicated by A120, the processor 100 performs the position designation calculation processing (step S100) to designate the distal end of the first treatment tool 31 as the first measurement point 41, and designate the distal end of the second treatment tool 32 as the second measurement point 42. Additionally, the processor 100 performs the measurement processing (step S200) and the display updating processing (step S300) to perform display on the second display DP2 so as to superimpose a distance information image indicated by A131 and an arrow image indicated by A132 on the endoscope image.

Assume that the second timing in the screen example indicated by A130 is a timing at which the distance information associated with the image indicated by A131 is within the range of the target measurement value. In this case, the processor 100 determines YES in step S104 in FIG. 35, and performs step S106. With this configuration, the screen example indicated by A130 becomes like a screen example indicated by A140 in FIG. 36.

In the screen example indicated by A140 in FIG. 36, in response to the start of the tracking, the processor 100 performs display processing on the second display DP2 so as to change a display mode of an icon representing the first measurement point 41 and a display mode of an icon representing the second measurement point 42 as indicated by A141 and A142. This allows the user to recognize that step S106 has been executed and the tracking has started. Note that, as described above, the icon representing the first measurement point 41 is not necessarily displayed, and similarly, the display mode of the icon representing the first measurement point 41 is not necessarily changed. The same applies to the icon representing the second measurement point 42.

Note that FIG. 37 illustrates the change of the display modes of the first measurement point 41 and second measurement point 42 allows the user to distinguish whether or not the tracking has started, but the configuration is not limited thereto, and the start of the tracking may be, for example, notified by a predetermined means without change of the display modes of the first measurement point 41 and second measurement point 42. The predetermined means may be, for example, display of a message indicating that the tracking has started on the second display DP2, display of a mark including a predetermined color on the second display DP2, or output of a predetermined voice. Additionally, although not illustrated, the processor 100 may further display remaining time after the start of the tracking until the end of the tracking on the second display DP2.

Assume that a screen example indicated by A150 is displayed at a third timing, which is after the second timing and before the elapse of predetermined time since the second timing. Since the user determines that the measurement of the desired distance has succeeded and further operates the first treatment tool 31 for a reason of performing a treatment or the like afterward, the position of the distal end of the first treatment tool 31 at the third timing is different from the position of the distal end of the first treatment tool 31 at the second timing. Similarly, the position of the distal end of the second treatment tool 32 at the third timing is different from the position of the distal end of the second treatment tool 32 at the second timing.

In this case, based on the determination as YES in step S102 with respect to the frame, the processor 100 performs the stereo matching based on stereo images or the like captured by the imager of the endoscope 20 in the frame. As a result, the position of the first treatment tool 31 and the position of the second treatment tool 32 in the screen example indicated by A150 are different from the position of the first treatment tool 31 and the position of the second treatment tool 32 in the screen example indicated by A140. In contrast, the processor 100 executes step S106 with respect to the preceding frame, and thus tracks the first measurement point 41 and the second measurement point 42 at the second timing. The tracked first measurement point 41 is displayed at a position indicated by A151 at the third timing, and the tracked second measurement point 42 is displayed at a position indicated by A152 at the third timing. The position indicated by A151 is identical to the position indicated by A141, and the position indicated by A152 is identical to the position indicated by A142. Additionally, since the first measurement point designation processing (step S110) is not performed at the third timing, the distal end position of the first treatment tool 31 and the position indicated by A151 are not matched with each other. Similarly, since the second measurement point designation processing (step S120) is not performed at the third timing, the distal end position of the second treatment tool 32 and the position indicated by A152 are not matched with each other.

Note that FIG. 35 illustrates a processing example of tracking the first measurement point 41 and the second measurement point 42 in a case where the measurement of the desired distance has succeeded, but the configuration is not limited thereto, and the user may be able to track the first measurement point 41 and the second measurement point 42 at a freely-selected timing. For example, although illustration is omitted, it is sufficient if an operation button or the like that is operable by the user is included in the image processing device 10, the endoscope 20, or the like, and processing of determining whether or not the processor 100 has received an instruction signal based on the user's operation of the operation button serves as step S104 in FIG. 35. As described above, in the image processing device 10 in accordance with the present embodiment, in a case where the distance measurement value is obtained or the instruction signal is input by the user, the processor 100 tracks the first measurement point 41 and the second measurement point 42 when the measurement value is obtained (step S106), and displays the position of the tracked first measurement point 41 and the position of the tracked second measurement point 42 on the display DP (second display DP2). This allows the user to grasp the desired measurement value, and perform an operation other than the measurement using a treatment tool used for the measurement. This can enhance convenience in the treatment.

Additionally, for example, the processor 100 may use the first treatment tool 31 to which a predetermined texture (for example, a pattern) is added to perform the treatment, and perform the three-dimensional position information calculation processing (step S130) in FIG. 5 to calculate the three-dimensional position information regarding the first measurement point 41.

Figure 38:
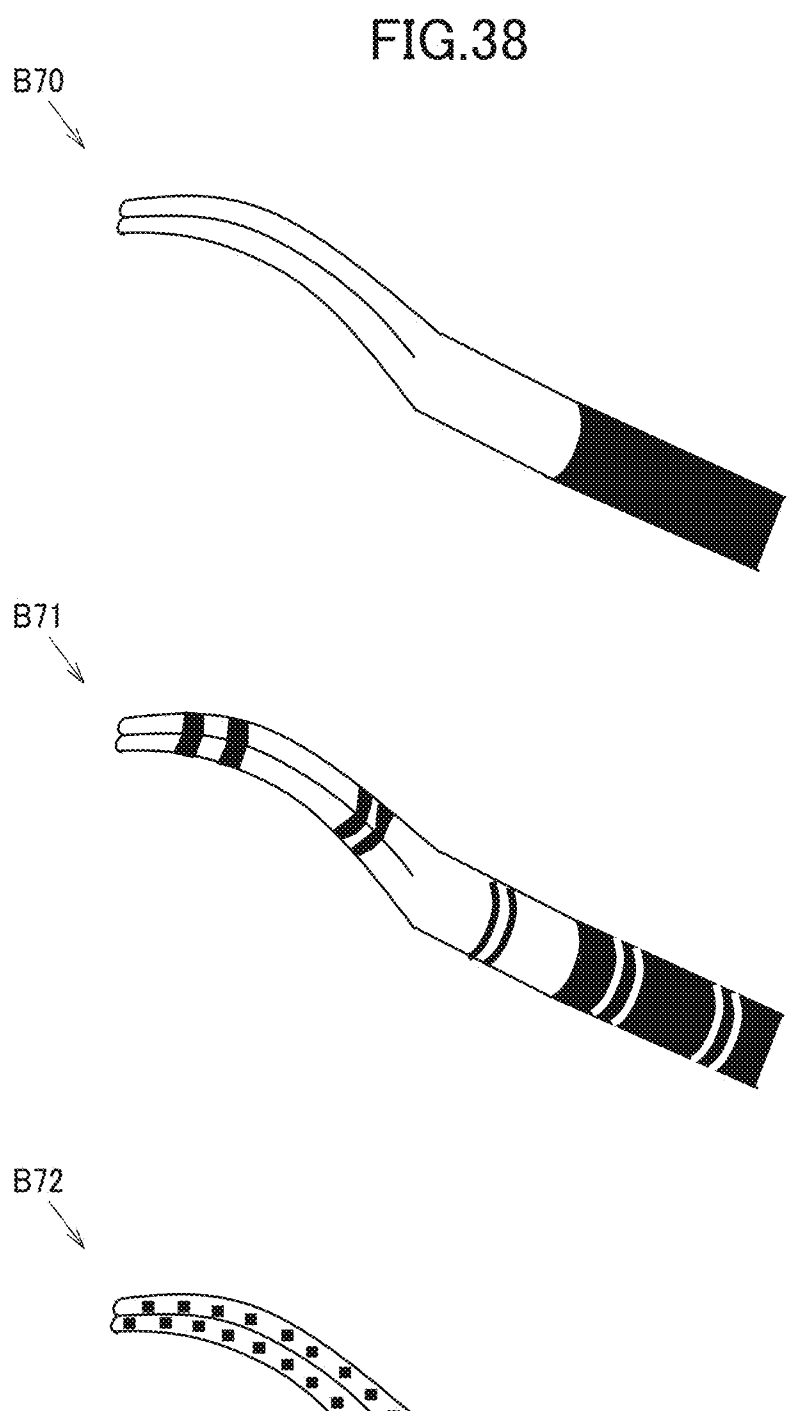
FIG. 38 is a view for describing examples of textures added to the first treatment tool.

The treatment tool used for a manipulation in accordance with the present embodiment includes a metal portion and a shank portion. As indicated by B70 in FIG. 38, there is a small difference in pixel values of pixels associated with the metal portion in the criterion image and the reference image, and there is a possibility that the accuracy of the stereo matching decreases. The same applies to the shank portion. To address this, for example, a predetermined texture is added to the metal portion and shank portion of the first treatment tool 31 as indicated by B71 or B72, whereby it is possible to increase the accuracy of matching in the stereo matching. The predetermined texture is not limited to the example indicated by B71 or B72, and can be modified in various manners.

The predetermined texture can be implemented by, for example, direct application of a color or the like to the first treatment tool 31.

Alternatively, the processor 100 may perform processing of irradiating the first treatment tool 31 with predetermined pattern light from a light source device included in the distal end of the endoscope 20, acquire the criterion image and the reference image from the endoscope 20 in a state where the first treatment tool 31 is irradiated with the predetermined pattern light, and thereby perform the stereo matching.

Note that, as described above with reference to FIG. 14, in a case where the distal end position of the second treatment tool 32 serves as the second measurement point 42, the predetermined texture may be added to both the first treatment tool 31 and the second treatment tool 32, but a certain effect can be expected even if the predetermined texture is added only to the first treatment tool 31. As described above, the image processing device 10 in accordance with the present embodiment includes the first treatment tool 31, and the texture for increasing the accuracy of the measurement of the first measurement point 41 is added to the first treatment tool 31. This allows the processor 100 to obtain parallax with higher accuracy, and thereby calculate the three-dimensional position information regarding the first measurement point 41 with higher accuracy. With this configuration, it is possible to measure the distance between the first measurement point 41 and the second measurement point 42 with higher accuracy.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, components in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above.

Example 1

1. An image processing device comprising:
 a processor configured to perform display processing on a display,
 wherein the processor
  uses an endoscope image of a subject, the endoscope image being acquired by an endoscope, to calculate three-dimensional position information regarding a first treatment tool and a predetermined portion in the endoscope image,
  measures a distance between a first measurement point on a distal end side of the first treatment tool and a second measurement point associated with the predetermined portion based on the three-dimensional position information regarding the first treatment tool and the predetermined portion, and
  performs display processing to indicate whether or not measurement of the distance is in a stable state on the display.

Example 2

An image processing method to be executed by a computer, the method comprising:
 performing processing of displaying an endoscope image of a subject on a display, the endoscope image being acquired by an endoscope;
 using the endoscope image of the subject to calculate three-dimensional position information regarding a first treatment tool and a predetermined portion in the endoscope image;
 measuring a distance between a first measurement point on a distal end side of the first treatment tool and a second measurement point associated with the predetermined portion based on the three-dimensional position information regarding the first treatment tool and the predetermined portion; and
 performing processing of displaying whether or not measurement of the distance is in a stable state.

What is claimed is:

1. An image processing device comprising:
 a processor comprising hardware, wherein the processor is configured to:
 calculate, based on an endoscope image of a subject, the endoscope image being acquired by an endoscope, three-dimensional position information regarding a first treatment tool and a first portion in the endoscope image;

measure a distance between a first measurement point on the first treatment tool and a second measurement point associated with the first portion based on the three-dimensional position information regarding the first treatment tool and the first portion;

perform a determination of whether a measurement of the distance is in a stable state; and control a display to display a result of the determination.

2. The image processing device as defined in claim 1, wherein:

the three-dimensional position information regarding the first portion is three-dimensional position information regarding a second treatment tool; and the processor is configured to measure the distance between the first measurement point on the distal end side of the first treatment tool and the second measurement point on a distal end side of the second treatment tool based on the three-dimensional position information regarding the first treatment tool and the first portion.

3. The image processing device as defined in claim 1, wherein:

the three-dimensional position information regarding the first portion includes the three-dimensional position information regarding the second measurement point at a position of the subject corresponding to a position designated by a user on the display; and the processor is configured to measure the distance between the first measurement point on the distal end side of the first treatment tool and the second measurement point based on the three-dimensional position information regarding the first treatment tool and the first portion.

4. The image processing device as defined in claim 1, wherein in performing the determination of whether the measurement of the distance is in the stable state, the processor is configured to:

determine whether the first measurement point and the second measurement point are stably measured for a predetermined period of time or whether the distance is stably measured for the predetermined period of time; and in response to determining the first measurement point and the second measurement point are stably measured for the predetermined period of time or the distance is stably measured for the predetermined period, determine that the measurement of the distance is in the stable state.

5. The image processing device as defined in claim 4, wherein the processor is configured to:

determine whether at least a moving amount of the first measurement point is within a first predetermined range in a first predetermined period of time; and in response to determining that the at least the moving amount of the first measurement point is within the first predetermined range in the first predetermined period of time, determine that the measurement of the distance is in the stable state.

6. The image processing device as defined in claim 5, wherein the processor is configured to control the display to display image information to at least make the moving amount of the first measurement point within the first predetermined range.

7. The image processing device as defined in claim 4, wherein the processor is configured to:

determine whether a change mount of the distance is within a second predetermined range in a second predetermined period of time; and in response to determining that the change amount of the distance is within the second predetermined range in the second predetermined period of time, determine that the measurement of the distance is in the stable state.

8. The image processing device as defined in claim 1, wherein the processor is configured to change a display mode of a measurement value of the distance depending on whether or not the measurement of the distance is in the stable state.

9. The image processing device as defined in claim 1, wherein the processor is configured to control the display to display a graph indicating a period of time of the stable state of the measurement of the distance.

10. The image processing device as defined in claim 1, wherein the processor is configured to:

determined whether the endoscope image is stable for a predetermined period of time;

in response to determining that the endoscope image is stable for the predetermined period of time, control the display to indicate that the endoscope image is stable for the predetermined period of time on the display.

11. The image processing device as defined in claim 1, wherein the processor is configured to:

determine whether the first treatment tool is parallel with a parallax direction in a stereo view of the endoscope image; and in response to determining that the first treatment tool is parallel with the parallax direction in the stereo view of the endoscope image, control the display to display instruction to incline the first treatment tool with respect to the parallax direction.

12. The image processing device as defined in claim 1, wherein the processor is configured to:

determine whether the first treatment tool is parallel with a parallax direction in a stereo view of the endoscope image; and in response to determining that the first treatment tool is parallel with the parallax direction in the stereo view of the endoscope image, control the display to display an object representing an inclination direction of the first treatment tool.

13. The image processing device as defined in claim 1, wherein the processor is configured to perform smoothing processing in a time direction or the smoothing processing in a spatial direction on at least the first measurement point to measure the distance.

14. The image processing device as defined in claim 13, wherein the processor is configured to use a line-of-sight vector based on a median value or an average value of depth coordinates in a peripheral region in measurement position coordinates of the first measurement point in the endoscope image and the measurement position coordinates to obtain the three-dimensional position information regarding the first measurement point.

15. The image processing device as defined in claim 1, wherein the processor is configured to obtain the three-dimensional position information with an intersection point between a straight line based on the three-dimensional position information regarding at least a portion of an axis portion of the first treatment tool and the three-dimensional position information regarding a distal end of the first treatment tool and the subject serving as the first measurement point.

16. The image processing device as defined in claim 1, wherein the processor is configured to calculate the three-dimensional position information regarding the first measurement point based on a predetermined position on a straight line based on two-dimensional position information regarding at least a portion of an axis portion of the first treatment tool and the two-dimensional position information regarding a distal end of the first treatment tool.

17. The image processing device as defined in claim 1, wherein the processor is configured to:

determine whether a measurement value of the distance is obtained or whether an instruction signal is input by a user; and in response to determining that the measurement value of the distance is obtained or the instruction signal is input by the user:

perform tracking of the first measurement point and the second measurement point when the measurement value is obtained; and control the display to display a position of the tracked first measurement point and a position of the tracked second measurement point on the display.

18. An endoscope system comprising:

the image processing device as defined in claim 1; and the endoscope.

19. An image processing method executed by a computer, the image processing method comprising:

calculating, based on an endoscope image of a subject, the endoscope image being acquired by an endoscope, three-dimensional position information regarding a first treatment tool and a first portion in the endoscope image;

measuring a distance between a first measurement point on a distal end side of the first treatment tool and a second measurement point associated with the first portion based on the three-dimensional position information regarding the first treatment tool and the first portion;

performing a determination of whether a measurement of the distance is in a stable state; and controlling a display to display a result of the determination.

20. A non-transitory information storage medium that stores a program to cause a computer to execute processes comprising:

calculating, based on an endoscope image of a subject, the endoscope image being acquired by an endoscope, three-dimensional position information regarding a first treatment tool and a first portion in the endoscope image;

measuring a distance between a first measurement point on a distal end side of the first treatment tool and a second measurement point associated with the first portion based on the three-dimensional position information regarding the first treatment tool and the first portion;

performing a determination of whether a measurement of the distance is in a stable state; and controlling a display to display a result of the determination.

* * * * *